United States Patent [19]

Bodor

[11] Patent Number: 5,155,227
[45] Date of Patent: Oct. 13, 1992

[54] COMPOUNDS FOR SITE-ENHANCED DELIVERY OF RADIONUCLIDES

[75] Inventor: Nicholas S. Bodor, Gainesville, Fla.

[73] Assignee: University of Florida, Gainesville, Fla.

[21] Appl. No.: 561,920

[22] Filed: Aug. 2, 1990

Related U.S. Application Data

[60] Division of Ser. No. 88,523, Aug. 21, 1987, Pat. No. 4,963,688, which is a continuation of Ser. No. 879,120, Mar. 19, 1986, abandoned, which is a continuation-in-part of Ser. No. 632,314, Jul. 19, 1984, abandoned.

[30] Foreign Application Priority Data

Jul. 15, 1985 [WO] PCT Int'l Appl. ... PCT/US85/01334

[51] Int. Cl.$^5$ ............... C07D 215/10; C07D 215/16; C07D 217/12; C07D 213/55; C07D 213/56
[52] U.S. Cl. ..................... 546/146; 546/147; 546/168; 546/169; 546/170; 546/174; 546/175; 546/314; 546/318
[58] Field of Search ............ 546/318, 168, 146, 147, 546/314, 169, 170, 174, 175

[56] References Cited

U.S. PATENT DOCUMENTS

| | | | |
|---|---|---|---|
| 3,823,076 | 7/1974 | Rushmere et al. | 546/318 |
| 4,775,763 | 10/1988 | Dolton et al. | 546/318 |
| 4,963,688 | 10/1990 | Bodor | 546/316 |

Primary Examiner—David B. Springer
Attorney, Agent, or Firm—Burns, Doan, Swecker & Mathis

[57] ABSTRACT

A dihydropyridine⇌pyridinium salt type of redox, or chemical, delivery system for the site-specific and/or site-enhanced delivery of a radionuclide to the brain. A chelating agent capable of chelating with a radionuclide and having a reactive hydroxyl, carboxyl, amino, amide or imide group is coupled to a carrier moiety comprising a dihydropyridinie⇌pyridinium salt nucleus and then complexed with a radionuclide to provide a new radionuclide pharmaceutial that, in its lipoidal dihydropyridine form, penetrates the blood-brain barrier ('BBB') and allows increased levels of radionuclide concentration in the brain, particularly since oxidation of the dihydropyridine carrier moiety in vivo to the ionic pyridinium salt retards elimination from the brain while elimination from the general circulation is accelerated. This radionuclide delivery system is well suited for use in scintigraphy and similar radiographic techniques.

68 Claims, No Drawings

COMPOUNDS FOR SITE-ENHANCED DELIVERY OF RADIONUCLIDES

CROSS-REFERENCE TO RELATED APPLICATIONS

This application is a division of applicant's copending application Ser. No. 07/088,523, filed Aug. 21, 1987, now U.S. Pat. No. 4,963,688, which is a continuation of U.S. Ser. No. 06/879,120, filed Mar. 19, 1986, now abandoned, which is a continuation-in-part of application Ser. No. 06/632,314, filed Jul. 19, 1984, now abandoned. Application Ser. No. 06/879,120 is the U.S. national phase of International PCT Application No. PCT/US 85/01334, filed Jul. 15, 1985.

FIELD OF THE INVENTION

The present invention relates to a dihydropyridine⇌pyridinium salt type of redox, or chemical, delivery system for the site-specific and/or site-enhanced delivery of a radionuclide to the brain and other organs. More particularly, this invention relates to the discovery that a chelating agent capable of chelating with a radionuclide and having a reactive hydroxyl, carboxyl, amino, amide or imide group can be coupled to a carrier moiety comprising a dihydropyridine⇌pyridinium salt nucleus and then complexed with a radionuclide to provide a new radiopharmaceutical that, in its lipoidal dihydropyridine form, penetrates the blood-brain barrier ("BSB") and allows increased levels of radionuclide concentration in the brain, particularly since oxidation of the dihydropyridine carrier moiety in vivo to the ionic pyridinium salt retards elimination from the brain while elimination from the general circulation is accelerated.

The present radionuclide delivery system is well suited for use in scintigraphy and similar radiographic techniques.

BACKGROUND OF THE INVENTION

Radiographic techniques such as scintigraphy, and the like, find application in biological and medical procedures for diagnosis as well as research. Scintigraphy involves the use of radiopharmaceuticals; i.e., compounds containing (or labeled with) a radioisotope (i.e. radionuclide) which upon introduction into a mammal become localized in specific organs, tissue, or skeletal material that are sought to be imaged. When the radiopharmaceutical is so localized, traces, plates, or scintiphotos of the existing distribution of the radionuclide may be made by various radiation detectors known in the art. The observed distribution of the localized radionuclide can then be used to detect the presence of pathological conditions, abnormalities, and the like. Radiopharmaceuticals are thus often referred to as radiodiagnostics.

In many cases, radiopharmaceuticals are prepared using target-specific chelating agents which provide a bridge connecting a radionuclide, such as a radioactive metal like technetium-99m, or the like, and a material which will temporarily localize in the organ, tissue, or skeletal material which is to be imaged. Typical chelating agents for such purposes are: polydentate ligands that form a 1:1 or 2:1 ligand:radioactive metal complex; macrocyclic ligands of appropriate ring size and preferably where all coordinating atoms are in a planar configuration; and bicyclic or polycyclic ligands that can encapsulate the radioactive metal.

It is a well established fact that the delivery of drugs, including radiopharmaceuticals, to the brain is often seriously limited by transport and metabolism factors and, more specifically, by the functional barrier of the endothelial brain capillary wall deemed the blood-brain barrier. Site-specific delivery and/or sustained delivery of drugs to the brain are even more difficult.

It has been previously suggested to deliver a drug species, specifically N-methylpyridinium-2-carbaldoxime chloride (2-PAM), into the brain, the active nucleus of which in and of itself constitutes a quaternary pyridinium salt, by way of the dihydropyridine latentiated prodrug form thereof. Such approach is conspicuously delimited to relatively small molecule quaternary pyridinium ring-containing drug species and does not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ results, and obviously no brain-specific, sustained delivery occurs as any consequence thereof: the 2-PAM is eliminated as fast from the brain as it is from the general circulation and other organs. Compare U.S. Pat. Nos. 3,929,813 and 3,962,447; Bodor et al, *J. Pharm. Sci.*, 67, No. 5, pp. 685–687 (1978); Bodor et al, *Science*, Vol. 190 (1975), pp. 155–156; Shek, Higuchi and Bodor, *J. Med. Chem.*, Vol. 19 (1976), pp. 113–117. A more recent extension of this approach is described by Brewster, *Dissertation Abstracts International*, Vol. 43, No. 09, March 1983, p. 2910B. It has also been speculated to deliver, e.g., an antitumor agent, into the brain by utilizing a dihydropyridine/pyridinium redox carrier moiety therefor, but this particular hypothesis necessarily entails derivatizing the dihydropyridine/pyridinium carrier with a substituent itself critically designed to control the release rate of the active drug species from the quaternary derivative thereof, as well as being critically functionally coordinated with the particular chemical and therapeutic activity/nature of the antitumor drug species itself; Bodor et al, *J. Pharm. Sci.*, supra. See also Bodor, "Novel Approaches for the Design of Membrane Transport Properties of Drugs", in *Design of Biopharmaceutical Properties Through Prodrugs and Analogs*, Roche, E. B. (ed.), APhA Academy of Pharmaceutical Sciences, Washington, D.C., pp. 98–135 (1976).

More recently, Bodor et al, *Science*, Vo. 214, Dec. 18, 1981, pp. 1370–1372, have reported on site-specific sustained release of drugs to the brain. The *Science* publication outlines a scheme for specific and sustained delivery of drug species to the brain, as depicted in the following Scheme 1:

SCHEME 1: BBB: BLOOD-BRAIN BARRIER

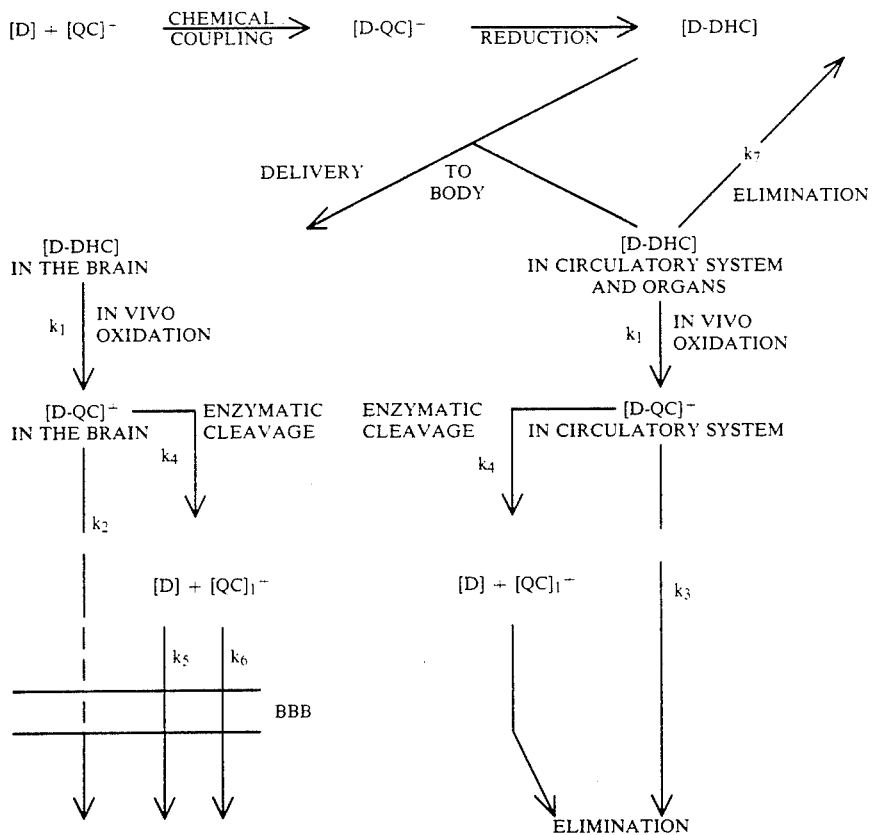

According to the scheme in *Science*, a drug [D] is coupled to a quaternary carrier [QC]+ and the [D-QC]+ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]+ quaternary salt which, because of its ionic, hydrophilic character, should be rapidly eliminated from the general circulation of the body, while the blood-brain barrier should prevent its elimination from the brain ($k_3 >> k_2$; $k_3 >> k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 >> k_2$). Because of the facile elimination of [D-QC]+ from the general circulation, only minor amounts of drug are released in the body ($k_3 >> k_4$); [D] will be released primarily in the brain ($k_4 > k_2$). The overall result ideally will be a brain-specific sustained release of the target drug species.

Bodor et al have reported, in *Science*, their work with phenylethylamine as the drug model, which was coupled to nicotinic acid, then quaternized to give compounds of the formula

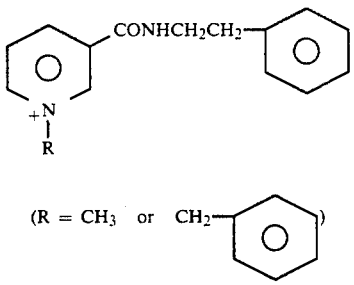

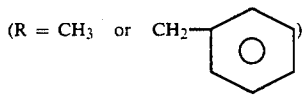

($R = CH_3$ or $CH_2$—⌬)

which were subsequently reduced by sodium dithionite to the corresponding compounds of the formula

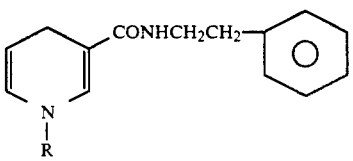

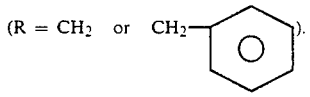

($R = CH_2$ or $CH_2$—⌬).

Testing of the N-methyl derivative in vivo supported the criteria set forth in Scheme 1. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed.

Other reports of Bodor et al's work have appeared in *The Friday Evening Post*, Aug. 14, 1981, Health Center Communications, University of Florida, Gainesville, Fla.; *Chemical & Engineering News*, Dec. 21, 1981, pp. 24–25; and *Science News*, Jan. 2, 1982, Vol. 121, No. 1, page 7. These publications do not suggest any carrier systems other than the specific N-methyl and N-benzyl nicotinic acid-type carriers disclosed in the *Science* publication. Other classes of drugs as well as a few specific drugs are mentioned as possible candidates for derivatization; for example, steroid hormones, cancer drugs and memory enhancers are indicated as targets for possible future work, as are enkephalins, and specifically, dopamine and testosterone. The publications do not suggest how to link such drugs to the carrier, except possibly when the drugs are simple structures containing a single $NH_2$ or, perhaps, simple structures containing a single OH, of the primary or secondary type, as is the case with phenylethylamine or testosterone. There is, for example, no suggestion of how one of ordinary skill in the art would form a drug-carrier combination when the drug has a more complicated chemical structure than phenylethylamine, e.g., dopamine or an enkephalin. For further details concerning the work with phenylethylamine, dopamine and testosterone, see also Bodor et al, *J. Med. Chem.*, Vol. 26, March 1983, pp. 313–317; Bodor et al, *J. Med. Chem.*, Vol. 26, April 1983, pp. 528–534; Bodor et al, *Pharmacology and Therapeutics*, Vol. 19, No. 3, pp. 337–386 (April 1983), and Bodor et al, *Science*, Vol. 221, July 1983, pp. 65–67.

In view of the foregoing, it is apparent that there has existed an acutely serious, long-standing need for a truly effective, generic but nonetheless flexible, method for the site-specific or sustained delivery, or both, of drug species to the brain. This need has been addressed in International Patent Application No. PCT/US83/00725 (filed by UNIVERSITY OF FLORIDA on May 12, 1983 and published under International Publication No. W083/03968 on Nov. 24, 1983), which provides such a generic method for site-specific, sustained delivery of drugs to the brain utilizing a dihydropyridine⇌pyridinium salt type of redox carrier system. According to the PCT application, a drug (typically having a reactive —OH, —COOH or —NH2 group) can be coupled to a dihydropyridine⇌pyridinium carrier; the lipoidal dihydro form of the drug-carrier system readily crosses the blood-brain barrier; the dihydropyridine moiety is then oxidized in vivo to the ideally inactive quaternary form, which is "locked in" the brain, while it is facilely eliminated from the general circulation; enzymatic cleavage of the "locked in" quaternary effects a sustained delivery of the drug itself to the brain, to achieve the desired biological effect. Diagnostic agents such as radiopharmaceuticals are generally disclosed in the PCT application as possible candidates for the carrier system, but the synthetic approach of that application, which utilizes the drug itself as the starting material, is not desirable when radioactive materials, especially relatively short-lived radionuclides, are involved. Moreover, in the case of radionuclides, the earlier objective of an ideally inactive form locked in the brain would not achieve the desired result. Thus, a serious need still exists for an effective general method for the site-specific and/or sustained delivery of a desired radionuclide to the brain.

SUMMARY OF THE INVENTION

It has now been found that a chemical delivery system based upon a dihydropyridine⇌pyridinium salt type redox carrier is uniquely well suited for an effective site-specific and/or sustained and/or enhanced delivery of a radionuclide to the brain or like organ, via novel carrier-containing radiopharmaceuticals, and novel carrier-containing chelating agents and novel carrier-containing precursors thereto, useful in the preparation of said radiopharmaceuticals. In one aspect, the present invention thus provides novel carrier-containing chelating agent precursors having the formula

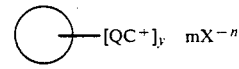  (I)

wherein

is the residue of a chelating agent capable of chelating with a metallic radionuclide, said chelating agent having at least one reactive functional group selected from the group consisting of amino, carboxyl, hydroxyl, amide and imide, said functional group being not essential for the complexing properties of said chelating agent, said residue being characterized by the absence of a hydrogen atom from at least one of said reactive functional groups of the chelating agent: y is 1 or 2; [QC+] is the hydrophilic, ionic pyridinium salt form of a dihydropyridine⇌pyridinium salt redox carrier; X− is the anion of a pharmaceutically acceptable organic or inorganic acid; n is the valence of the acid anion; and m is a number which when multiplied by n is equal to y.

In another aspect, the present invention provides novel carrier-containing chelating agents having the formula

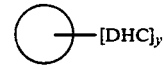  (II)

and the non-toxic pharmaceutically acceptable salts thereof, wherein

and y are defined as above, and [DHC] is the reduced, biooxidizable, blood-brain barrier penetrating form of dihydropyridine⇌pyridinium salt redox carrier.

In yet another aspect, the present invention provides, as an effective radionuclide delivery system, novel carrier-containing radiopharmaceuticals of the formula

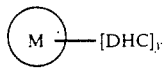
(III)

and the non-toxic pharmaceutically acceptable salts thereof, wherein M is a metallic radionuclide and the remaining structural variables are defined as before; in other words, (III) is the chelated, or complexed, counterpart of (II), formed by complexing the novel carrier-containing chelating agent of formula (II) with a radioactive metal. When a radiopharmaceutical of formula (III) is administered, it readily penetrates the BBB. Oxidation of (III) in vivo affords the corresponding pyridinium salt of the formula

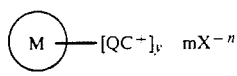
(IV)

wherein the structural variables are as defined above. Because of its hydrophilic, ionic nature, the formula (IV) substance is "locked-in" the brain, thus allowing radiographic imaging of the radionuclide present in the complex (IV). While the quaternary "locked-in" form will gradually cleave to release the carrier moiety and the chelate portion of the molecule, such cleavage will generally occur after the most desirable period for radiographic imaging has already passed. It is generally considered most desirable, from the standpoint of patient and technician safety, to image the target area as soon as possible after administration and to use relatively short-lived radioisotopes. Under such circumstances, the "locked-in" quaternary form will likely not degrade to the noncarrier-containing chelate until after the radioactivity has decayed to a considerable extent. Thus, the present invention does not in fact provide a system for delivery and imaging of previously known radiopharmaceuticals; by the time the present delivery system degrades to a chelate of a known chelating agent and a radioactive metal, said chelate will generally no longer be sufficiently radioactive for practical imaging. Moreover, once such degradation occurs, the known chelate may not be retained in the brain in sufficient amounts to allow imaging thereof. Thus, in contrast to the teachings of the Bodor et al publications and the aforementioned PCT application, which emphasize the desirability of an inactive quaternary form locked in the brain, the present invention provides, and indeed requires, an active quaternary form locked in the brain in order to allow effective radionuclide imaging.

The present chelate/carrier system for radionuclides is characterized by enhanced efficacy and decreased toxicity. Indeed, consistent herewith systemic toxicity is significantly reduced by accelerating the elimination of the quaternary carrier system from the general circulation.

Technetium-99m is a preferred radionuclide for diagnostic purposes because of its favorable radiation energy, its relatively short half-life, and the absence of corpuscular radiation, and is preferred for use in the present invention. Other radionuclides that can be used diagnostically herein in a chelated form are cobalt-57, gallium-67, gallium-68, indium-111, indium-111m, and the like.

DETAILED DESCRIPTION OF THE INVENTION

The following definitions are applicable:

The term "drug" as used herein means any substance intended for use in the diagnosis, cure, mitigation, treatment or prevention of disease in man or other animal.

The term "lipoidal" as used herein designates a carrier moiety which is lipid-soluble or lipophilic.

The expression "non-toxic pharmaceutically acceptable salts" as used herein generally includes the non-toxic salts of products of the invention of structures (II) and (III) hereinabove formed with non-toxic, pharmaceutically acceptable inorganic or organic acids of the general formula HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a pharmaceutically acceptable organic or inorganic acid" as used herein, e.g. in connection with structures (I) and (IV) above, is intended to include anions of such HX acids.

It will be appreciated from the foregoing that a compound of formula (III) may be administered as the free base or in the form of a non-toxic pharmaceutically acceptable salt thereof, i.e. a salt which can be represented by the formula

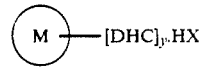

wherein M,

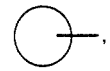

[DHC], y and HX are defined as before; and that, regardless of the actual form in which the compound is administered, it will be converted in vivo to a quaternary salt of formula (IV), the anion $X^-$ being present in vivo. It is not necessary that the anion be introduced as part of the compound administered. Indeed, even when the compound of formula (III) is used in its salt form, the anion of the formula (IV) compound in vivo is not necessarily the same as that present in the formula (III) compound. In fact, the exact identity of the anionic portion of the compound of formula (IV) is immaterial to the in vivo transformation of (III) to (IV).

In the expression "at least one reactive functional group selected form the group consisting of amine, carboxyl, hydroxyl, amide and imide" as used herein, the designated reactive functional groups have the following meanings:

The word "amino" means any primary or secondary amino function, i.e. $-NH_2$ or $-NHR$ where R is typically $C_1-C_7$ alkyl or is a portion of the chelating agent residue itself. The secondary amino function is also represented herein as $-NH-$, particularly since the exact identity of the R portion of $-NHR$ is immaterial, just so long as it does not prevent the formation of the chelating agent residue and its linkage to the carrier moiety or otherwise interfere with the objects of this invention.

The word "carboxyl" means a —COOH function.

The word "hydroxyl" means an —OH function.

The word "amide" means a carbamoyl (—CONH$_2$) or substituted carbamoyl (—CONHR, where R is typically C$_1$-C$_7$ alkyl) functional group. The —CONHR group may also be represented herein as —CONH—, since the exact identity of the R portion of —CONHR is immaterial, just so long as it does not prevent the formation of the chelating agent residue and its linkage to the carrier moiety or otherwise interfere with the objects of this invention.

The word "imide" means a functional group having the structure

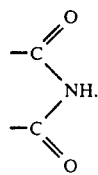

that is, the structure which characterizes imides (i.e. compounds such as succinimide, pathalimide and so forth).

The expression "said functional group being not essential for the complexing properties of said chelating agent" is believed to be self-explanatory. Any functional group in the chelating agent which can be linked to the carrier moiety without destroying the chelating agent's ability to complex with the radionuclide is considered herein to be not essential for complexing properties. On the other hand, derivation of a functional group which would lead to a carrier-containing structure which would be incapable of complexing with a radionuclide is not within the ambit of this invention.

In accord with the present invention, the sustained delivery of a radionuclide to the brain in sufficient concentrations for radioimaging can be effected with much lower concentrations in the peripheral circulation and other tissues. The present invention of course will allow such imaging of any other organs or glands in which sufficient radioactivity accumulates. Thus, for example, it is expected that the quaternary form (IV) which is locked in the brain will be locked in the testes as well. See the aforementioned PCT application.

The novel radionuclide delivery system of this invention begins with the preparation of the novel carrier-containing chelating agent precursors of formula (I). The preparation of those precursors will be tailored to the particular chelating portion and carrier portion to be combined, and especially to the nature of the chemical bond between them, e.g. whether the linkage is an ester or amide linkage, as well as to the presence or absence of other reactive functional groups (amino, mercapto, carboxyl, hydroxy) in either the chelating or carrier portion. Typically, if such other reactive groups are present, they are found in the chelating portion. In any event, when such groups are present and it is desired to protect them, a step that introduces appropriate protecting groups can be incorporated at a suitable stage of the synthetic pathway. Protective groups are well known in the art and include t-butoxycarbonyl for amino groups, N-methylerteacetamido for mercaptans, and N-hydroxysuccinimidyl for carboxyl groups. Acyl or carbonate groups are typically utilized to protect alcohol hydroxyls. When carbonate protecting groups are desired, the step of introducing the protecting groups will involve reacting the alcohol with a halocarbonate of the type ROCOCl or ROCOBr (formed by reaction of ROH with COCl$_2$ or COBr$_2$, R typically being lower alkyl). For acyl protecting groups, the alcoholic hydroxyl is reacted with an acyl halide RCl or RBr, R being —COCH$_3$ or —COC(CH$_3$)$_3$. Yet other reaction schemes and reactants will be readily apparent to those skilled in the art as will the appropriate means for removing such protective groups after they have achieved their function and are no longer needed.

In forming the precursors of formula (I), at least one —COOH, —OH, primary or secondary amino, amide or imide group in a chelating agent will be bonded to [QC$^+$], the hydrophilic, ionic pyridinium salt form of a dihydropyridine $\rightleftharpoons$ pyridinium salt redox carrier.

It will be appreciated that by [QC$^+$] there is intended any non-toxic carrier moiety comprising, containing or including the pyridinium nucleus, whether or not a part of any larger basic nucleus, and whether substituted or unsubstituted, the only criterion therefor being capacity for chemical reduction to the corresponding dihydropyridine form [DHC], BBB-penetration of [DHC] and in vivo oxidation of [DHC] back to the quaternary pyridinium salt carrier moiety [QC$^+$].

As aforesaid, the ionic pyridinium salt radiopharmaceutical/carrier entity of formula (IV) which results from in vivo oxidation of the dihydropyridine form (III) is prevented from efflux from the brain, while elimination from the general circulation is accelerated. Radioimaging of the radionuclide present in the "locked in" formula (IV) quaternary allows observation of the distribution of the localized radionuclide for diagnosis of pathological conditions, abnormalities, etc. Subsequently, the coupling between the particular radioactive species

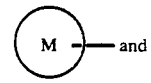

the quaternary carrier [QC]$^+$ is likely metabolically cleaved which results in facile elimination of the carrier moiety [QC$^+$].

Coupling between the chelate moiety and the quaternary carrier can be a simple direct chemical bond, e.g., an amide bond or ester bond, or any other like bond, or same can even be comprised of a linking group or function as is illustrated in the Examples or the ethylenediamine group illustrated in Schemes 3 and 4. Nonetheless, the bond is intended to be, and is hereby defined as, inclusive of all such alternatives.

Eventual cleavage of the formula (IV) quaternary with facile elimination of the carrier moiety [QC$^+$] is characteristically an enzymatic or chemical cleavage, e.g., by an amidase, albeit any type in brain cleavage which might result, whether enzymatic, metabolic or otherwise, of course remains within the ambit of this invention.

The many different dihydropyridine $\rightleftharpoons$ pyridinium salt redox carrier moieties illustrated for use hereinbelow are merely exemplary of the many classes of carriers contemplated by this invention. While the following list of carrier classes is not meant to be exhaustive (and, indeed yet other carrier classes are illustrated hereinbelow as well as in the aforementioned PCT application, PCT/US83/00725), the following major classes of quaternaries and the corresponding dihydro forms are prime examples of the moieties encompassed hereby:

(1) For linkage to a chelating agent having at least one —NH$_2$, —NH— or —OH functional grouping, replacing a hydrogen atom from at least one of said functional groupings with one of the following [QC+] groupings:

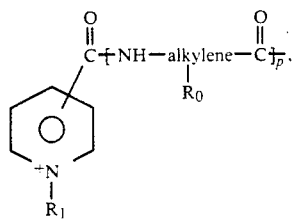
(a)

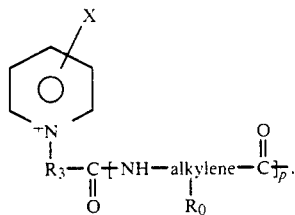
(b)

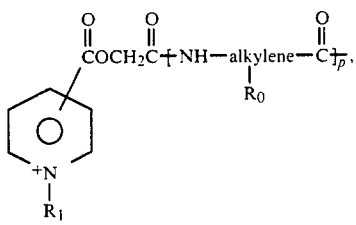
(c)

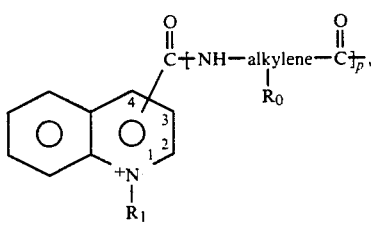
(d)

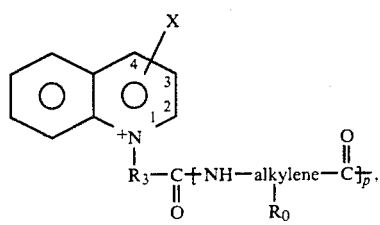
(e)

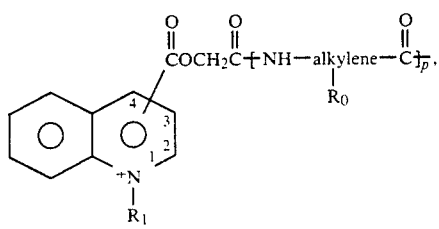
(f)

-continued

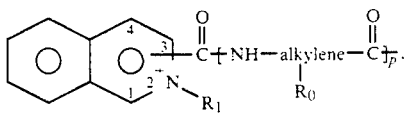
(g)

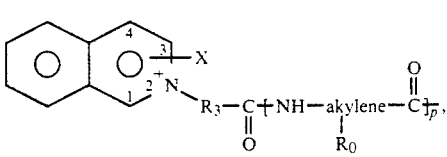
(h)

or

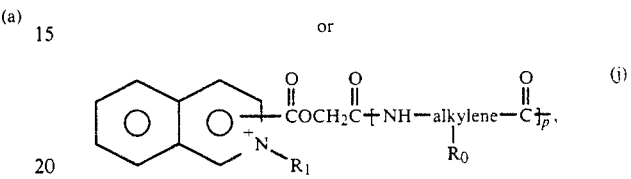
(j)

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring;

(2) For the linkage to a chelating agent having at least one —COOH functional grouping, replacing a hydrogen atom from at least one of said —COOH groupings with one of the following [QC+] groupings:

(a) When there are one or two —COOH groups to be derivatized:

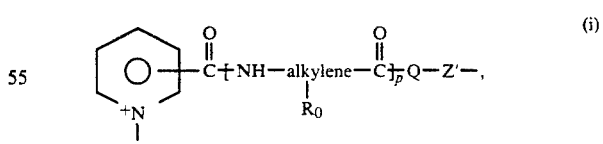
(i)

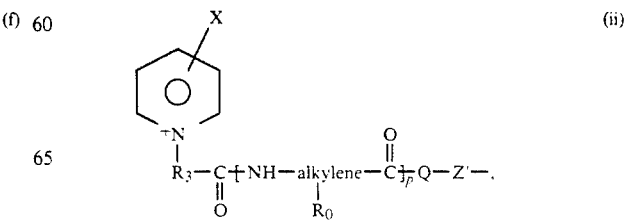
(ii)

-continued

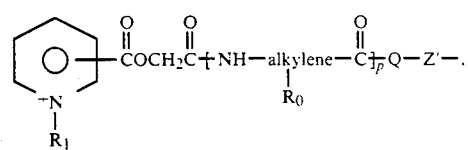  (iii)

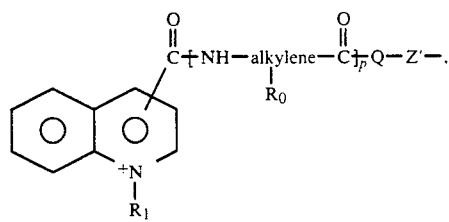  (iv)

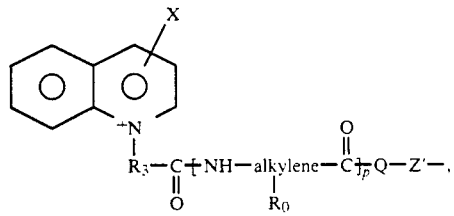  (v)

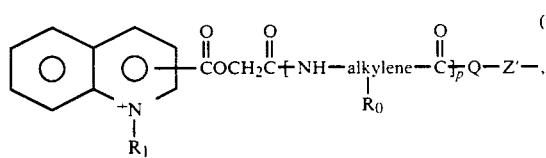  (vi)

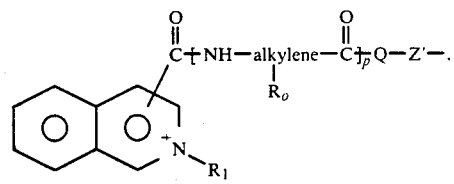  (vii)

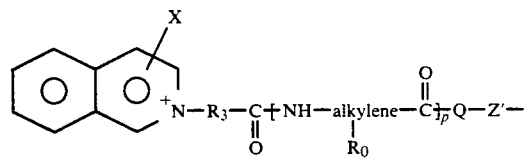  (viii)

or

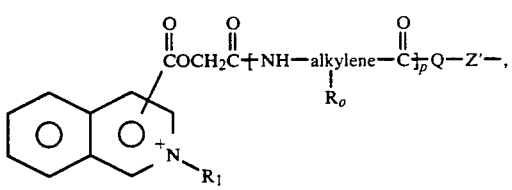  (ix)

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $Z'$ is $C_1$-$C_8$ straight or branched alkylene, preferably $C_1$-$C_3$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R'' wherein R' and R'', which can be the same or different, are each H or $C_1$-$C_7$ alkyl, or X is —CH=NOR''' wherein R''' is H or $C_1$-$C_7$ alkyl; the X substituent in formula (ii) and the carbonyl-containing groupings in formulas (i) and (iii) can each be attached at the 2, 3 or 4 position of the pyridinium ring; the X substituent in formula (v) and the carbonyl-containing groupings in formulas (iv) and (vi) can each be attached at the 2, 3 or 4 position of the quinolinium ring; and the X substituent in formula (viii) and carbonyl-containing groupings in formulas (vii) and (ix) can each be attached at the 1, 3 or 4 position of the isoquinolinium ring;

(b) Alternatively, when there is only one —COOH group to be derivatized:

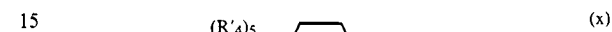  (x)

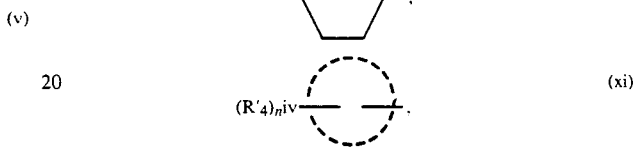  (xi)

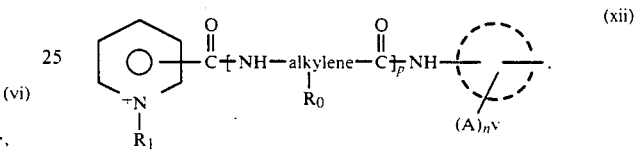  (xii)

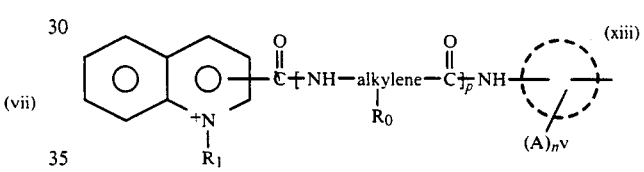  (xiii)

or

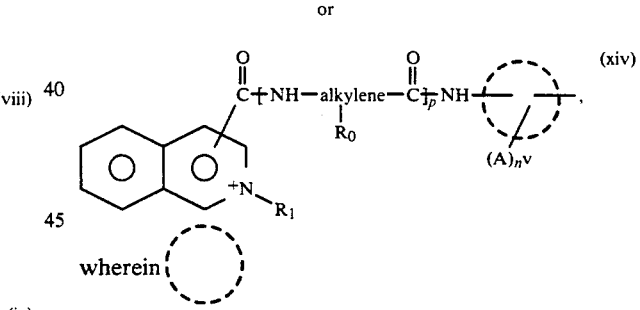  (xiv)

is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii), (xiii) and (xiv) can independently be hydroxy or D', D' being the residue of a chelating agent containing one reactive —COOH functional group, said residue being characterized by the absence of a hydrogen atom from said —COOH functional group in said chelating agent; and each $R'_4$ in each of structures (x) and (xi) can independently be hydroxy,

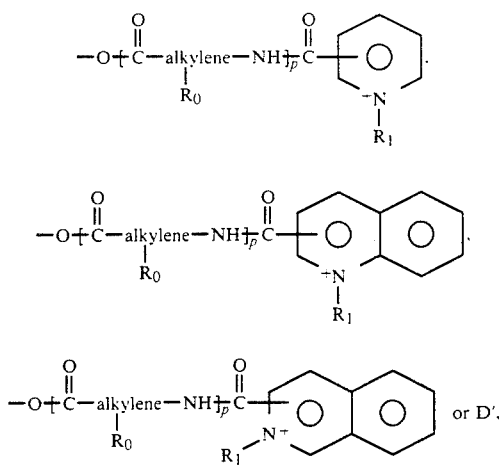

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; D' is defined as with structure (xii), (xiii) and (xiv); $R_1$ is $C_1$-$C_7$ alkyl, $C_1$-$C_7$ haloalkyl or $C_7$-$C_{10}$ aralkyl; and the depicted carbonyl-containing groupings can be attached at the 2, 3 or 4 position of the pyridinium or quinolinium ring, or at the 1, 3 or 4 position of the isoquinolinium ring; with the proviso that at least one $R'_4$ in each of structures (x) and (xi) is

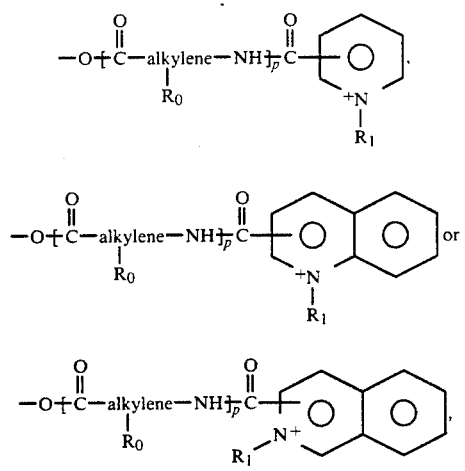

wherein alkylene, $R_o$, p and $R_1$ and the position of the carbonyl-containing groupings are defined as above; and with the further proviso that when more than one of the $R'_4$ radicals in a given compound are the aforesaid carbonyl-containing groupings, then all such carbonyl-containing groupings in said compound are identical;

(3) For linkage to a chelating agent having at least one —NH— functional group which is part of an amide or imide structure or at least one low pKa primary or secondary amine functional group, replacing a hydrogen atom from at least one of said functional groupings with one of the following [QC+] groupings:

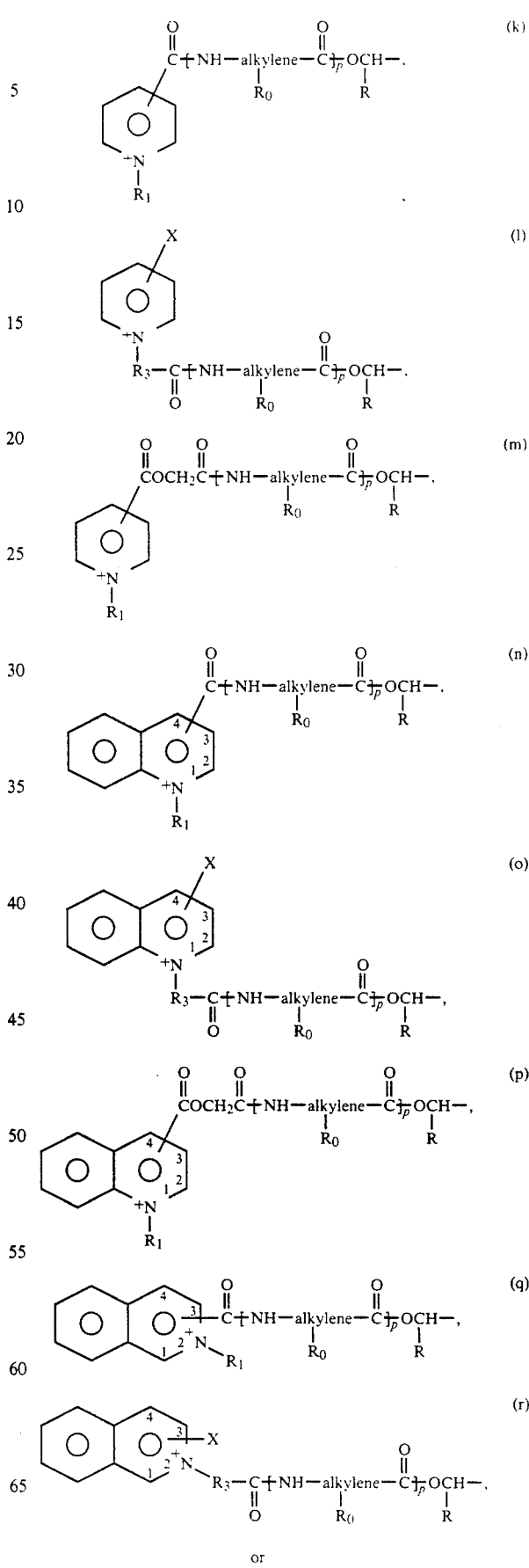

or

-continued

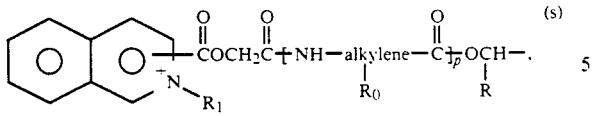

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; $R_3$ is $C_1$ to $C_3$ alkylene; X is —CONR'R'' wherein R' and R'', which can be the same or different, are each H or $C_1$-$C_7$ alkyl, or X is —CH=NOR''' wherein R''' is H or $C_1$-$C_7$ alkyl; the carbonyl-containing groupings in formulas (k) and (m) and the X substituent in formula (1) can each be attached at the 2, 3 or 4 position of the pyridinium ring; the carbonyl containing groupings in formulas (n) and (p) and the X substituent in formula (o) can each be attached at the 2, 3 or 4 position of the quinolinium ring; and the carbonyl-containing groupings in formulas (q) and (s) and the X substituent in formula (r) can each be attached at the 1, 3 or 4 position of the isoquinolinium ring.

Here and throughout this application, the expression "$C_1$-$C_7$ haloalkyl" means $C_1$-$C_7$ alkyl substituted by one or more halogen atoms. Also here and throughout this application, the alkyl radicals, including alkyl and alkylene portions of other radicals, can be straight or branched unless otherwise specified.

The expression "$R_o$ is a radical identical to the corresponding portion of a natural amino acid" is believed to be self-explanatory. Thus, for example, $R_o$ can be hydrogen, as in glycine; methyl, as in alanine; —CH(CH$_3$)$_2$, as in valine; —CH$_2$—CH(CH$_3$)$_2$, as in leucine;

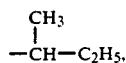

as in isoleucine;

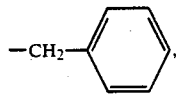

as in phenylalanine;

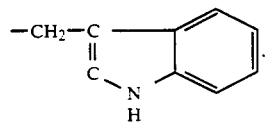

as in tryptophan; —CH$_2$OH, as in serine; —CHOH—CH$_3$, as in threonine; —(CH$_2$)$_2$—SCH$_3$, as in methionine; —CH$_2$—CONH$_2$, as in asparagine; —CH$_2$CH$_2$—CONH$_2$, as in glutamine;

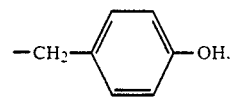

as in tyrosine; —CH$_2$SH, as in cysteine; —CH$_2$COOH, as in aspartic acid; and —CH$_2$CH$_2$COOH, as in glutamic acid. The expression "natural amino acid" as used herein does not encompass dopa or L-DOPA. Preferred amino acids encompassed by the $R_o$ term include glycine, alanine, valine, leucine, phenylalanine, isoleucine, methionine, asparagine and glutamine.

The dihydro forms [DHC] corresponding to the aforementioned quaternaries are as follows:

(1') For Group (1) above:

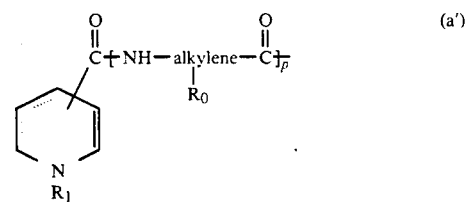
(a')

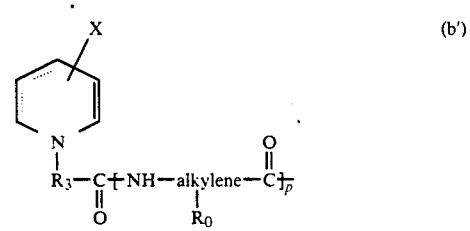
(b')

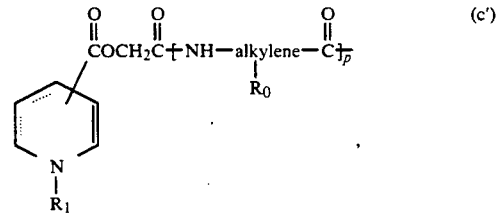
(c')

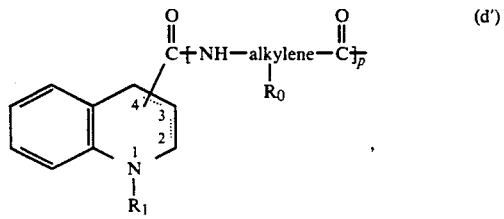
(d')

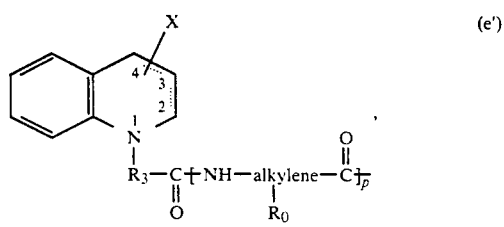
(e')

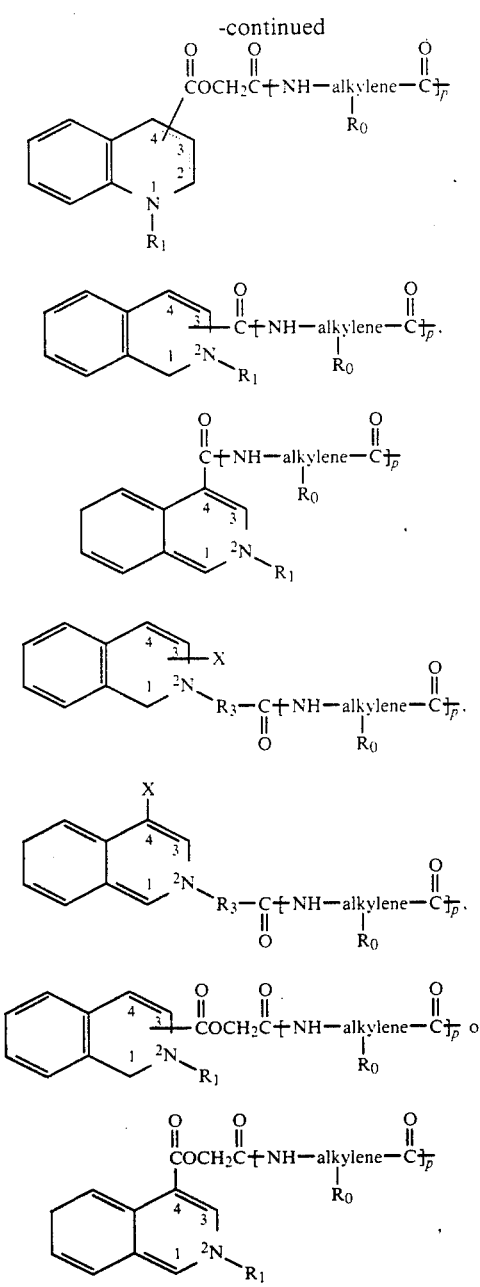

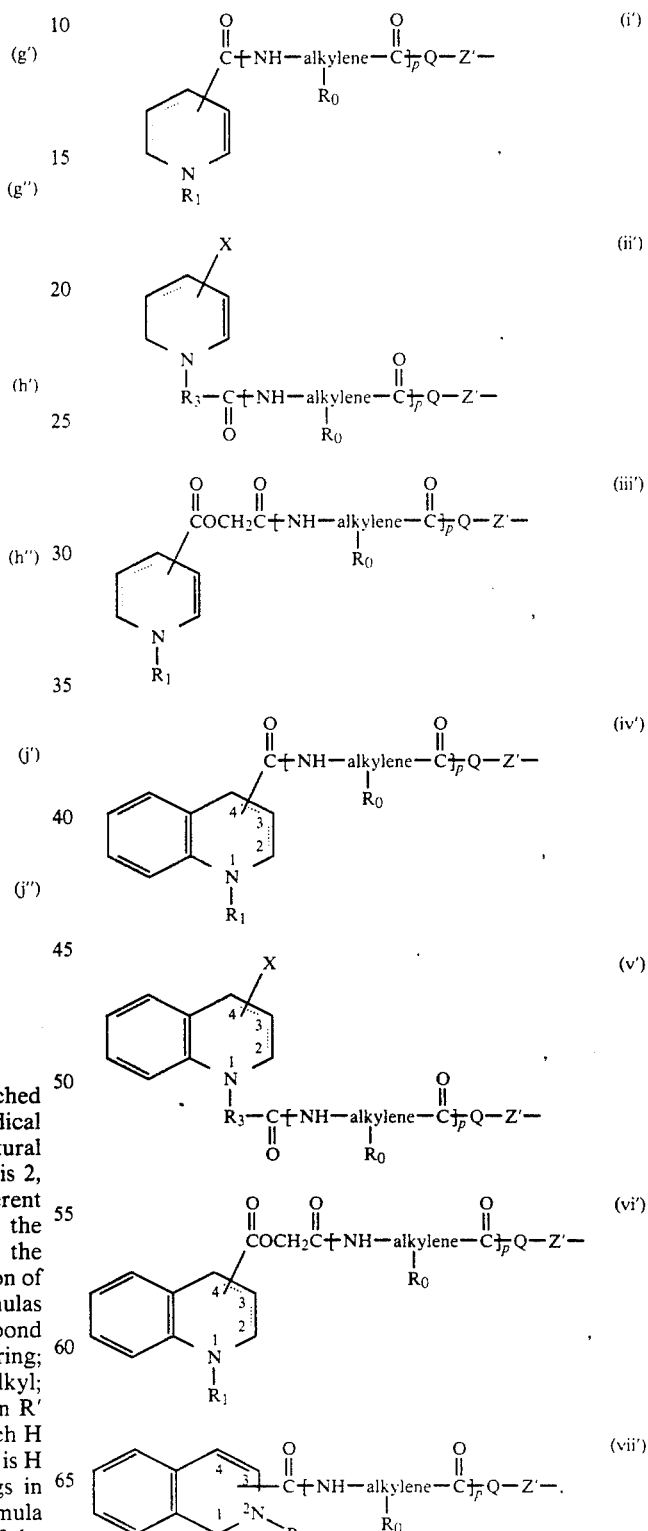

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring;

(2') For Group (2) (a) above:

-continued

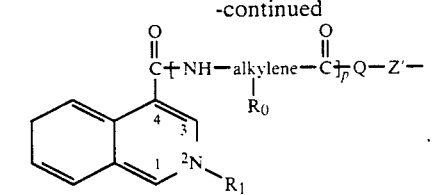
(vii")

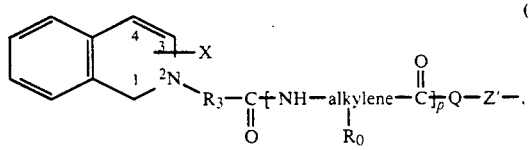
(viii')

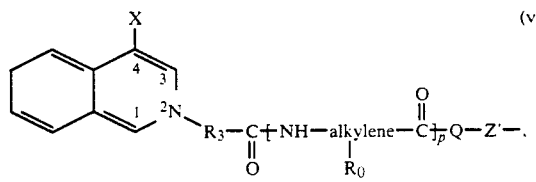
(viii")

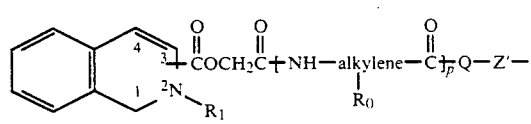
(ix')

or

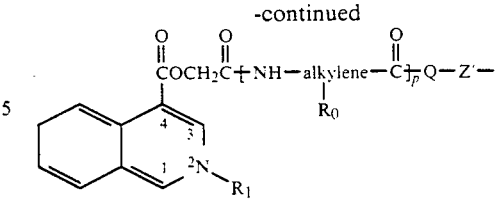
(ix")

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (i'), (i") and (iii') indicates the presence of a double bond in either the 4 or 5 position of the dihydropyridine ring; the dotted line in formulas (iv'), (v') and (vi') indicates the presence of a double bond in either the 2 or 3 position of the dihydroquinoline ring; Z' is $C_1$-$C_8$ straight or branched alkylene, preferably $C_1$-$C_3$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the X substituent in formula (ii') and the carbonyl-containing grouping in formulas (i') and (iii') can each be attached at the 2, 3 or 4 position of the dihydropyridine ring; the X substituent in formula (v') and the carbonyl-containing grouping in formulas (iv') and (vi') can each be attached at the 2, 3 or 4 position of the dihydroquinoline ring; and the X substituent in formula (viii') and the carbonyl-containing groupings in formulas (vii') and (ix') can each be attached at the 1, 3 or 4 position of the dihydroisoquinoline ring;

(3') For Group (2) (b) above:

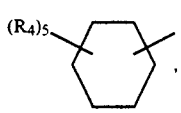
(x')

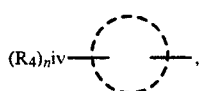
(xi')

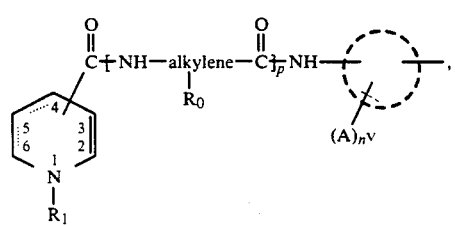
(xii')

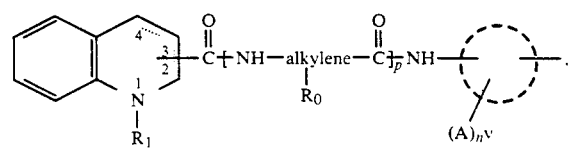
(xiii')

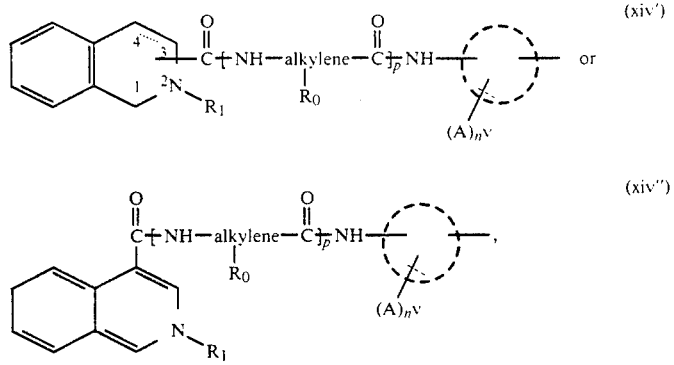

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formula (xii') indicates the presence of a double bond in either the 4 or 5 position of the dihydropyridine ring; the dotted line in formula (xiii') indicates the presence of a double bond in either the 2 or 3 position of the dihydroquinoline ring;

is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii'), (xiii'), (xiv') and (xiv'') can independently be hydroxy or D', D' being the residue of a chelating agent containing one reactive —COOH functional group, said residue being characterized by the absence of a hydrogen atom from said —COOH functional group in said chelating agent; and each $R_4$ in each of structures (x') and (xi') can independently be hydroxy,

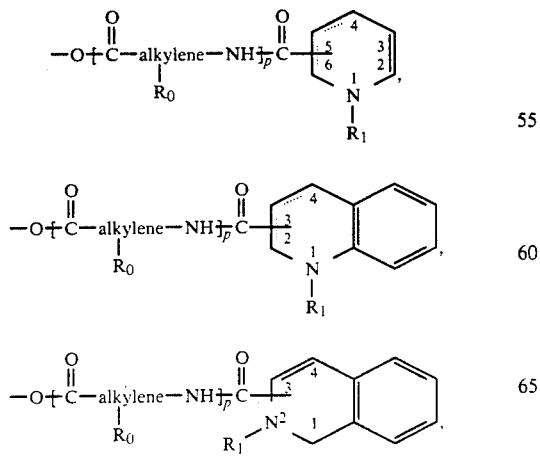

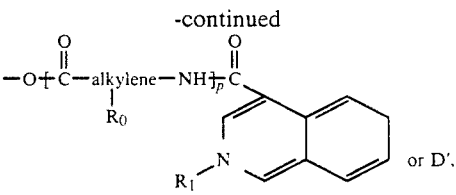

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line is defined as with structures (xii') and (xiii'); D' is defined as with structures (xii'), (xiii'), (xiv') and (xiv''); $R_1$ is $C_1$-$C_7$ alkyl, $C_1$-$C_7$ haloalkyl or $C_7$-$C_{10}$ aralkyl; and the depicted carbonyl groupings can be attached at the 2, 3 or 4 position of the pyridinium or quinolinium ring or, except where otherwise specified, at the 1, 3 or 4 position of the isoquinolinium ring; with the proviso that at least one $R_4$ in each of structures (x') and (xi') is

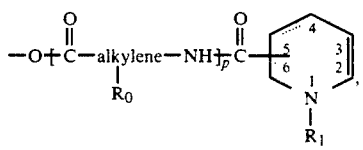

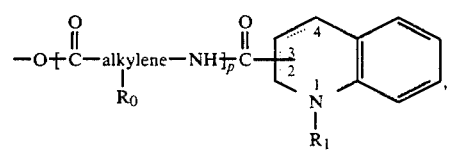

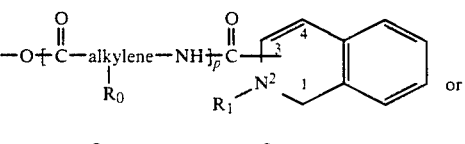

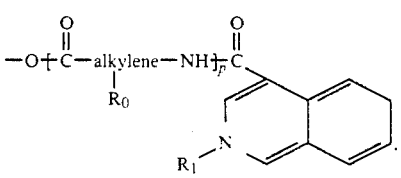

wherein alkylene, $R_o$, p, $R_1$, the dotted lines and the position of the carbonyl-containing groupings are defined as above; and with the further proviso that when more than one of the $R_4$ radicals in a given compound are the aforesaid carbonyl-containing groupings, then all such carbonyl-containing groupings in said compound are identical;

(4') For Group (3) above:

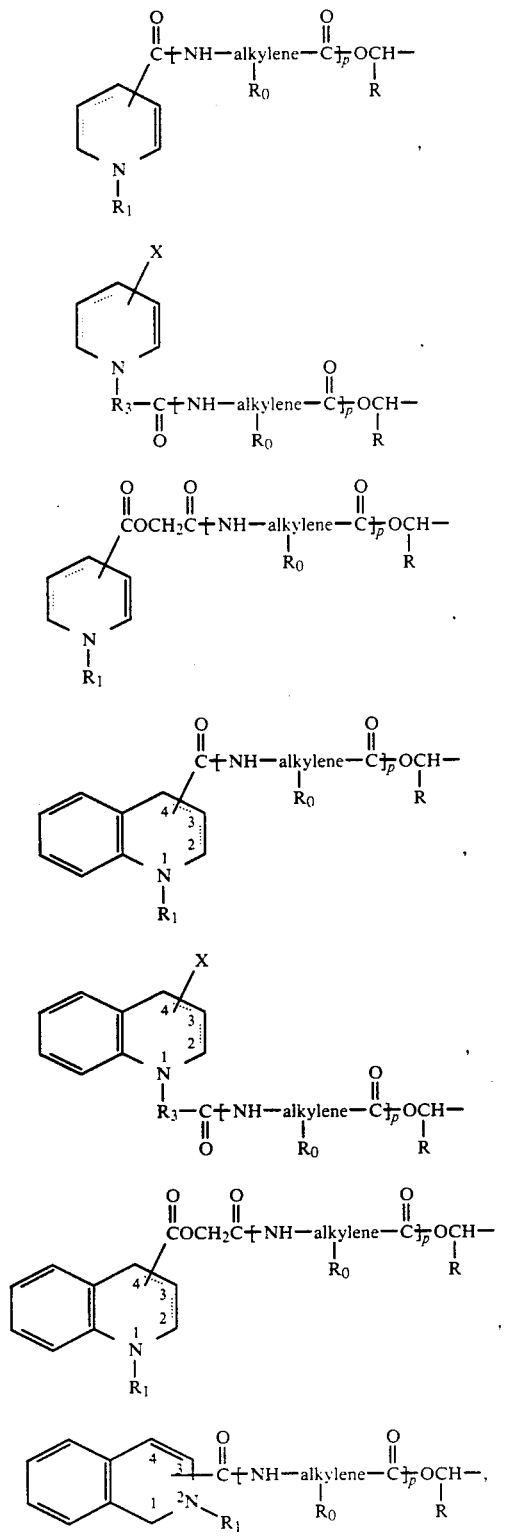

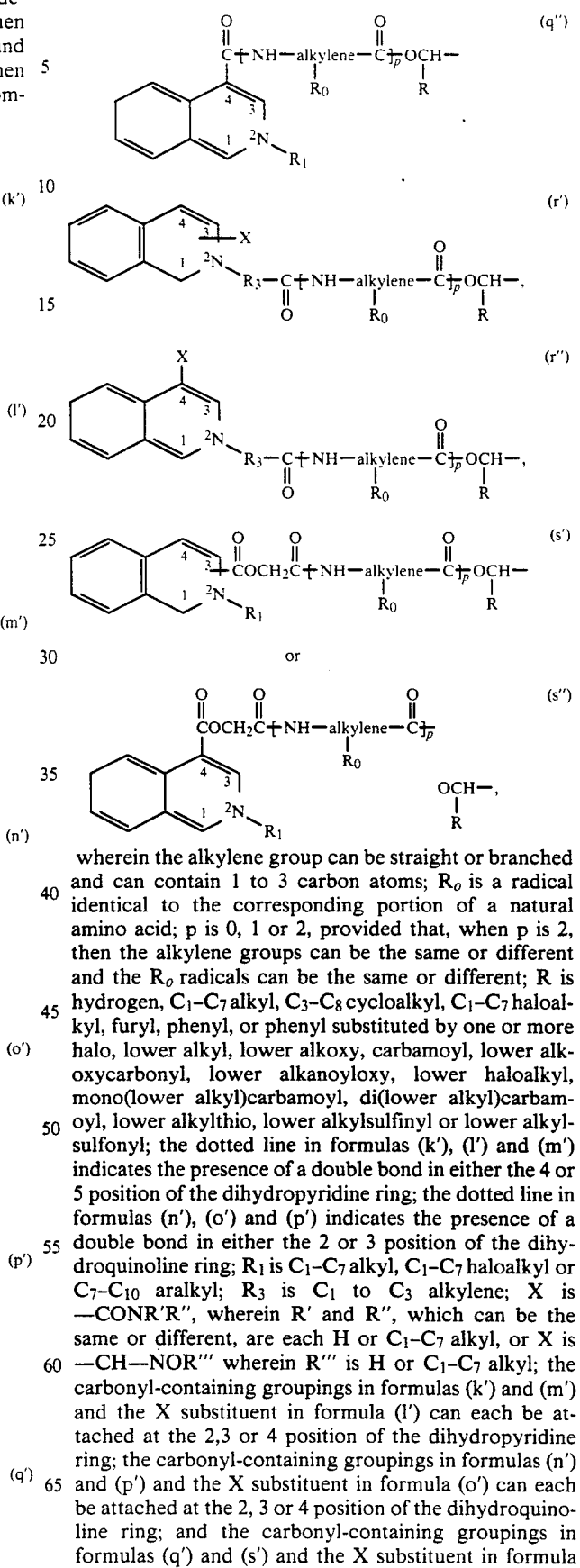

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; the dotted line in formulas (k'), (l') and (m') indicates the presence of a double bond in either the 4 or 5 position of the dihydropyridine ring; the dotted line in formulas (n'), (o') and (p') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R'', wherein R' and R'', which can be the same or different, are each H or $C_1$-$C_7$ alkyl, or X is —CH—NOR''' wherein R''' is H or $C_1$-$C_7$ alkyl; the carbonyl-containing groupings in formulas (k') and (m') and the X substituent in formula (l') can each be attached at the 2,3 or 4 position of the dihydropyridine ring; the carbonyl-containing groupings in formulas (n') and (p') and the X substituent in formula (o') can each be attached at the 2, 3 or 4 position of the dihydroquinoline ring; and the carbonyl-containing groupings in formulas (q') and (s') and the X substituent in formula (r') can each be attached at the 1, 3 or 4 position of the dihydroisoquinoline ring.

The presently preferred dihydropyridine⇌pyridinium salt redox carrier moieties of this invention are those wherein p is 0 or 1, most preferably 0; alkylene, when present (i.e. p=1 or 2), is —$CH_2$—; $R_o$, when present (i.e. p=1 or 2), is H, —$CH_3$, —$CH(CH_3)_2$,

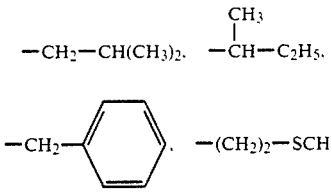

—$CH_2$—$CONH_2$ or —$CH_2CH_2$—$CONH_2$; $R_1$, when present, is —$CH_3$; $R_3$, when present, is —$CH_2CH_2$—; X, when present, is —$CONH_2$; the depicted carbonyl-containing groupings in formulas (a) and (c) and the X substituent in formula (b) are attached at the 3-position; the depicted carbonyl-containing groupings in formulas (d) and (f) and the X substituent in formula (e) are attached at the 3-position; the depicted carbonyl-containing groupings in formulas (g) and (j) and the X substituent in formula (h) are attached at the 4-position; Z', when present, is $C_2$ or $C_3$ straight or branched alkylene; Q, when present, is —NH—; the X substituent in formulas (ii) and (v) and the depicted carbonyl-containing groupings in formulas (i), (iii), (iv) and (vi) are attached at the 3-position; the X substituent in formula (viii) and the depicted carbonyl-containing groupings in formulas (vii) and (ix) are attached at the 4-position; and the depicted carbonyl-containing groupings encompassed by formulas (x), (xi), (xii), (xiii) and (xiv) are in the 3-position of the pyridinium or quinolinium ring and in the 4-position of the isoquinolinium ring; all $R'_4$'s in structures (x) and (xi) are —OH except for the one $R_4$ in each structure which must be the carrier moiety; all A's in structures (xii), (xiii) and (xiv) are —OH;  is the skeleton of a glucose molecule; R in formulas (k), (l) and (m) is hydrogen, methyl or $CCl_3$; and the depicted carbonyl-containing groupings in formulas (k) through (s) are in the 3-position of the pyridinium or quinolinium ring and in the 4-position of the isoquinolinium ring; and the corresponding dihydro moieties.

Especially preferred dihydropyridine⇌pyridinium salt redox carrier moieties are the quaternaries of Group (1), structures (a), (b), (d), (e), (g) and (h); those of Group (2), structures (i), (ii), (iv), (v), (vii), (viii), (x) and (xii); and those of Group 3, structures (k), (l), (n), (o), (q) and (r); and the corresponding dihydro forms, most especially when they contain the preferred structural variables identified in the preceding paragraph.

The following synthetic schemes illustrate various approaches to the preparation of the carrier-containing chelating agent precursors of formula (I), to the corresponding carrier-containing chelating agents of formula (II) and to the corresponding carrier-containing radiopharmaceuticals of formula (III). Also shown are the corresponding "locked in" quaternaries of formula (IV) formed by in vivo oxidation of the formula (III) chelates, said formula (IV) quaternaries being the primary localized materials whose radionuclide content is imaged by radiation detection means.

SCHEME 1

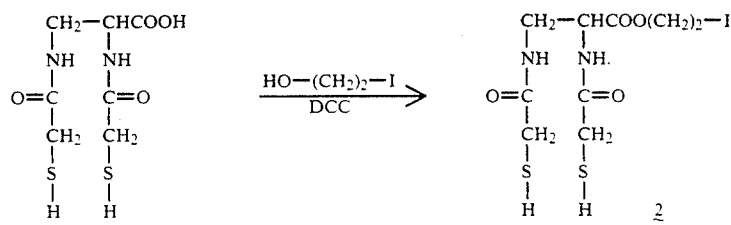

-continued
SCHEME 1
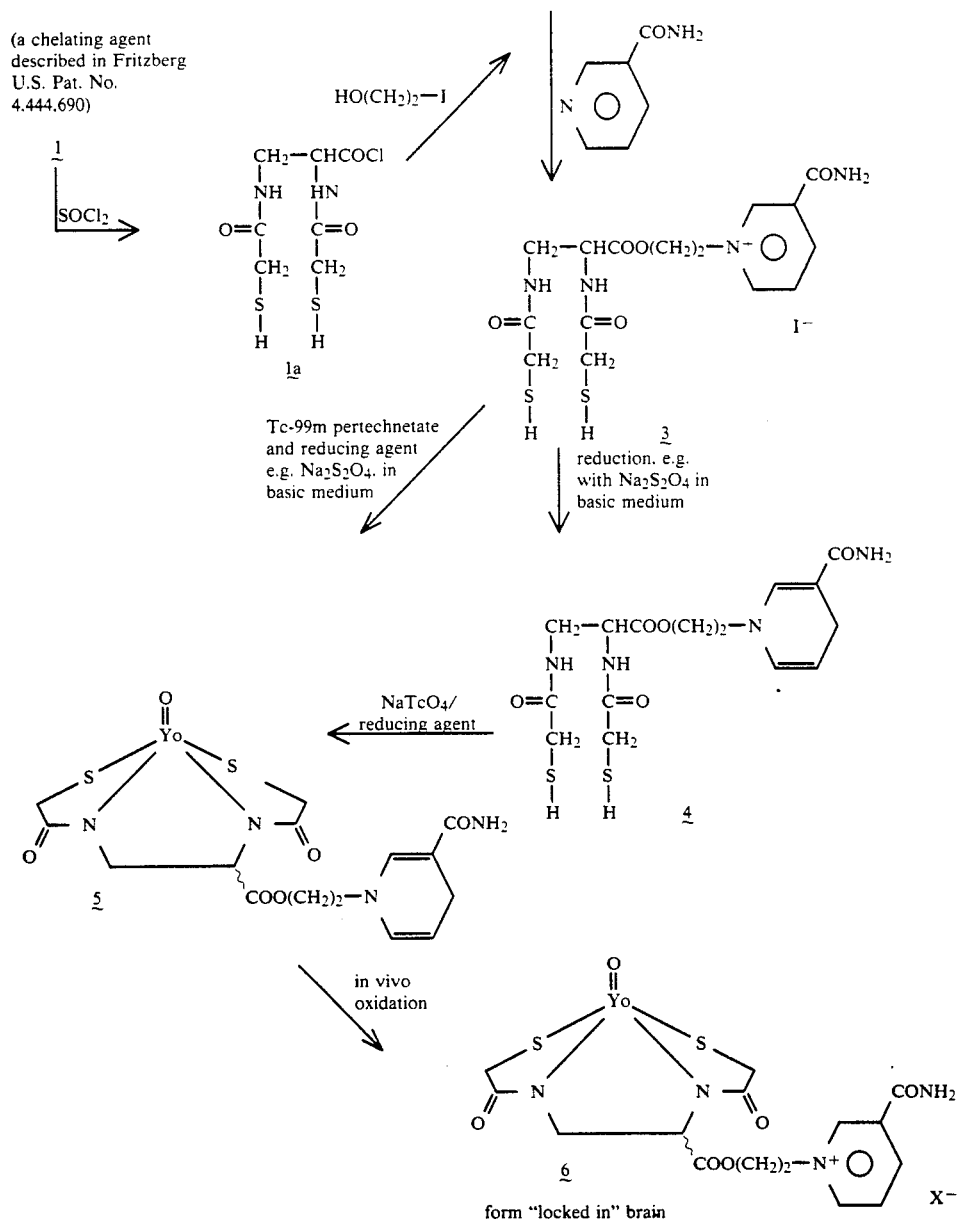
SCHEME 2
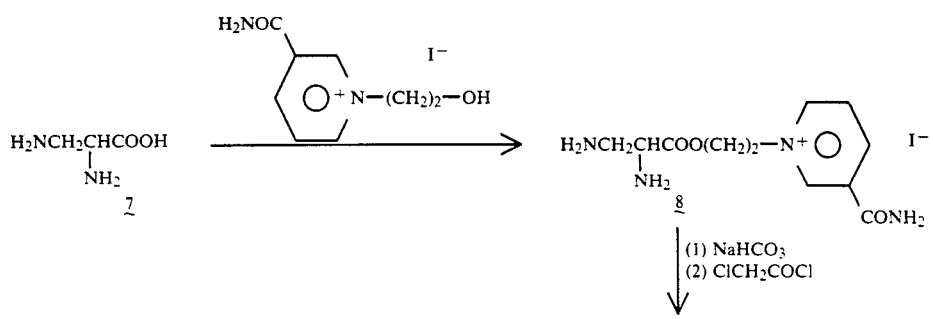

-continued
SCHEME 2
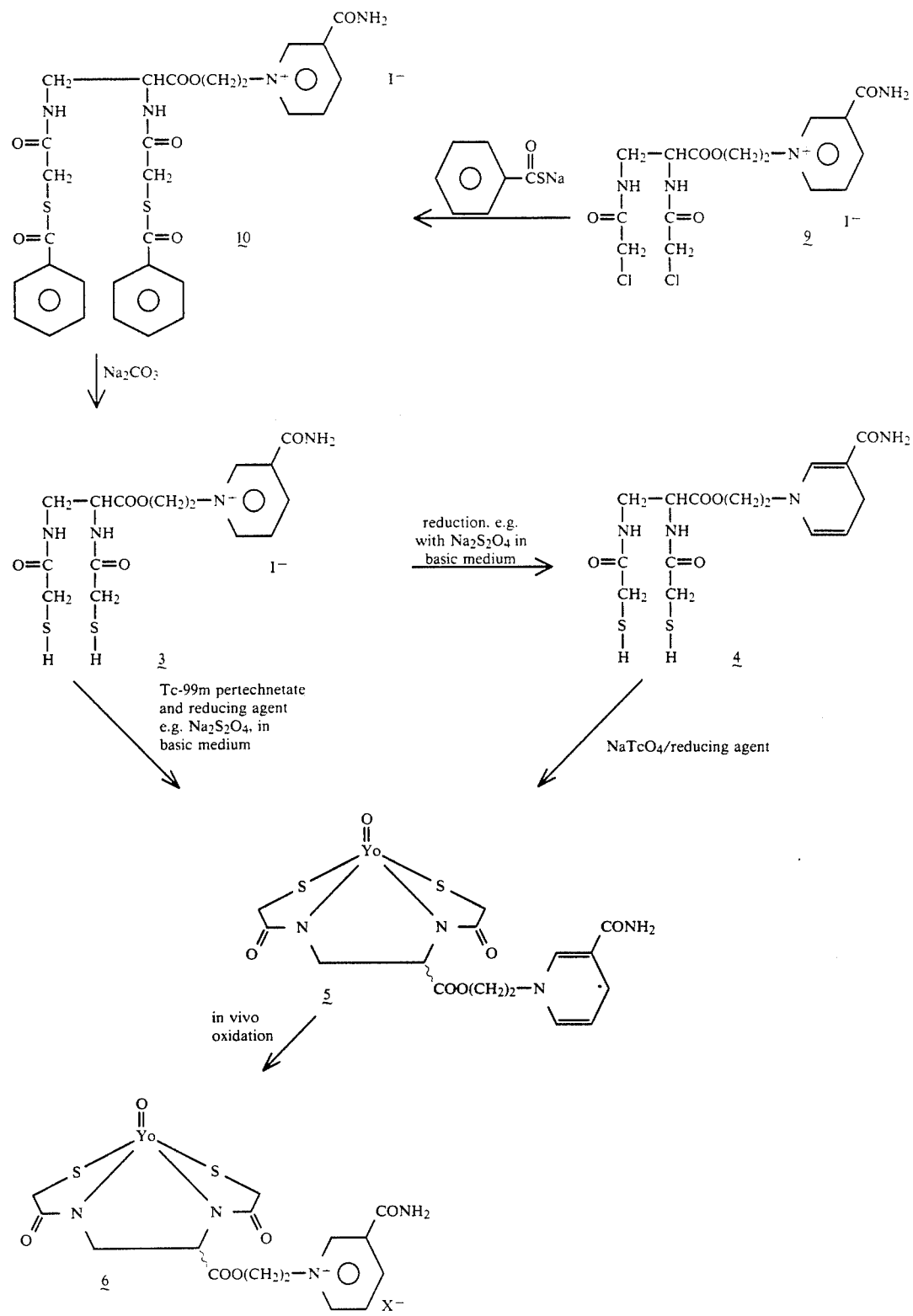
form "locked in" brain

SCHEME 3
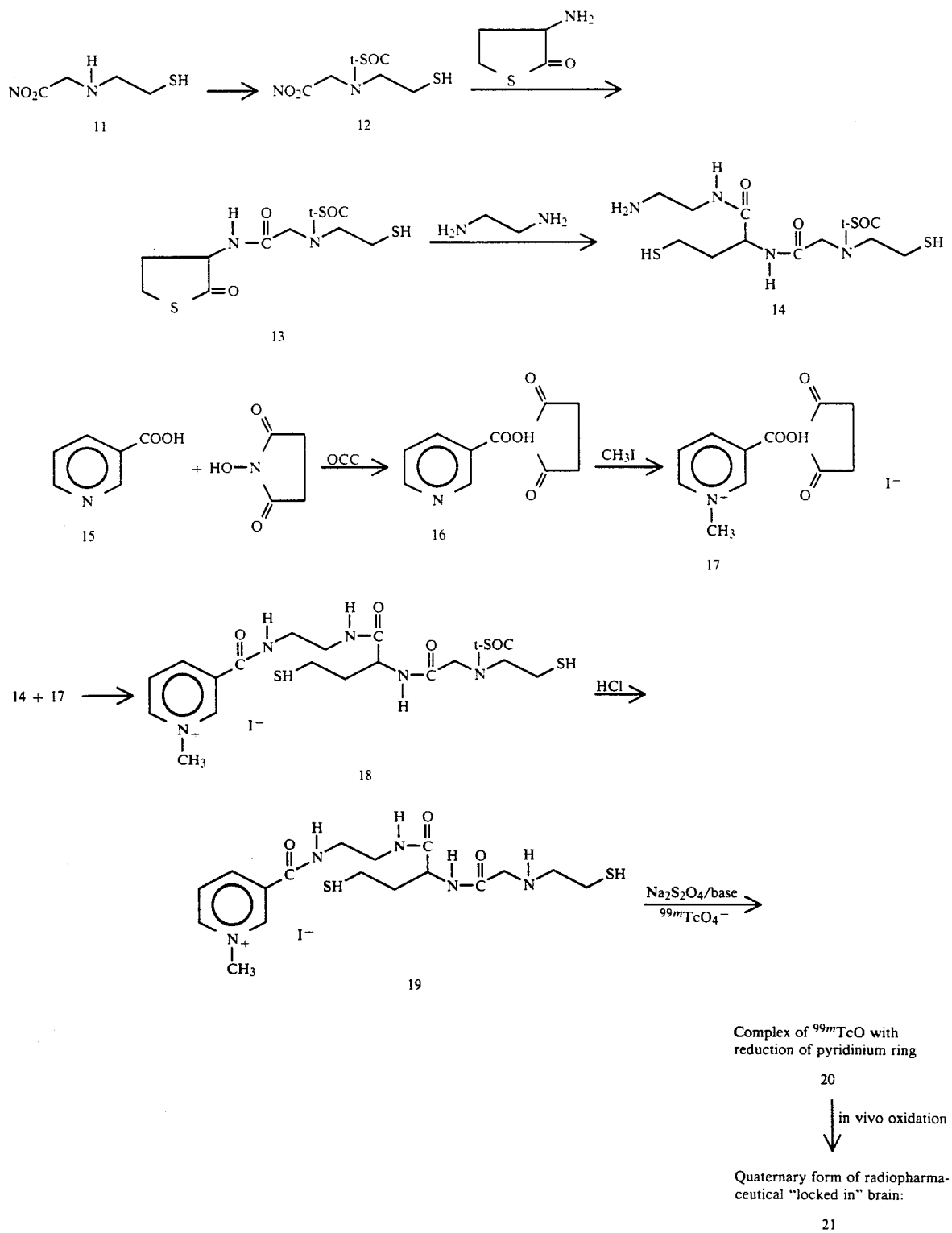
Complex of $^{99m}$TcO with reduction of pyridinium ring
20
↓ in vivo oxidation
Quaternary form of radiopharmaceutical "locked in" brain:
21

SCHEME 4
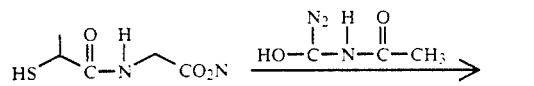
22
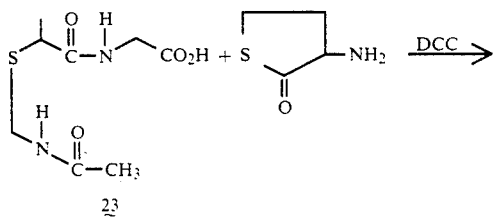
23
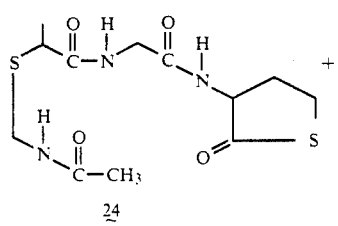
24
$H_2N\text{—}CH_2CH_2\text{—}NH_2 \longrightarrow$
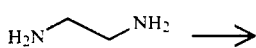
25
-continued
SCHEME 4
25 + 17 →
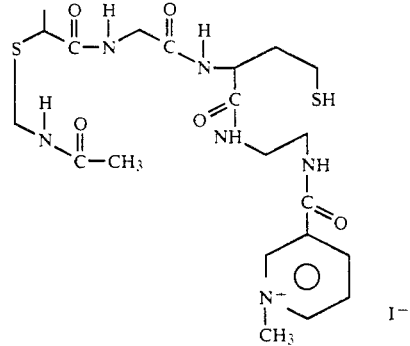
26
$26 + {}^{99m}TcO_4{}^- \xrightarrow[OH^-]{Na_2S_2O_4}$ Complex with reduction of pyridinium ring
27
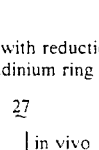in vivo oxidation
Quaternary form of radiopharmaceutical "locked in" brain
28
SCHEME 5
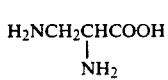 $\xrightarrow[HCl]{C_2H_5OH}$ 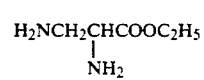
7                             30
↓ reduction (e.g. with LiAlH₄)
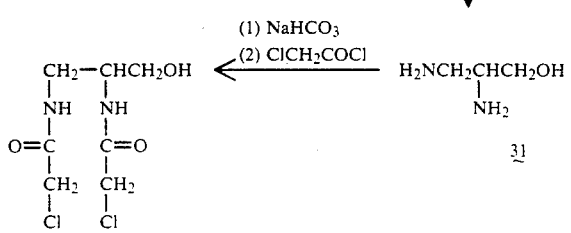
$\xleftarrow[\text{(2) ClCH}_2\text{COCl}]{\text{(1) NaHCO}_3}$ $H_2NCH_2CHCH_2OH$
                                          NH₂
31
32

-continued
SCHEME 5
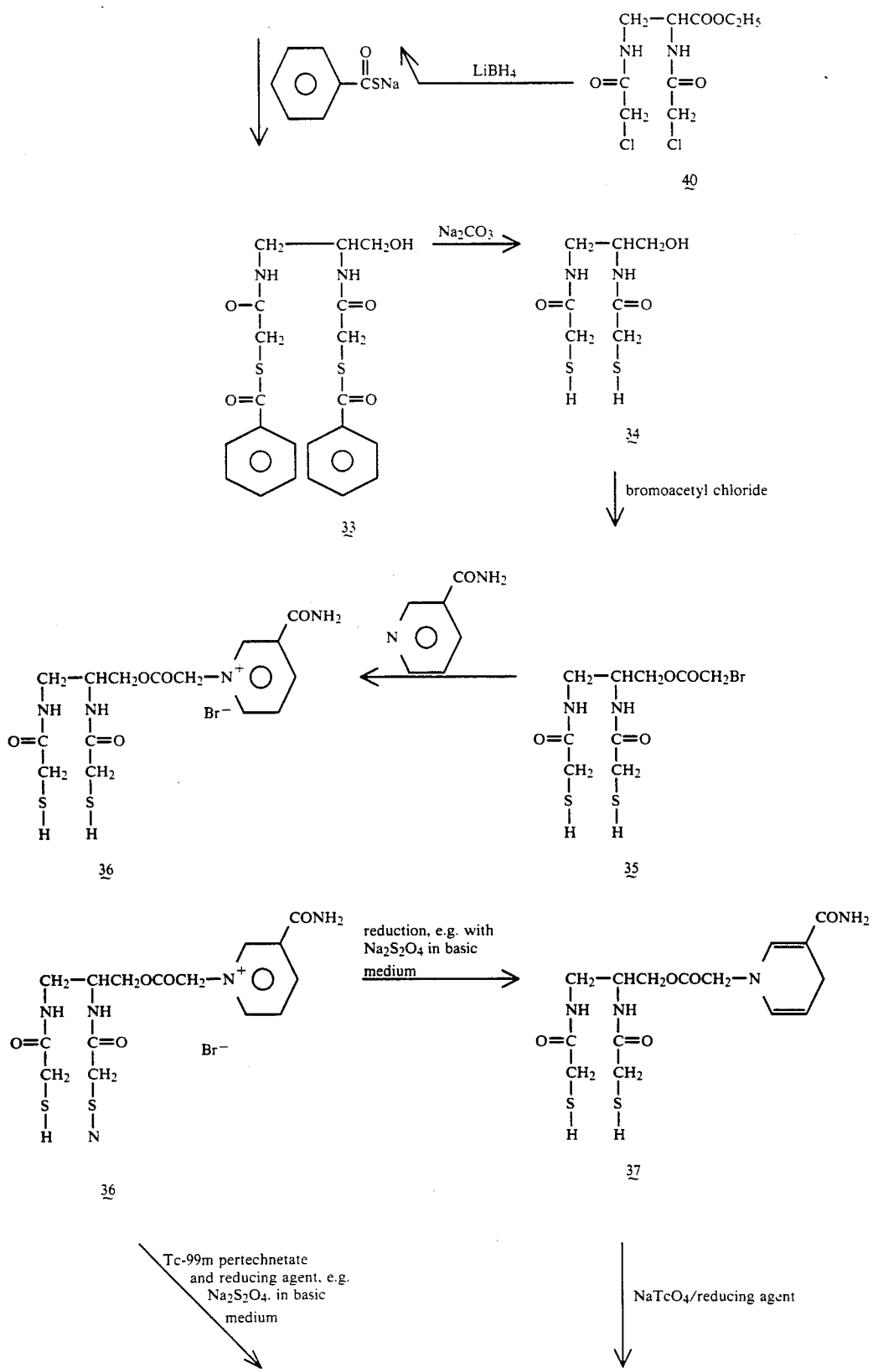

-continued
SCHEME 5
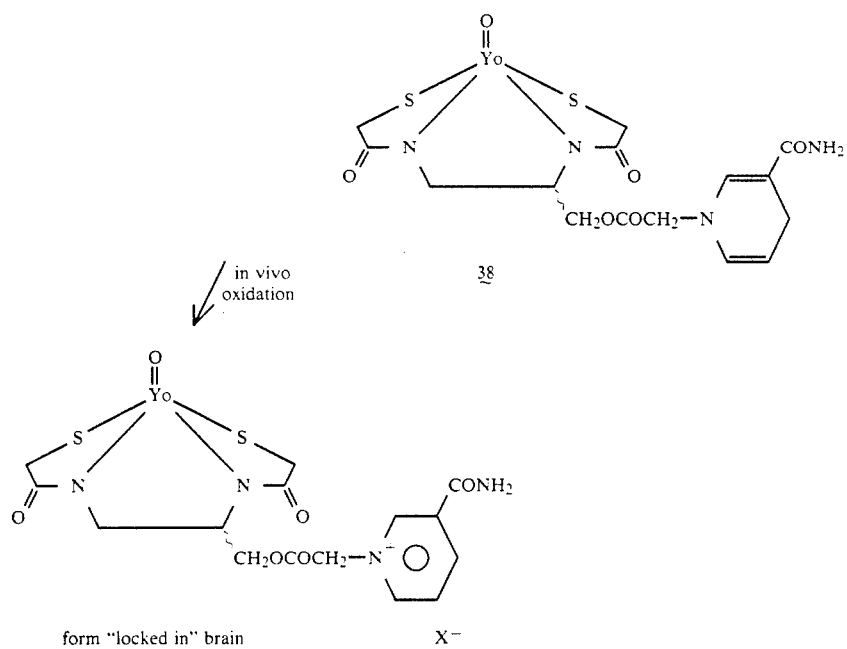
form "locked in" brain
SCHEME 6
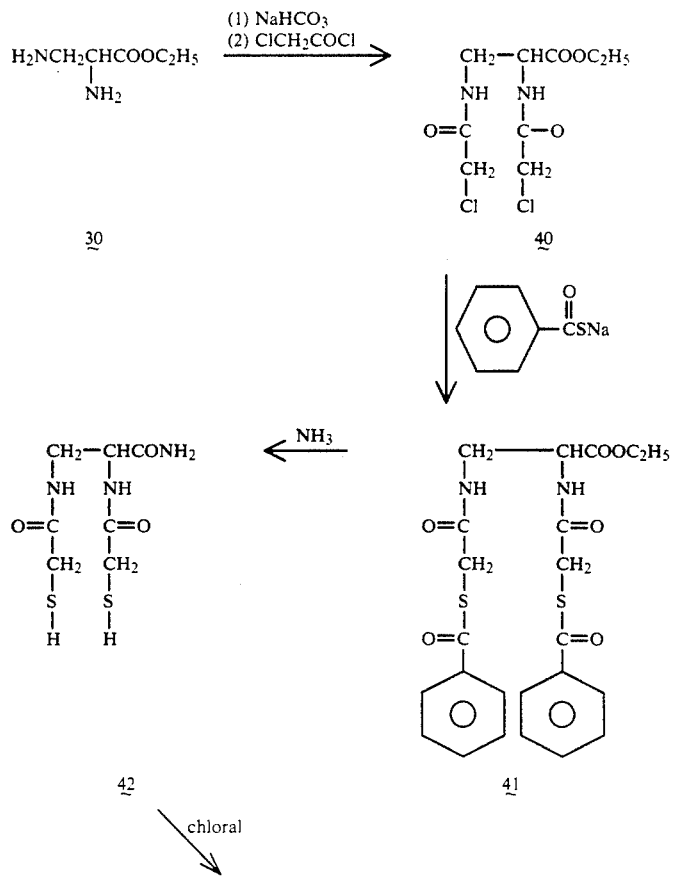

-continued
SCHEME 6
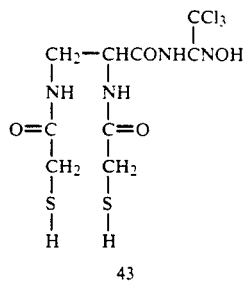
43
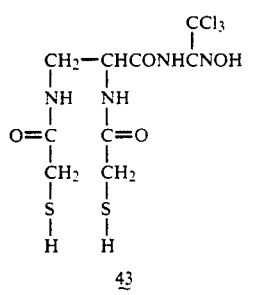 →nicotinic acid DCC→ 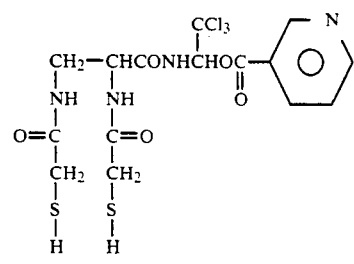
43                                                                                     44
↓ CH₃I
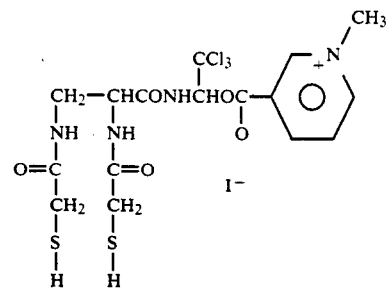
45
Tc-99m pertechnetate and reducing agent, e.g. Na₂S₂O₄, basic medium ↙          ↓ reduction, e.g. with Na₂S₂O₄ in basic medium
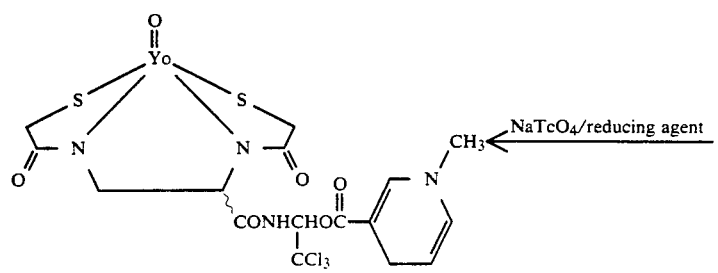 ←NaTcO₄/reducing agent← 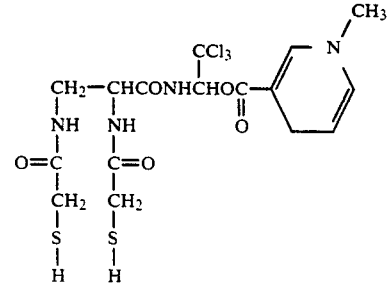
47                                                                                        46
↙ in vivo oxidation
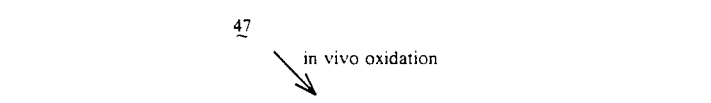

-continued
SCHEME 6
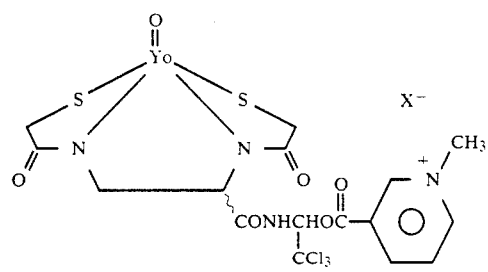
48
form "locked in" brain
SCHEME 7
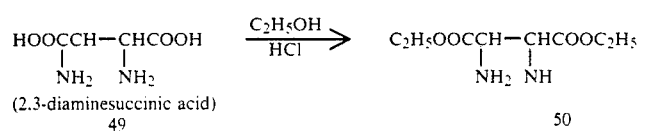
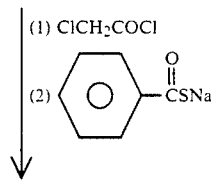
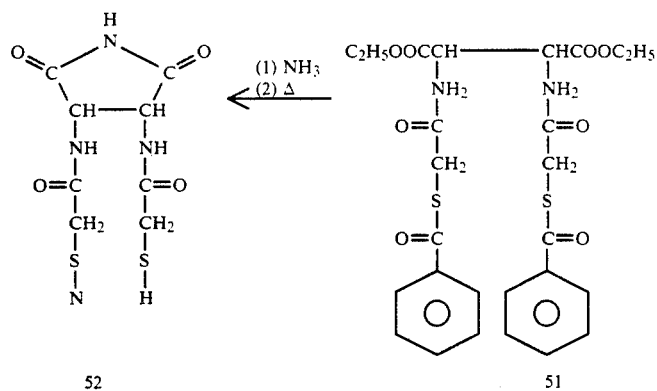
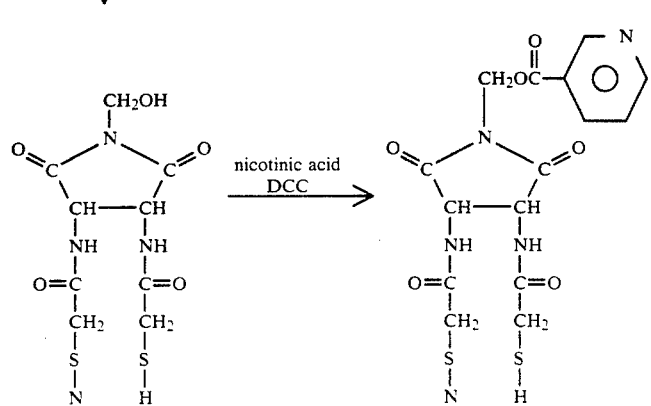

5,155,227
-continued
SCHEME 7
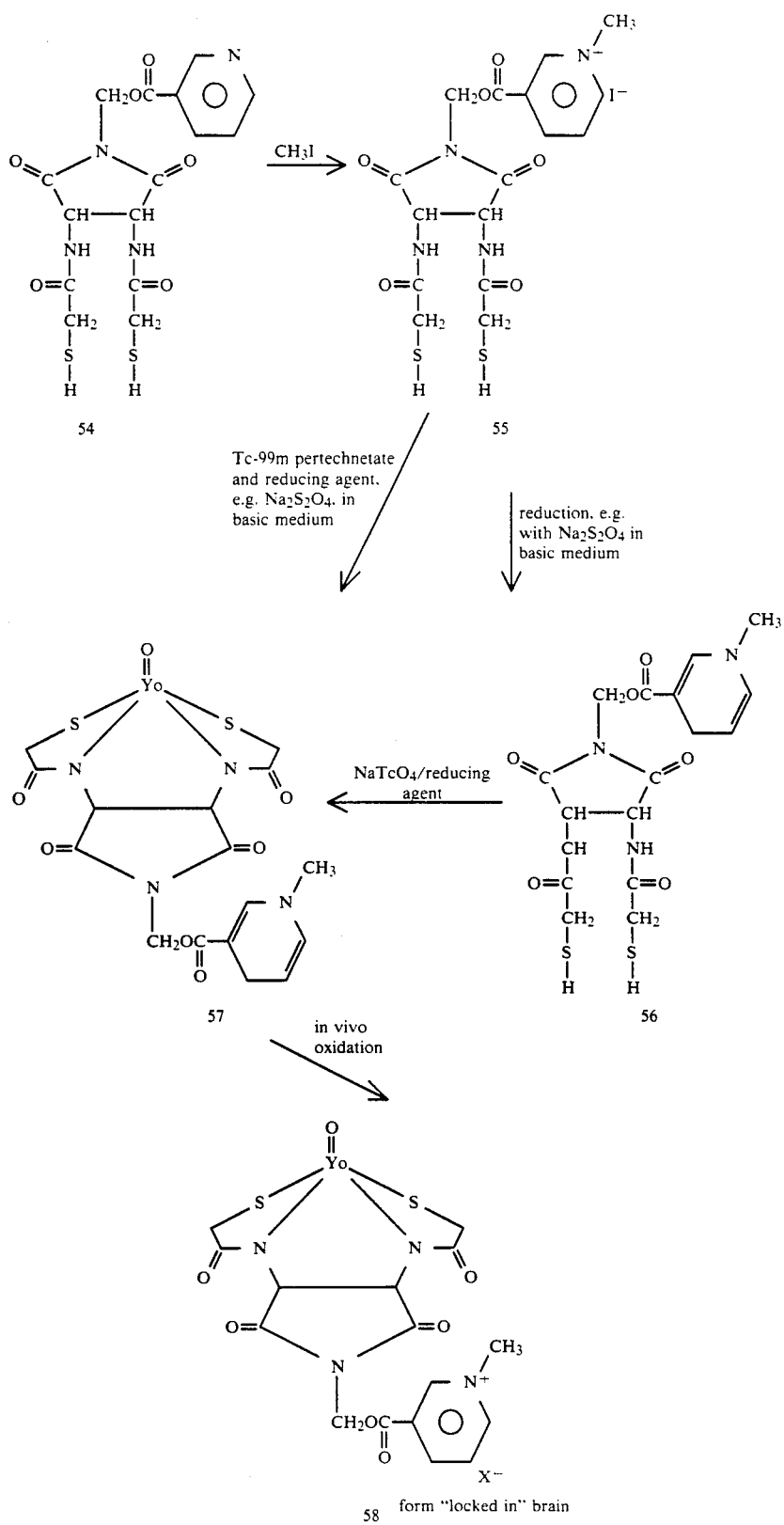
58 form "locked in" brain

SCHEME 8
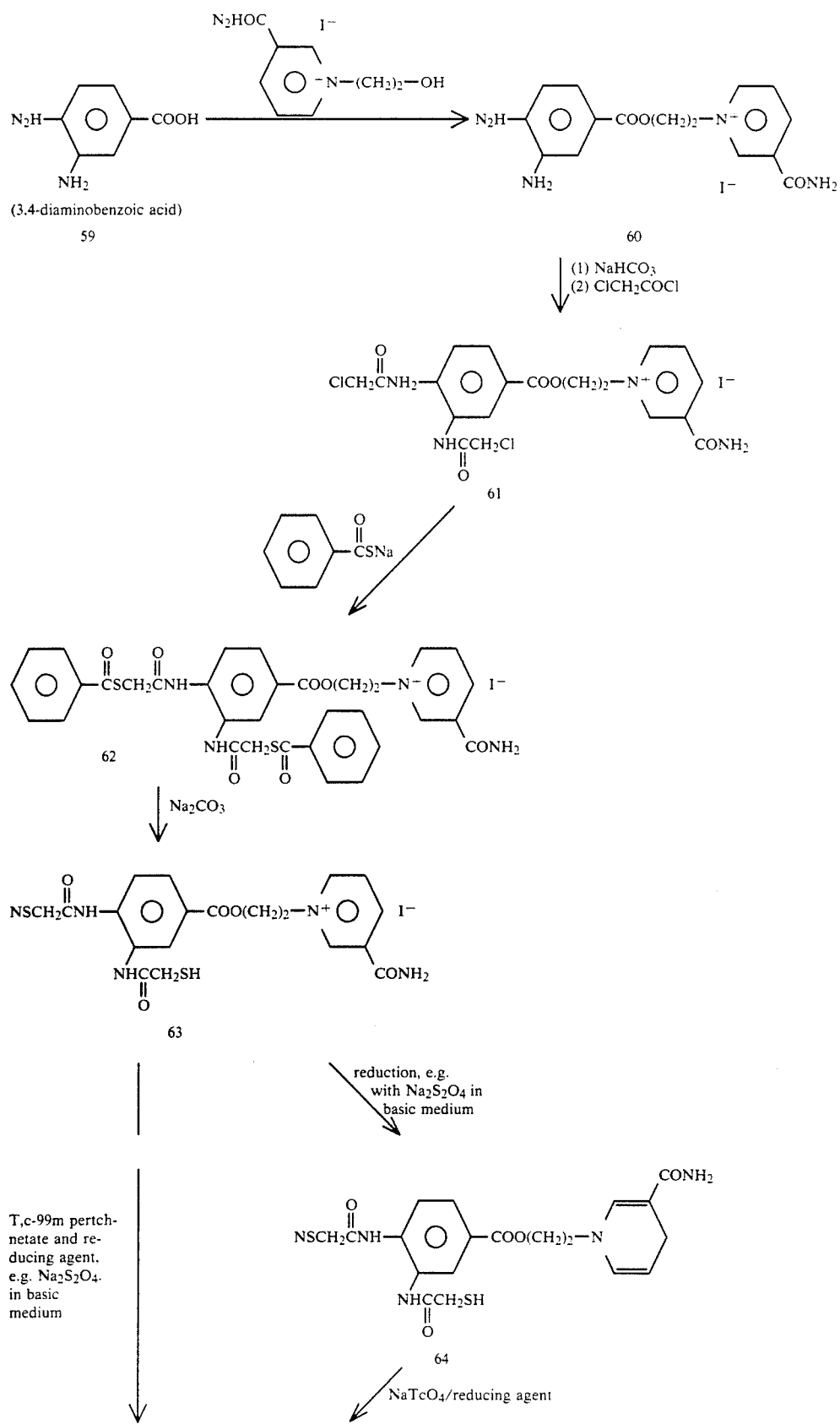

49 50
-continued
SCHEME 8
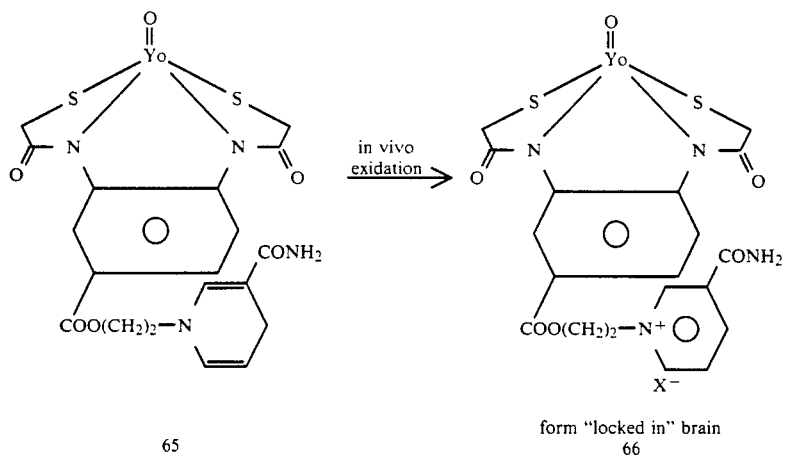
form "locked in" brain
65          66
SCHEME 9
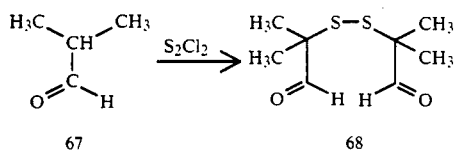
67          68
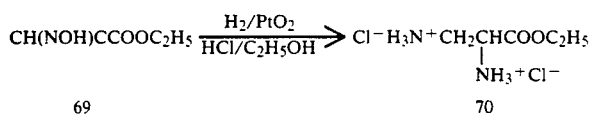
69          70
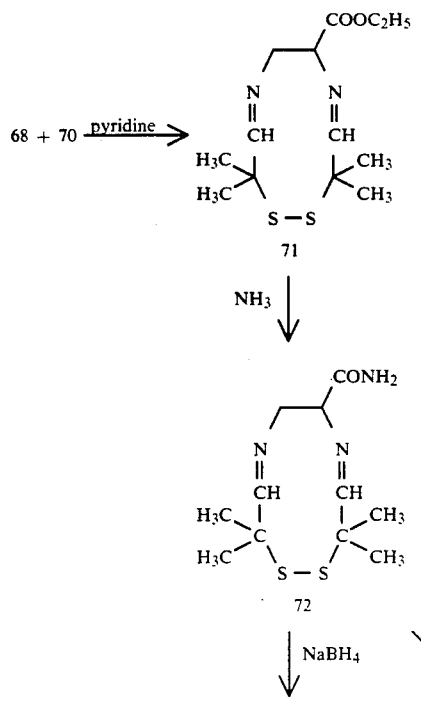

-continued
SCHEME 9
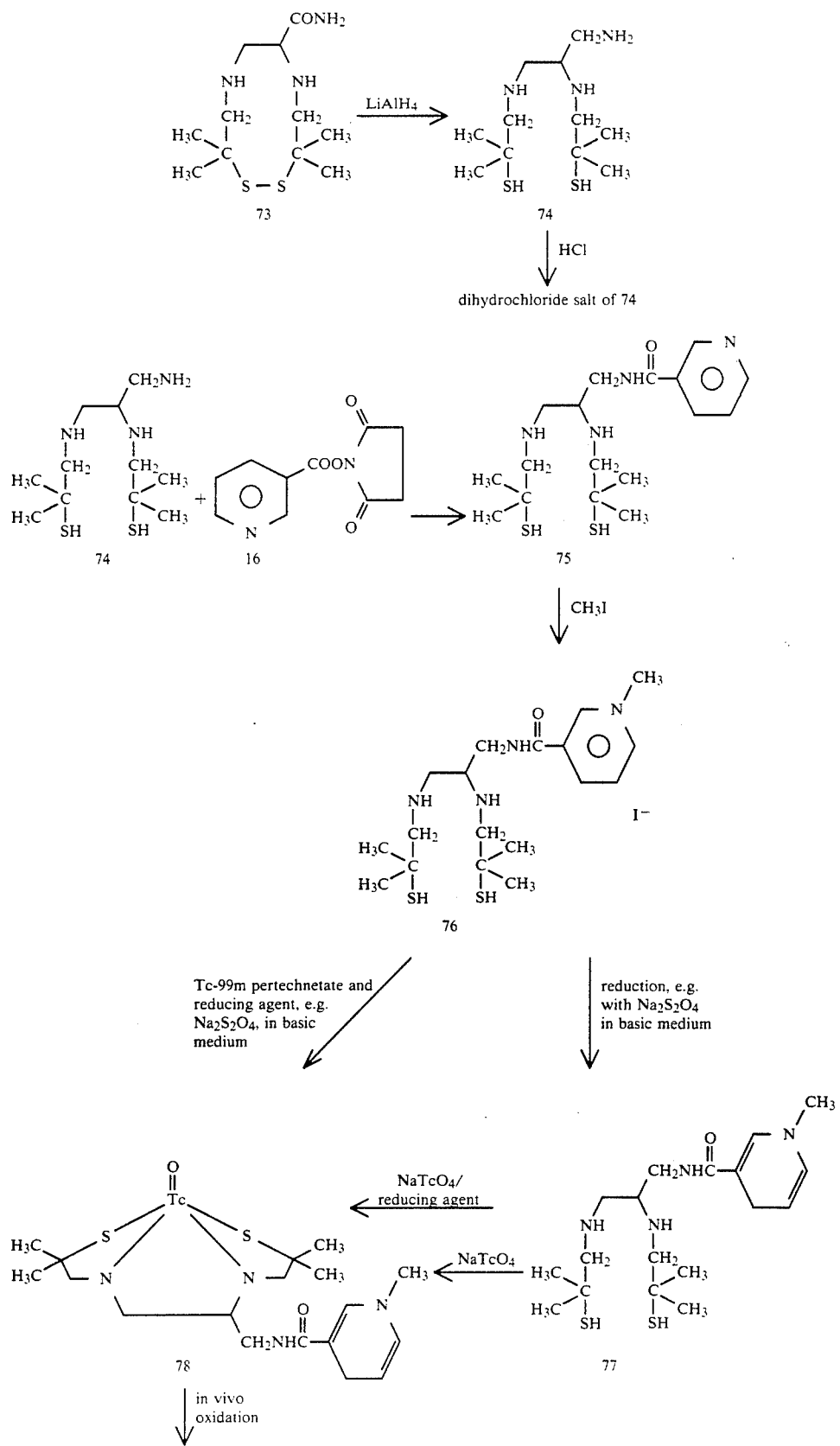

-continued
SCHEME 9
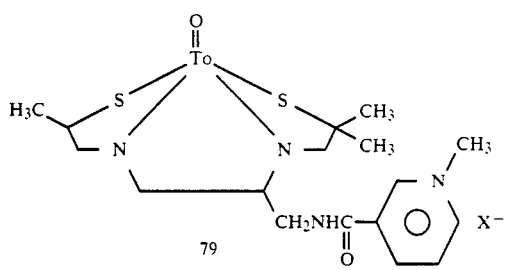
SCHEME 10
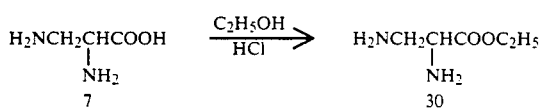
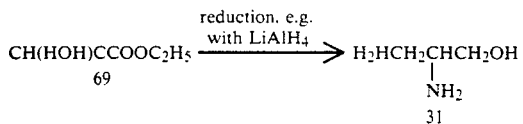
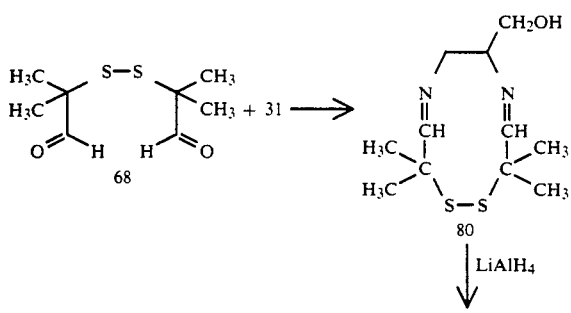
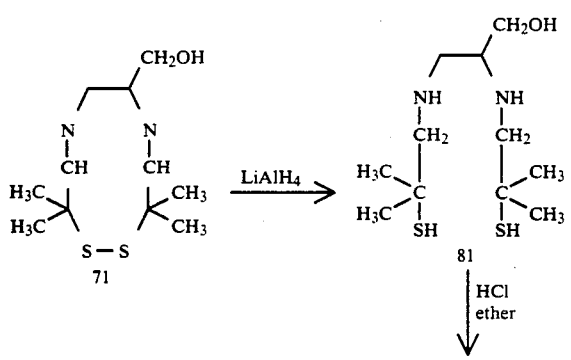
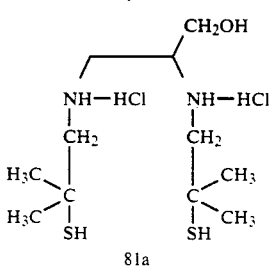

-continued
SCHEME 10
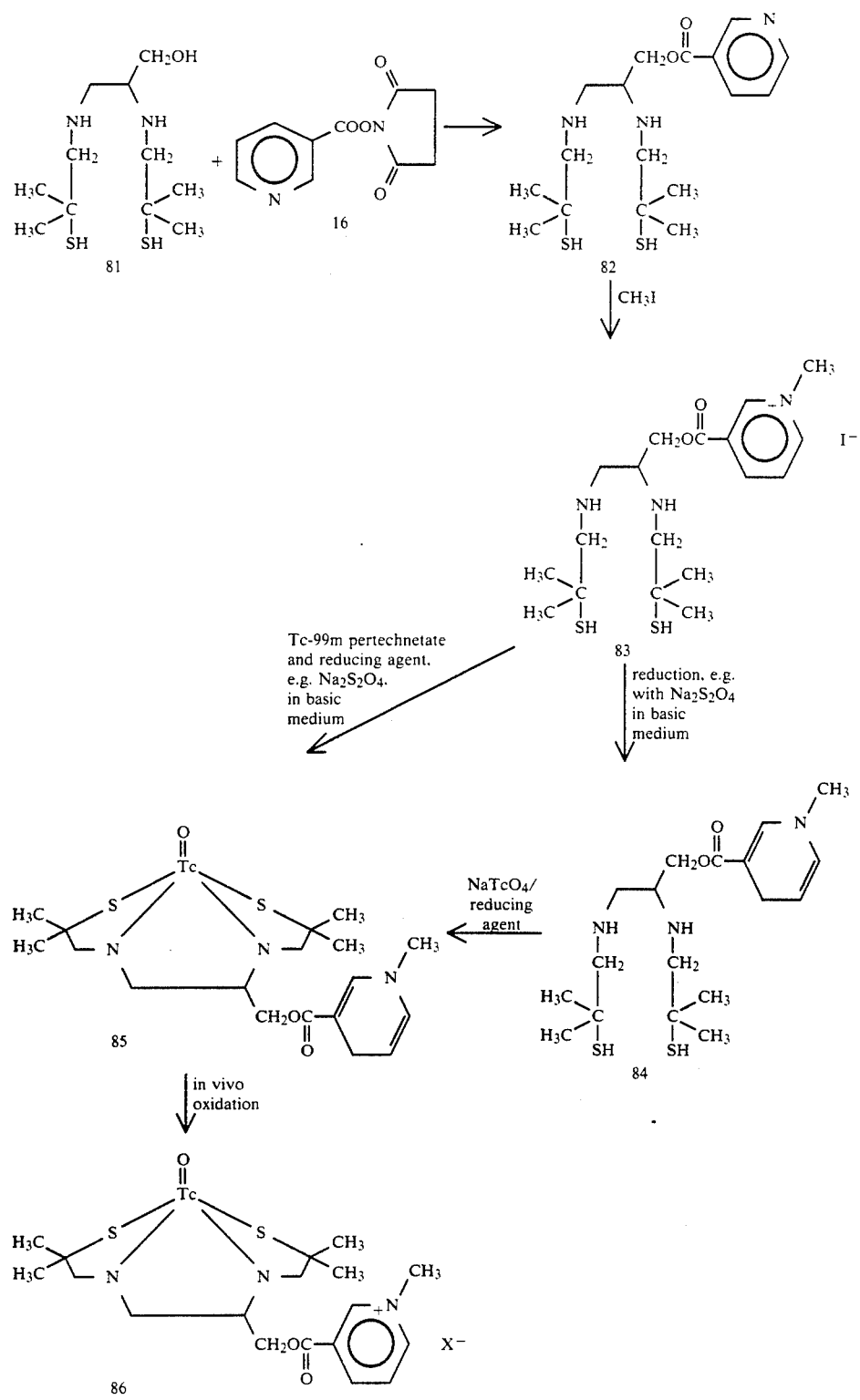
form "locked in" brain

SCHEME II
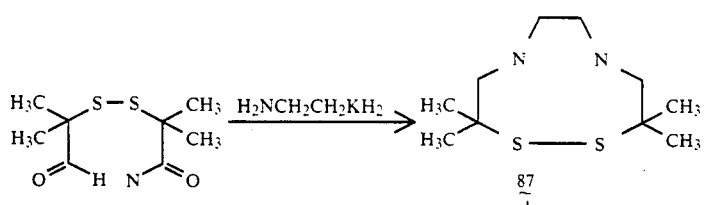
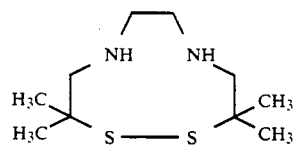
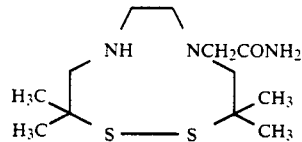
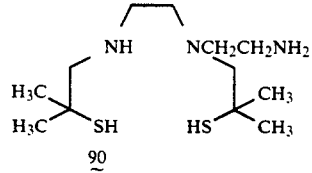
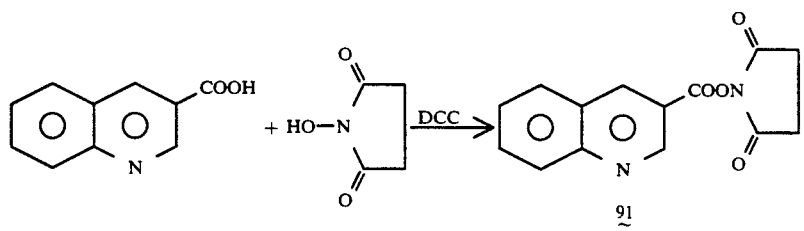
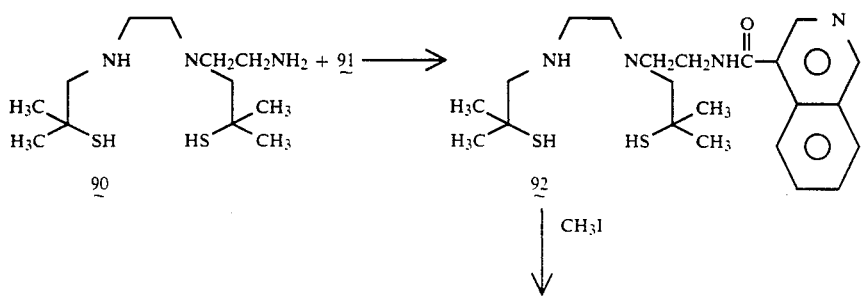

-continued
SCHEME II
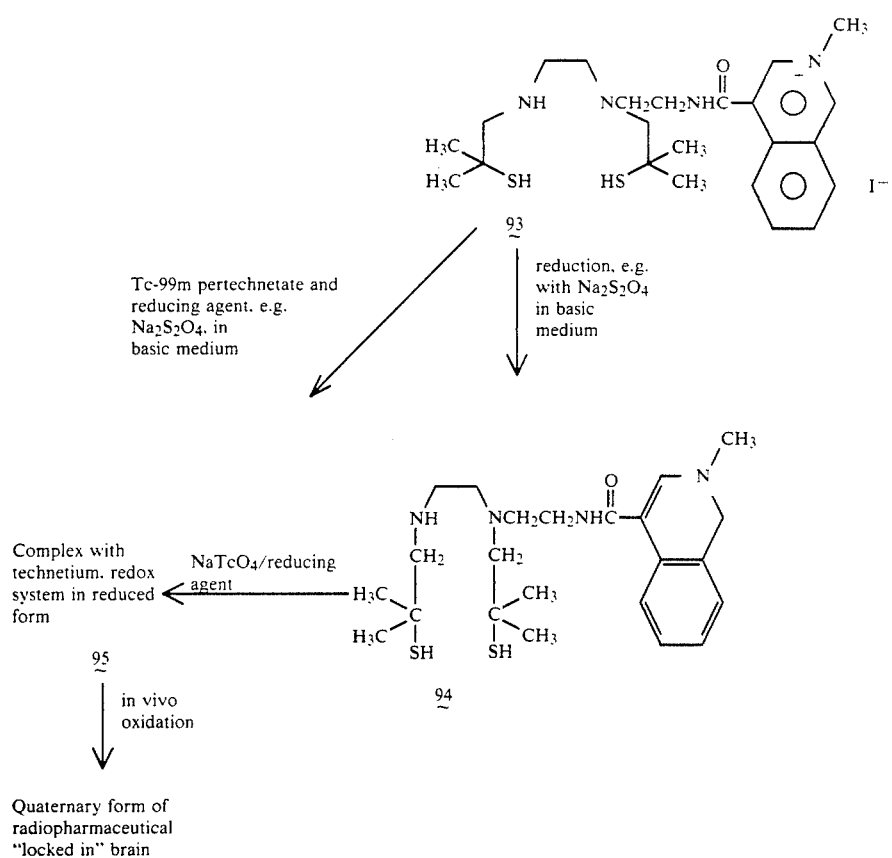
Scheme 12
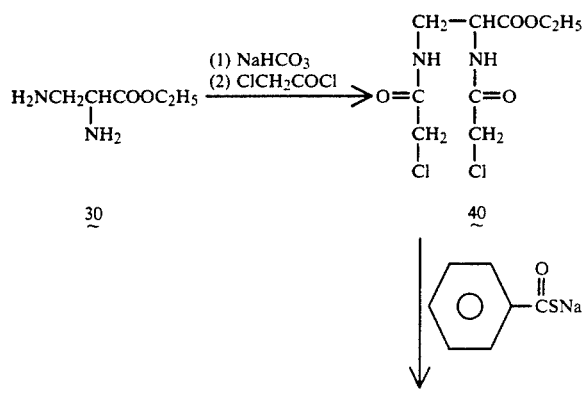

-continued
Scheme 12
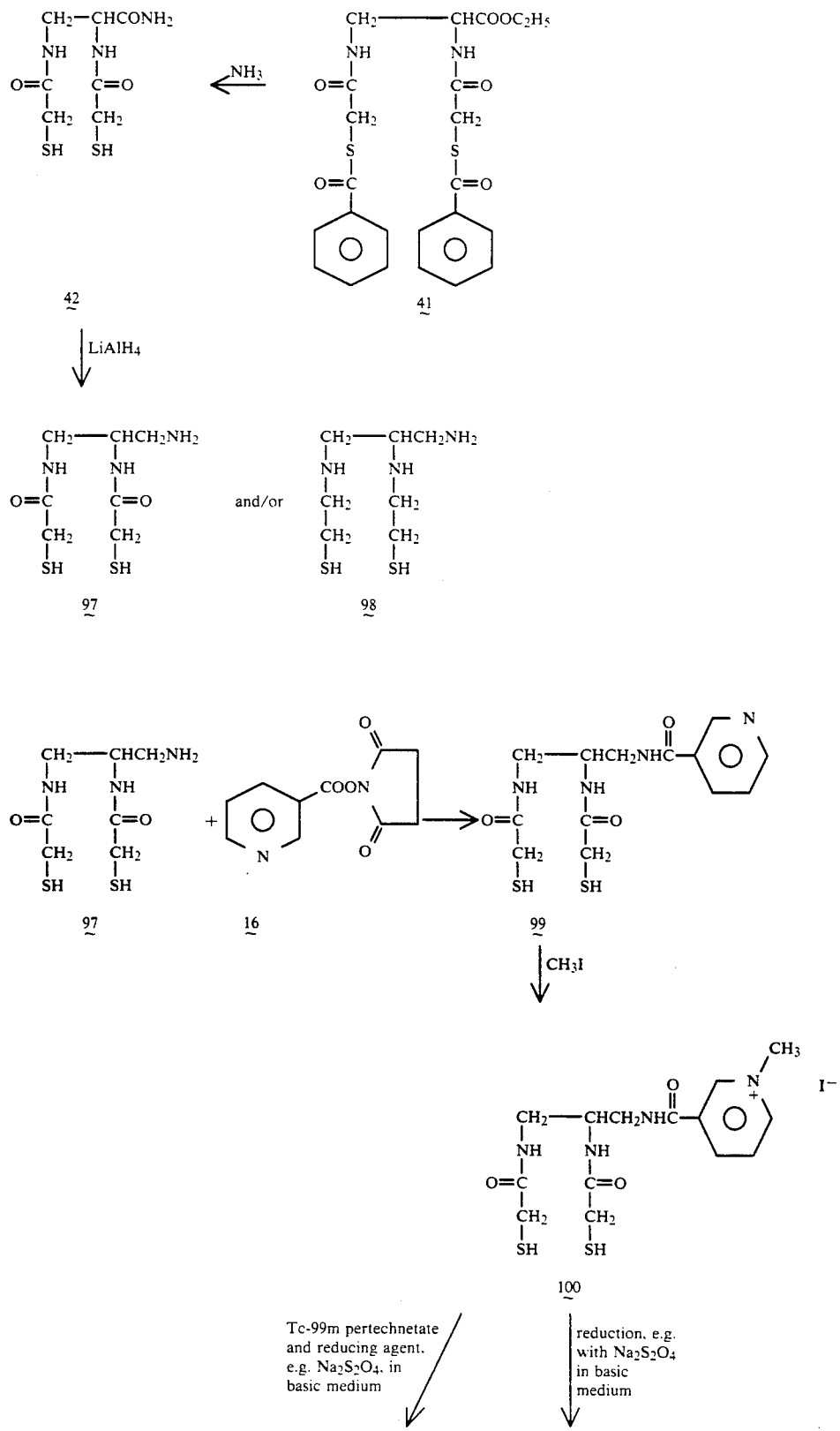

-continued
Scheme 12
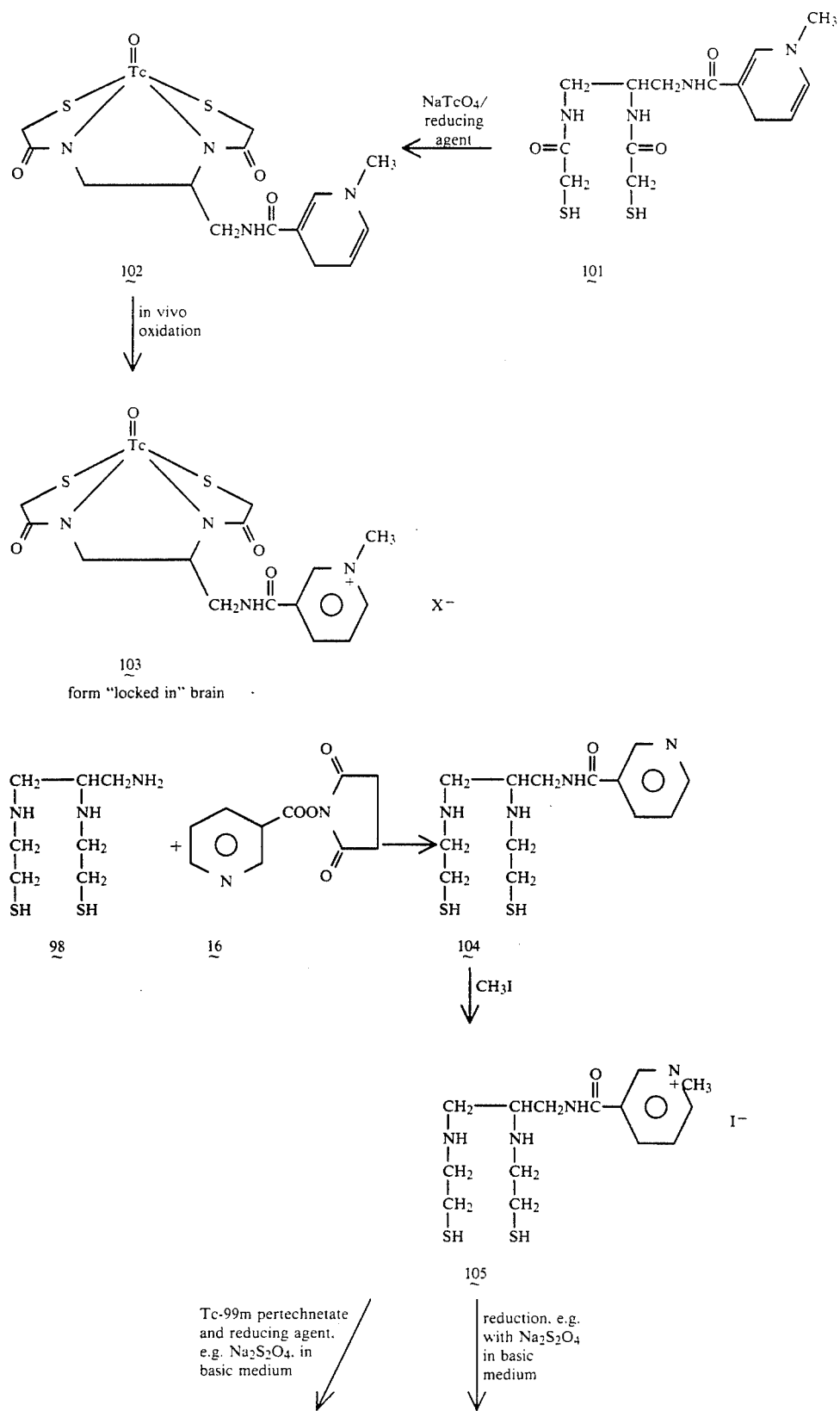

-continued
Scheme 12
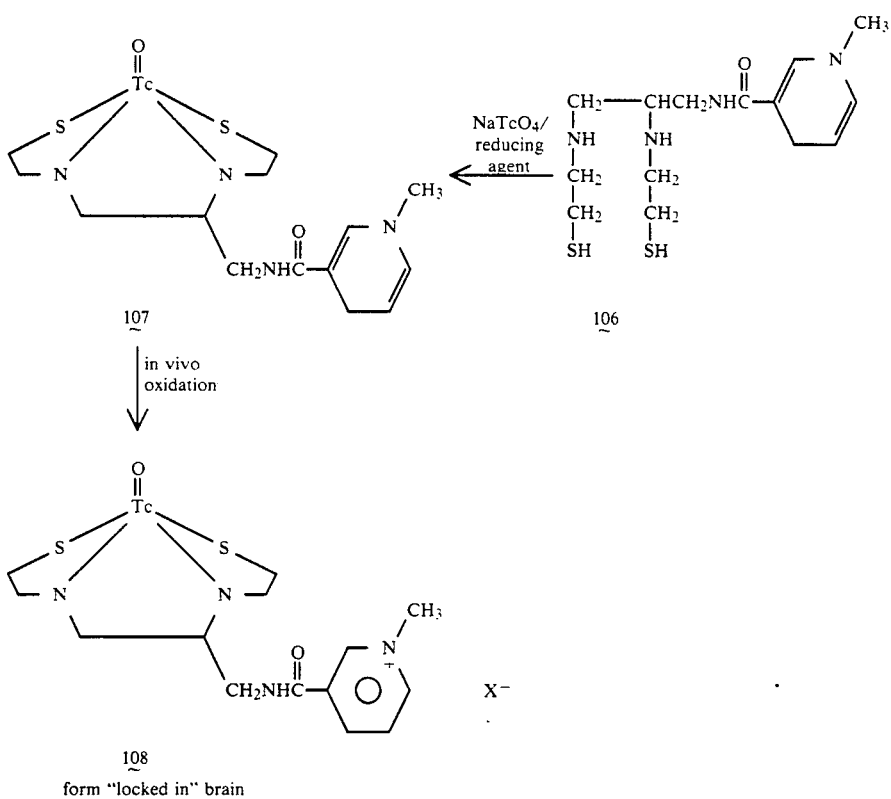
108 form "locked in" brain
Scheme 13
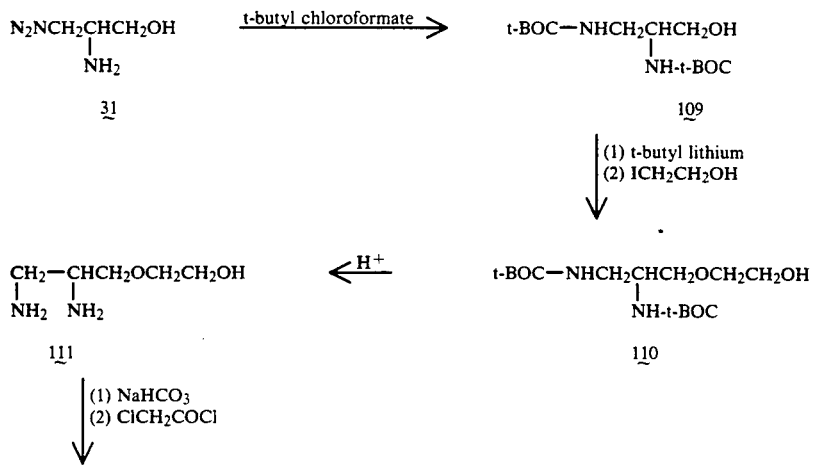

Scheme 13
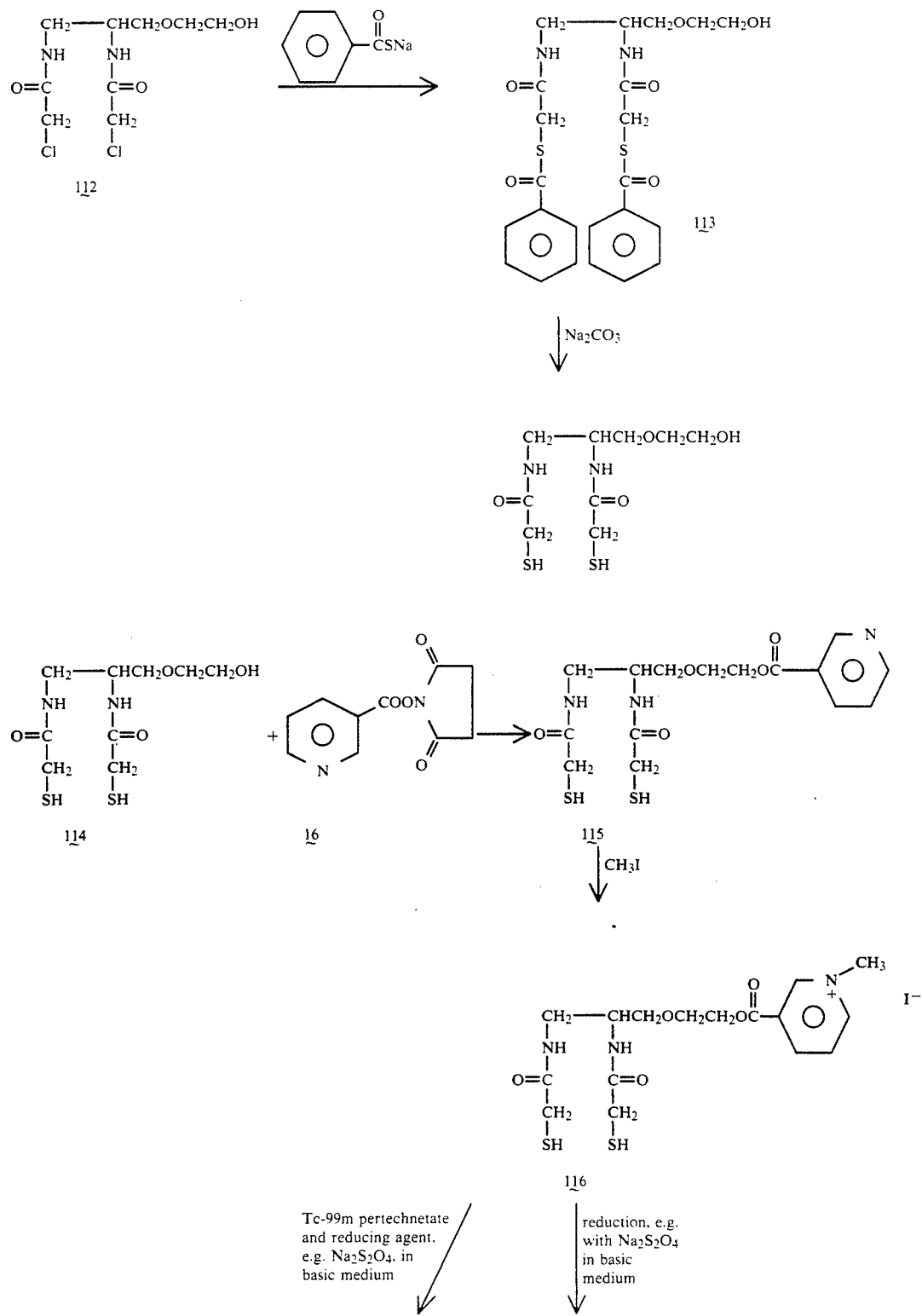

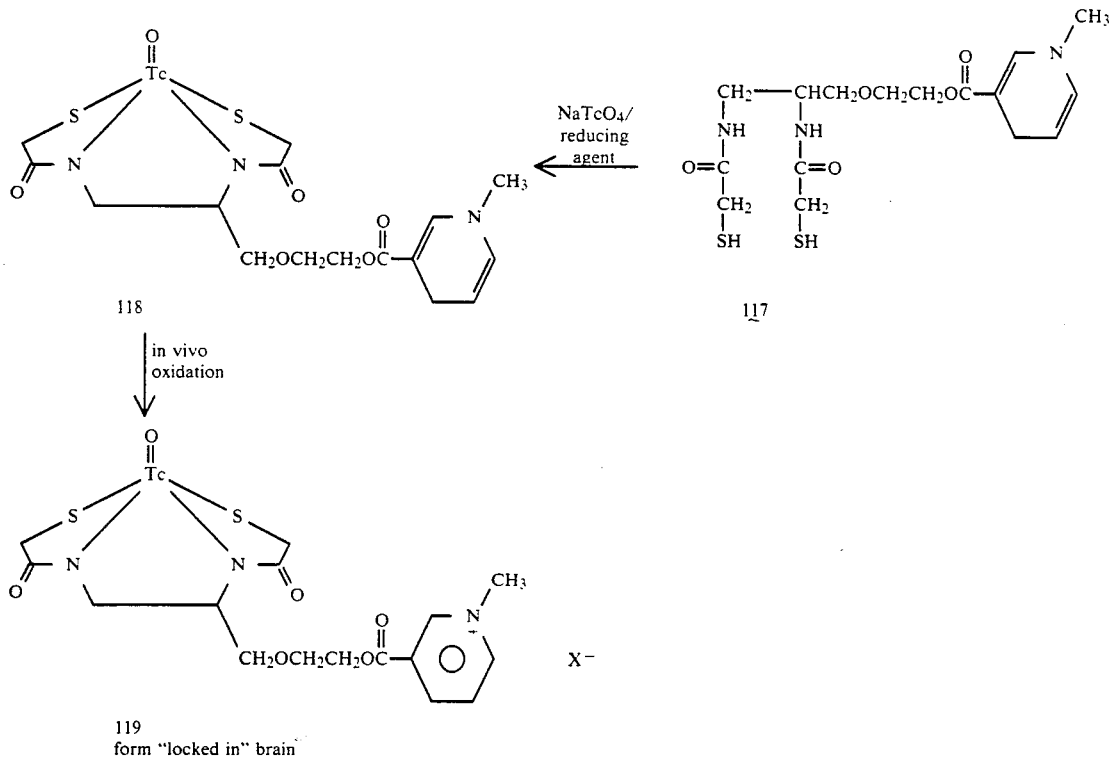
SCHEME 14
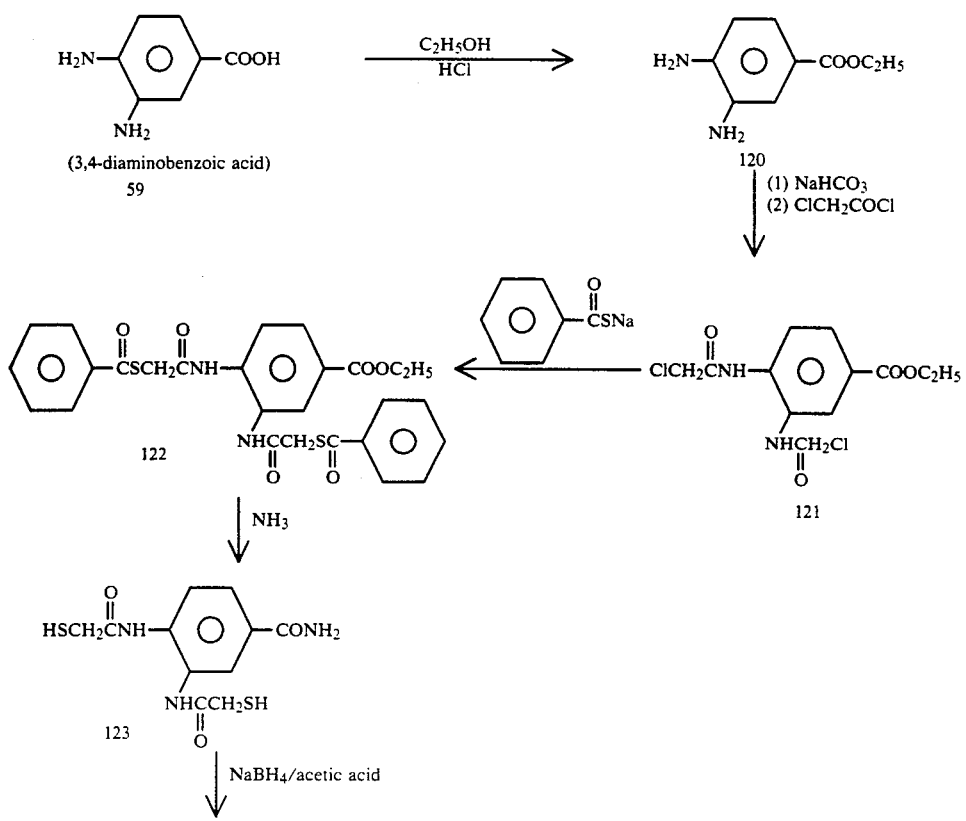

-continued
SCHEME 14
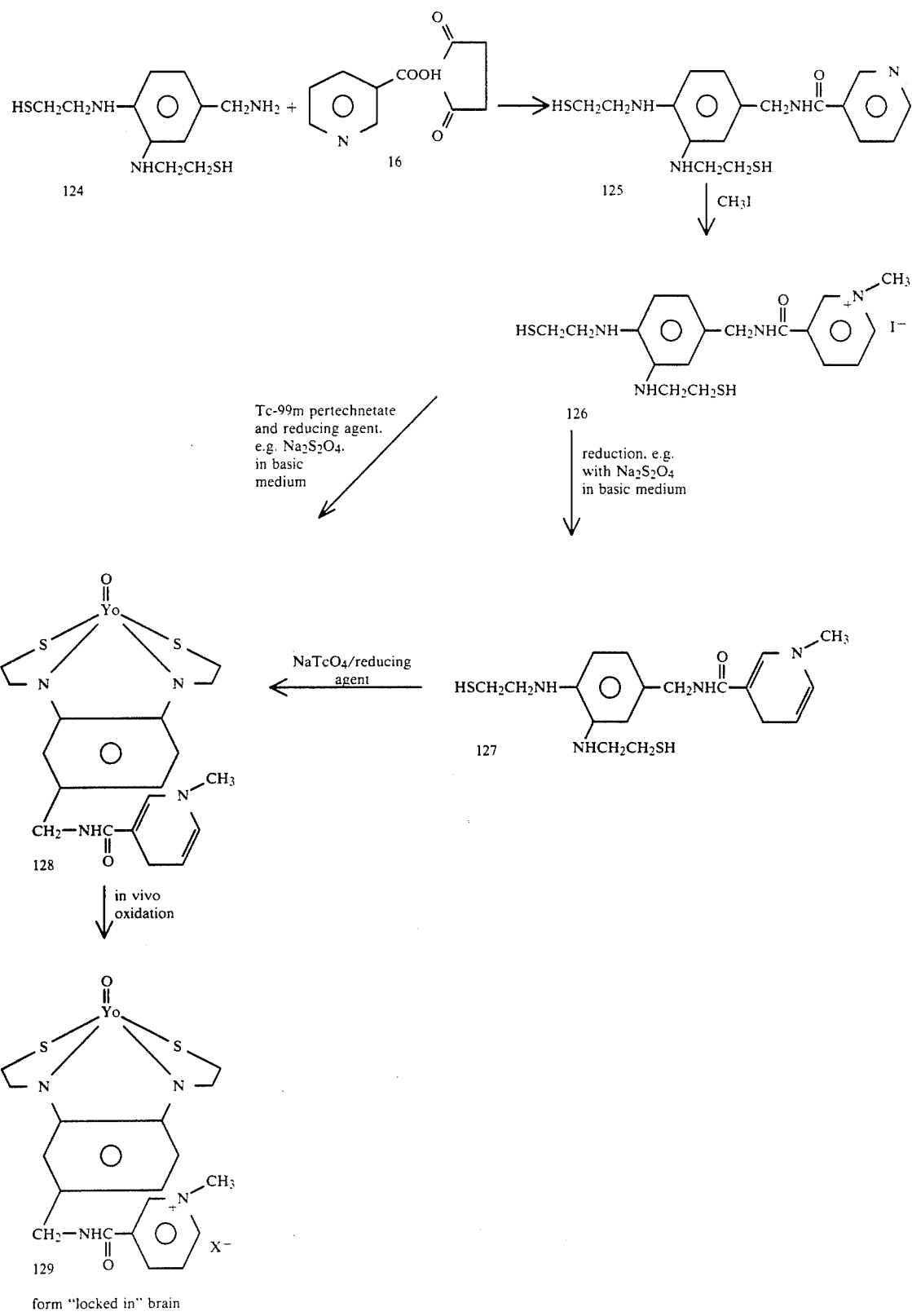
form "locked in" brain

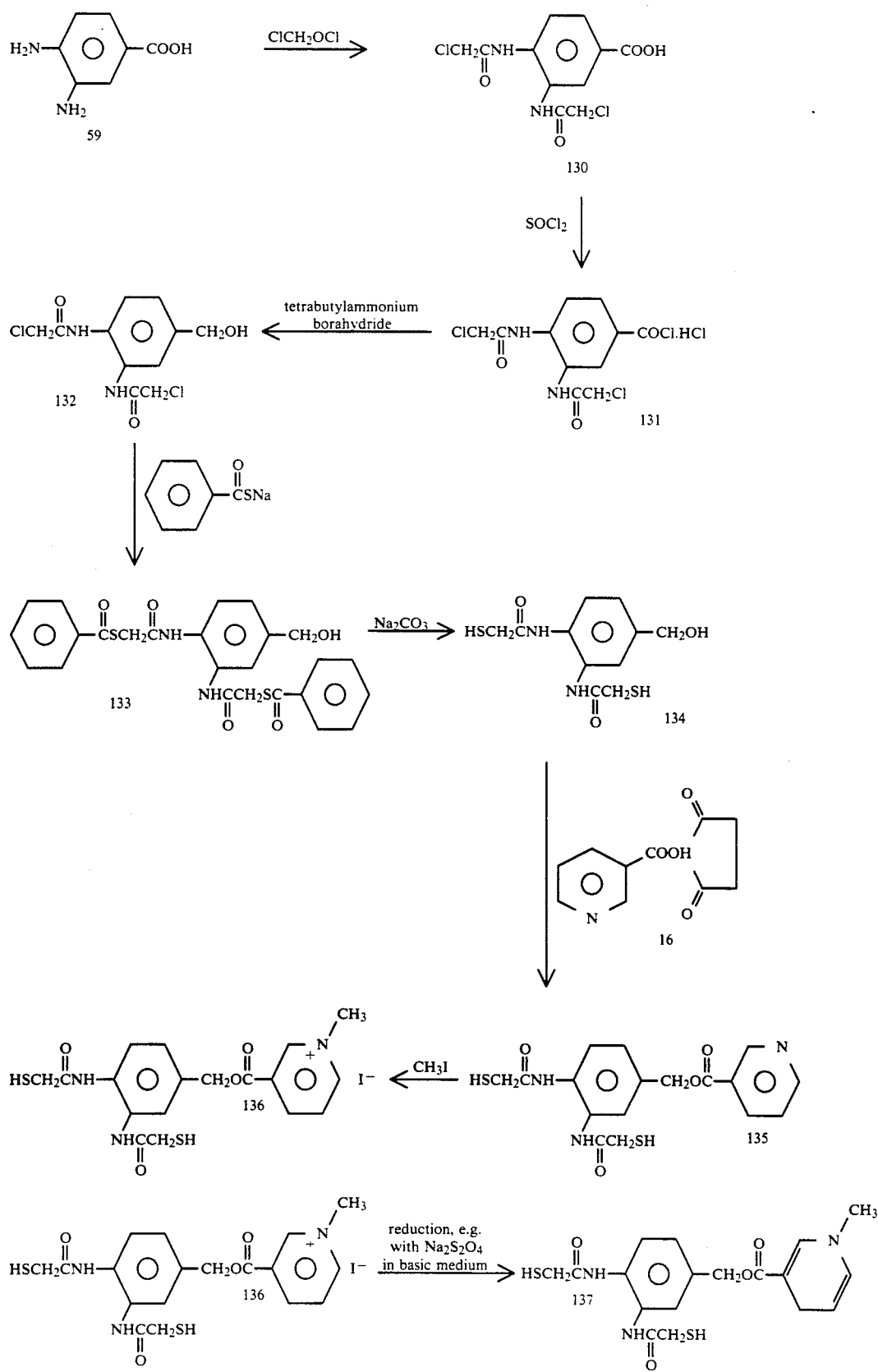

-continued
SCHEME 15
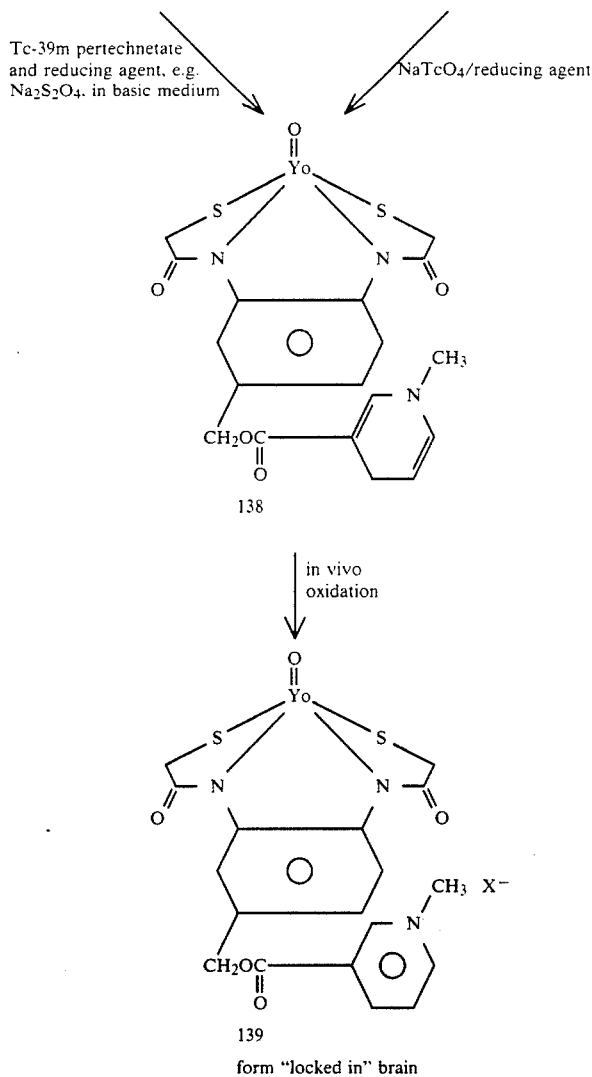
SCHEME 16
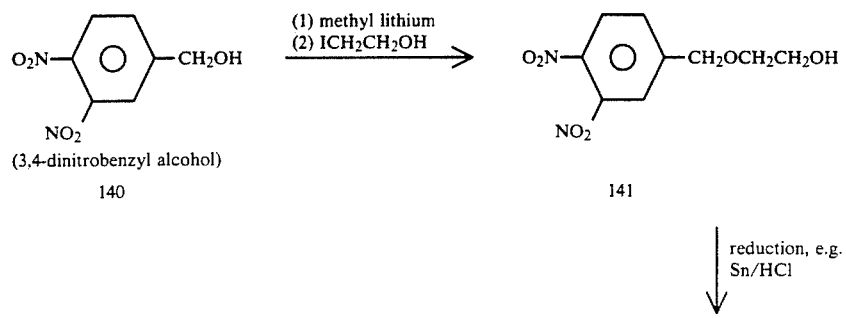

-continued
SCHEME 16
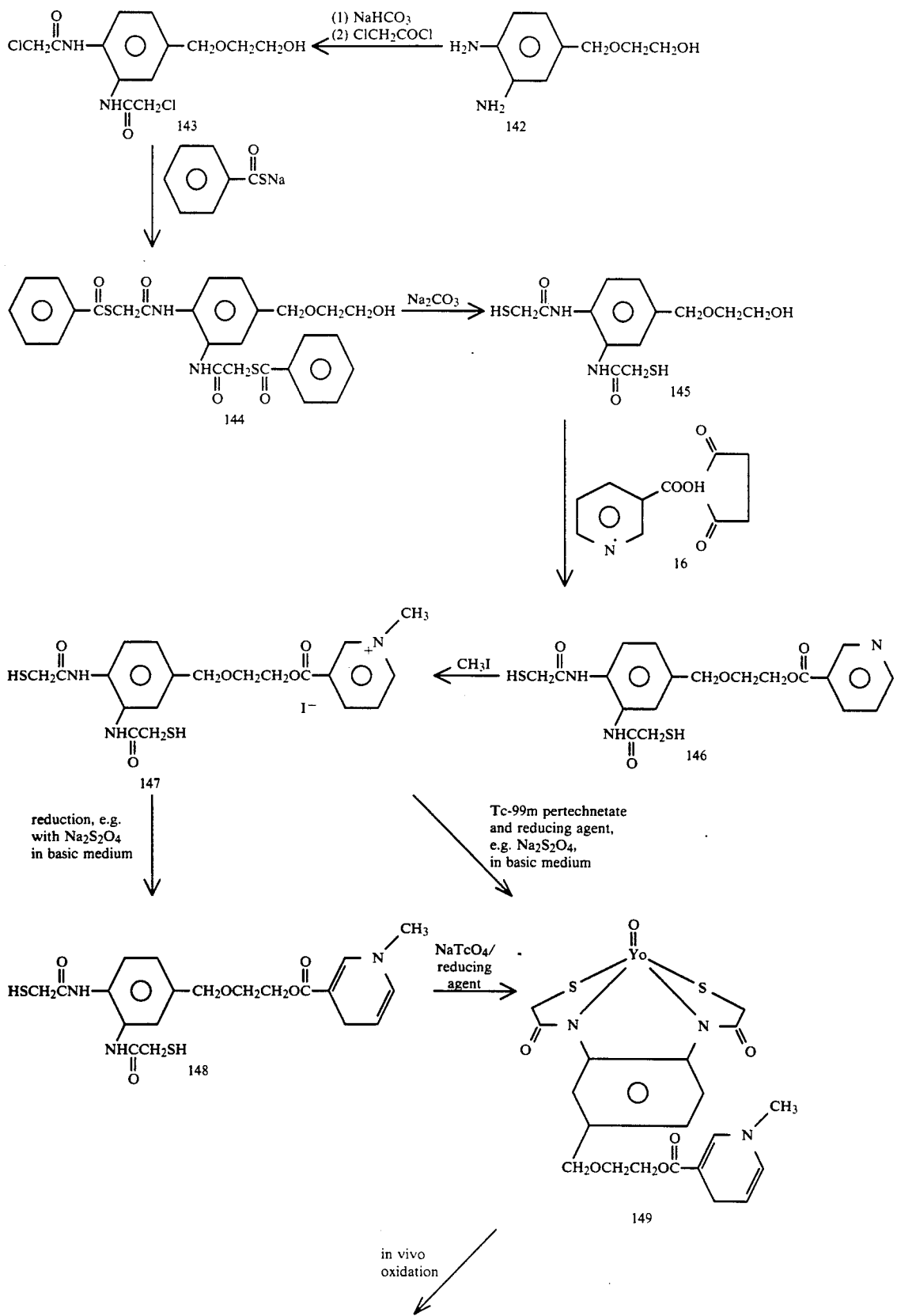

SCHEME 16
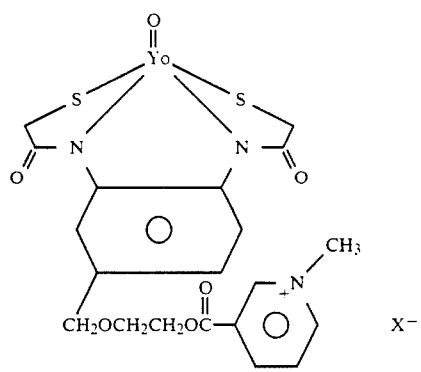
150
form "locked in" brain
SCHEME 17
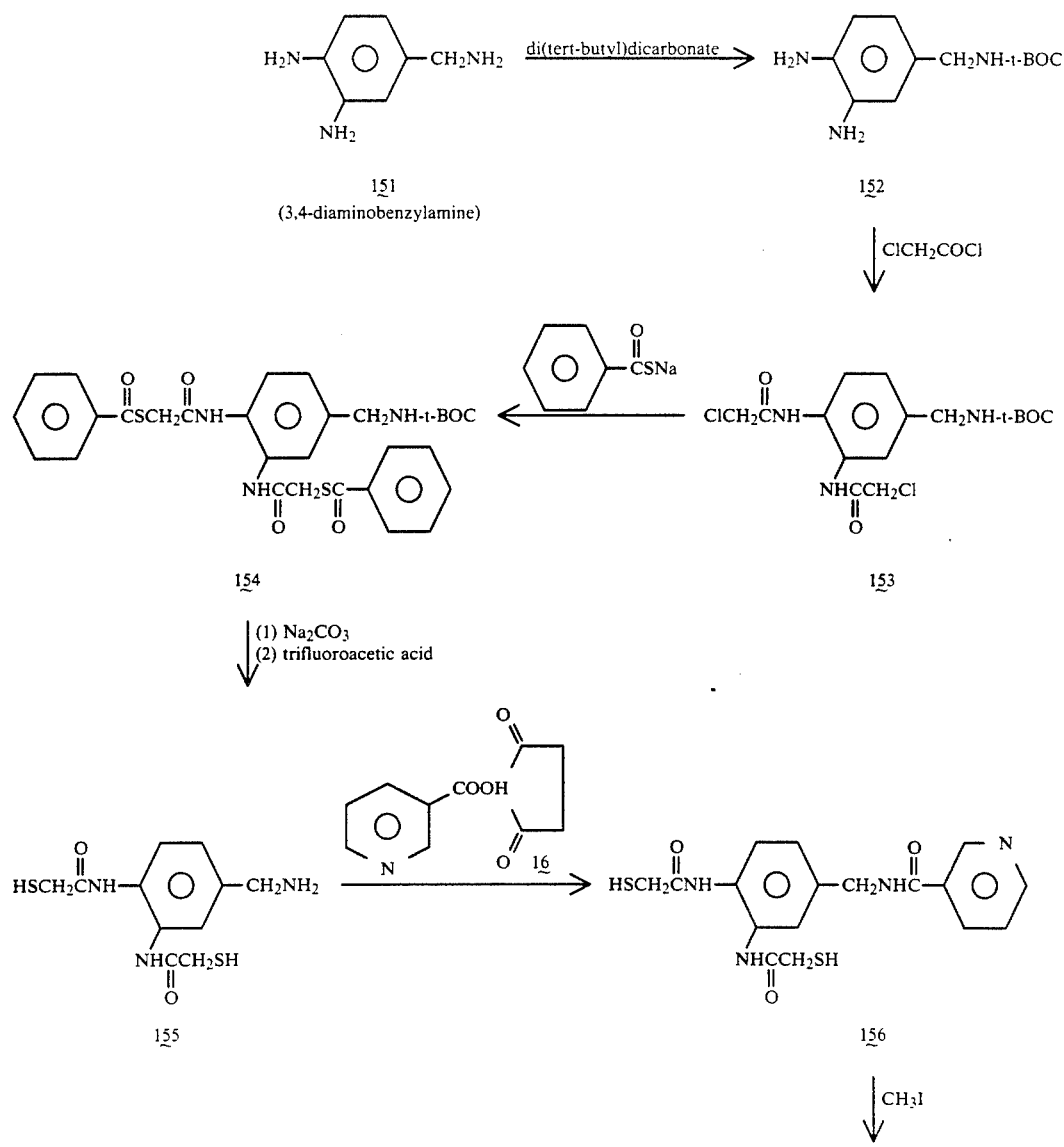

-continued
SCHEME 17
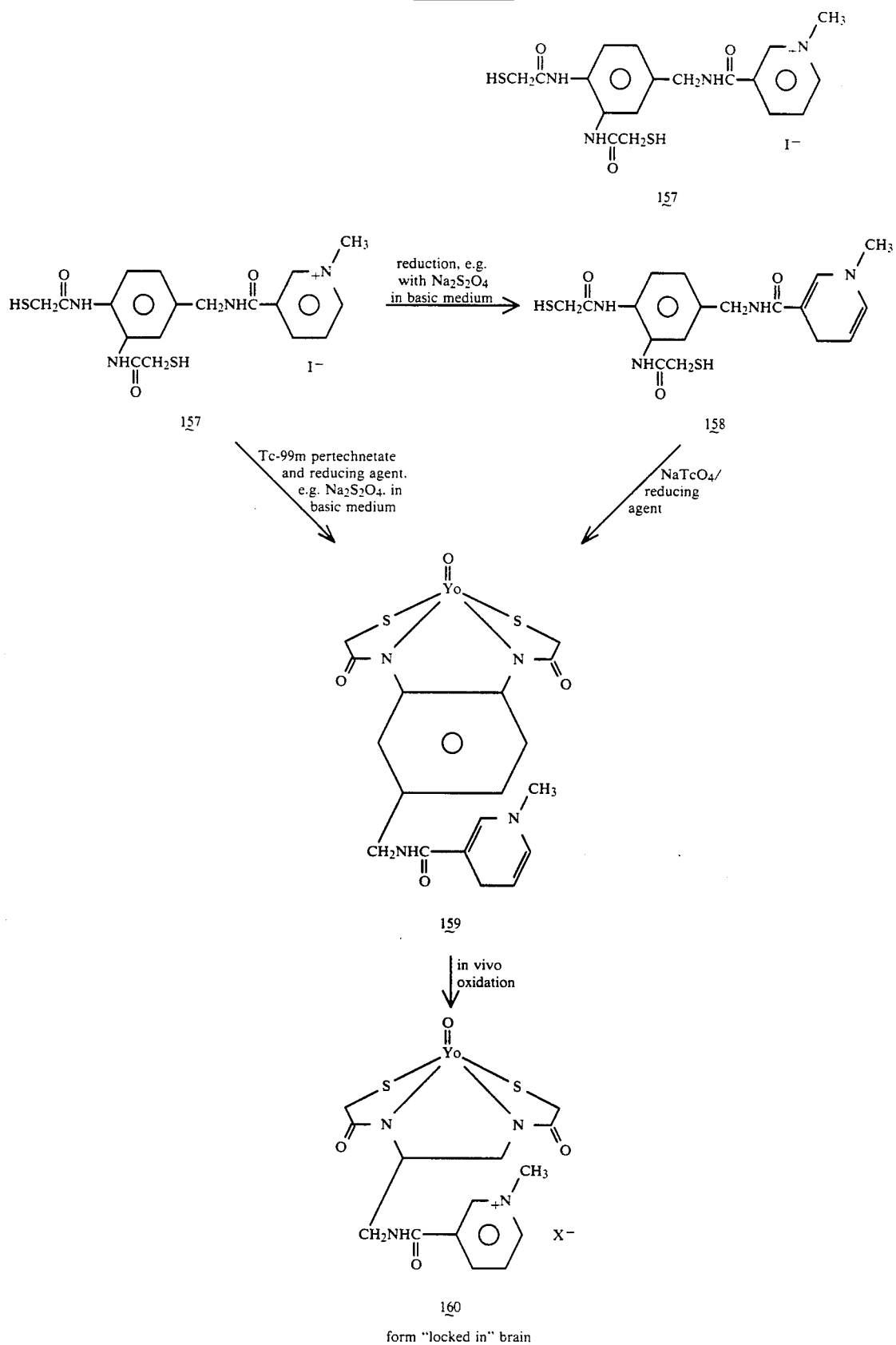

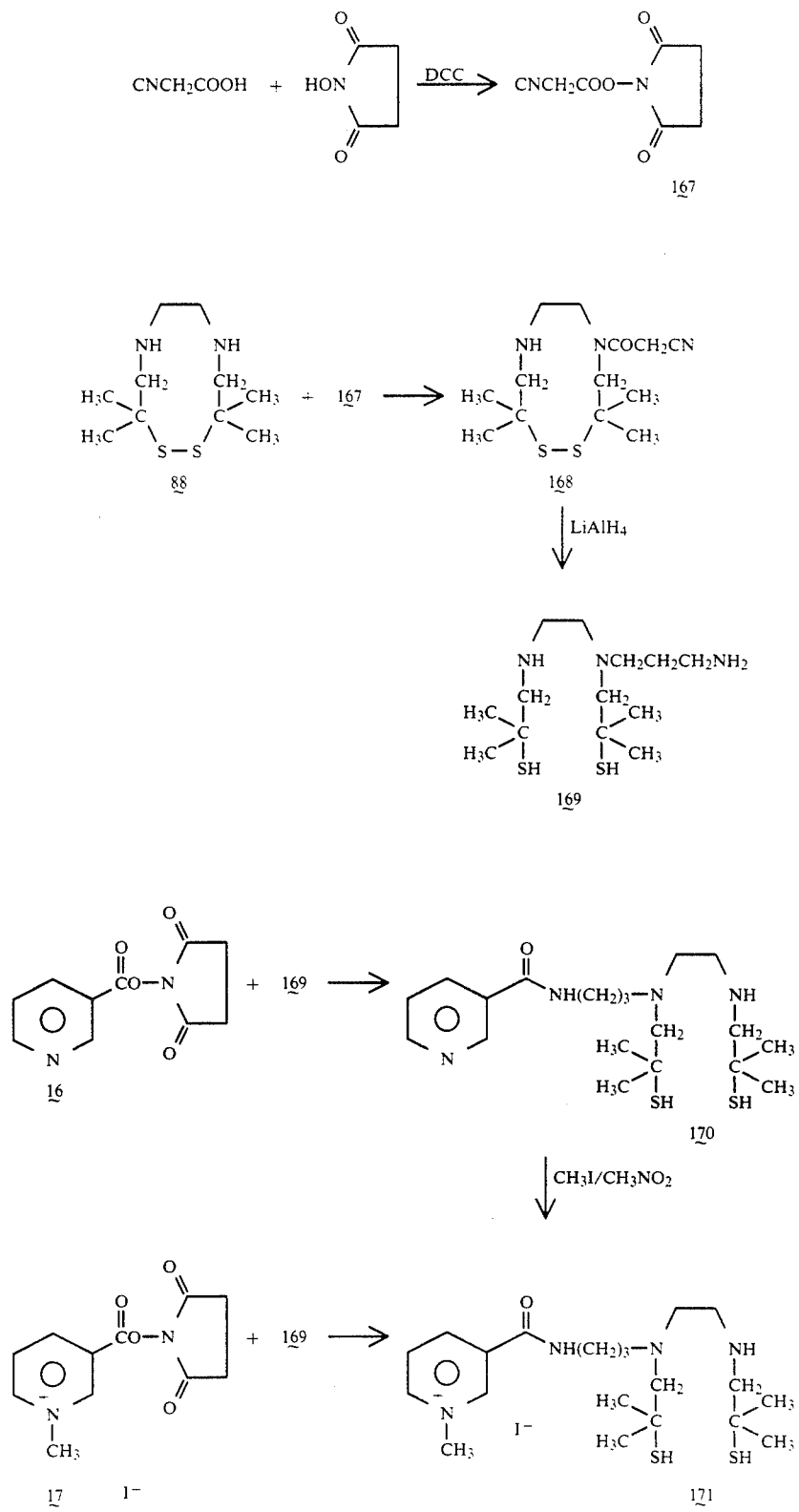

-continued
SCHEME 18
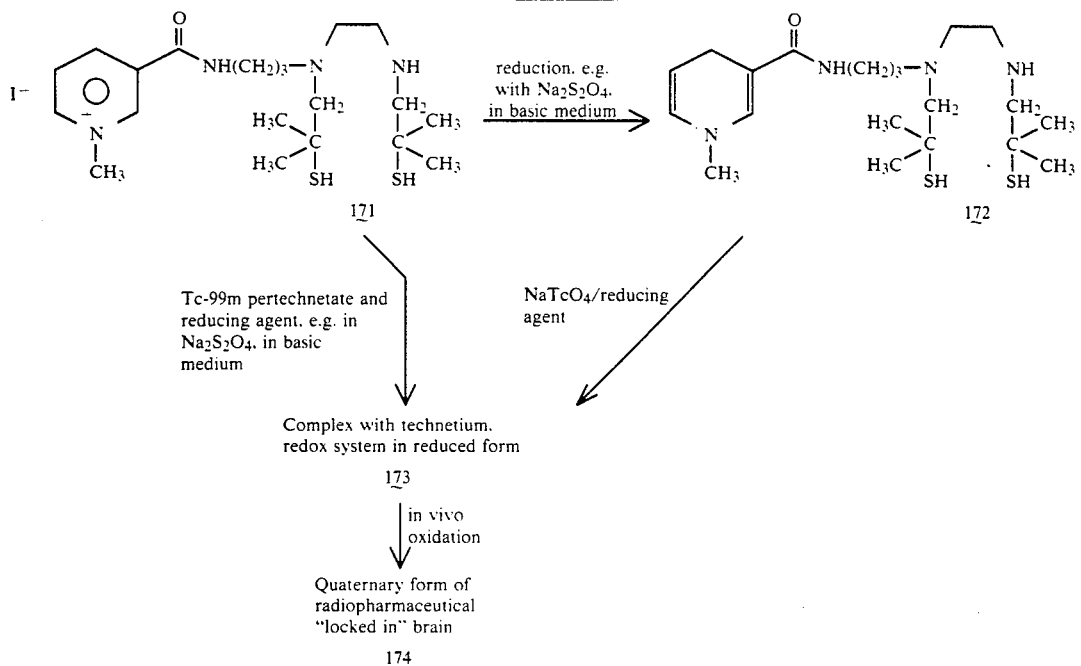
SCHEME 19
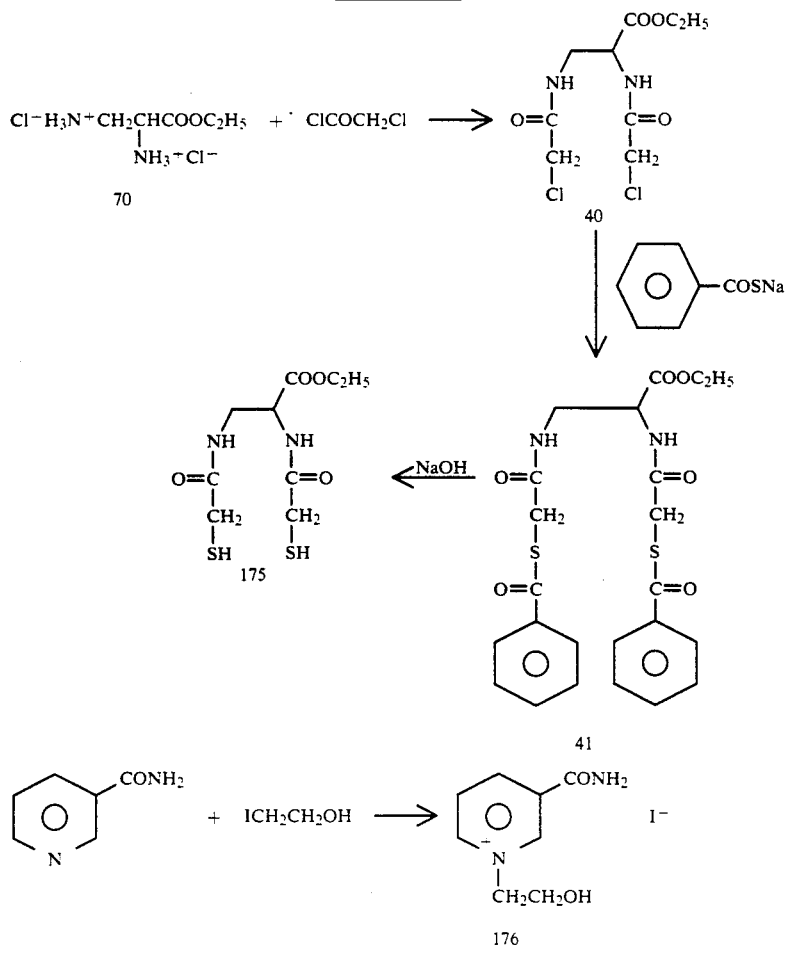

-continued
SCHEME 19
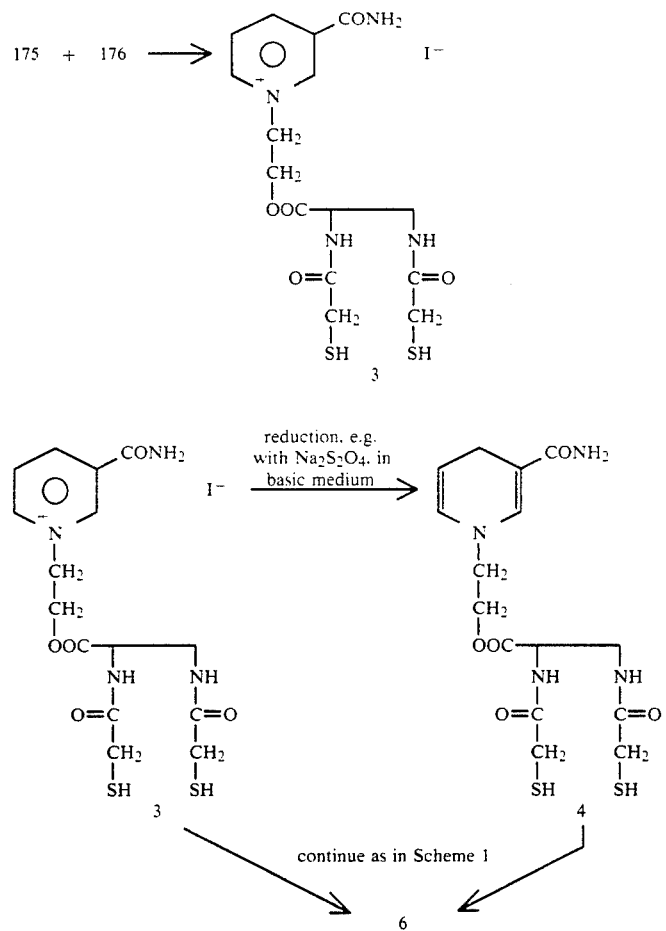
SCHEME 20
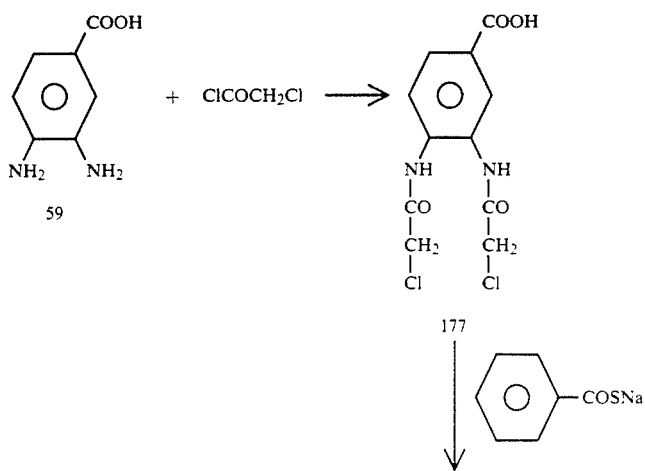

-continued
SCHEME 20
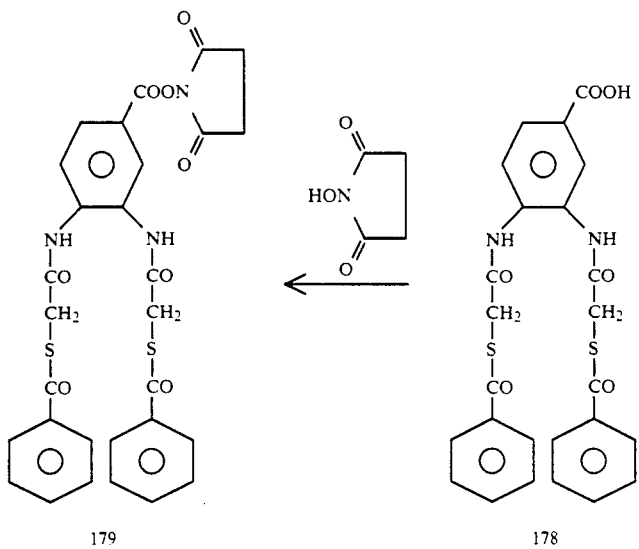
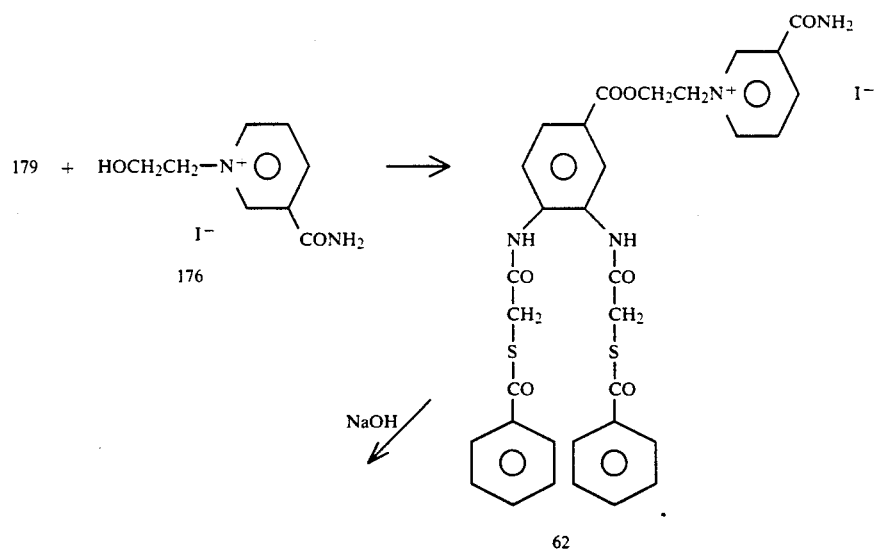
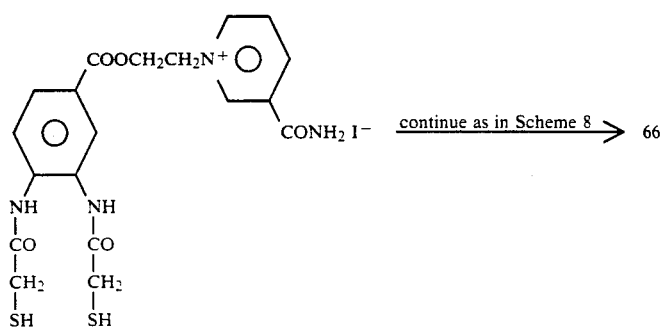

SCHEME 21
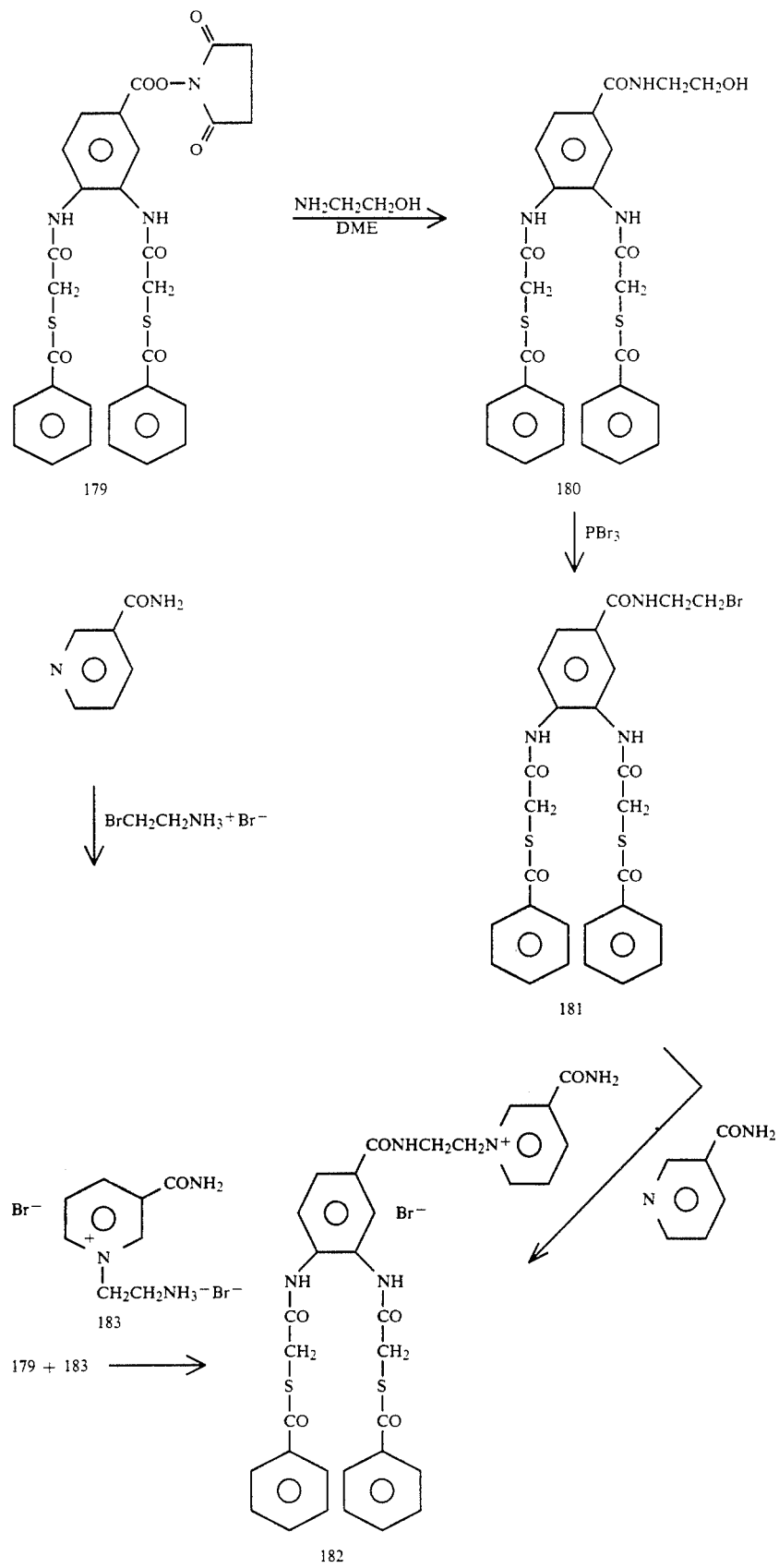

-continued
SCHEME 21
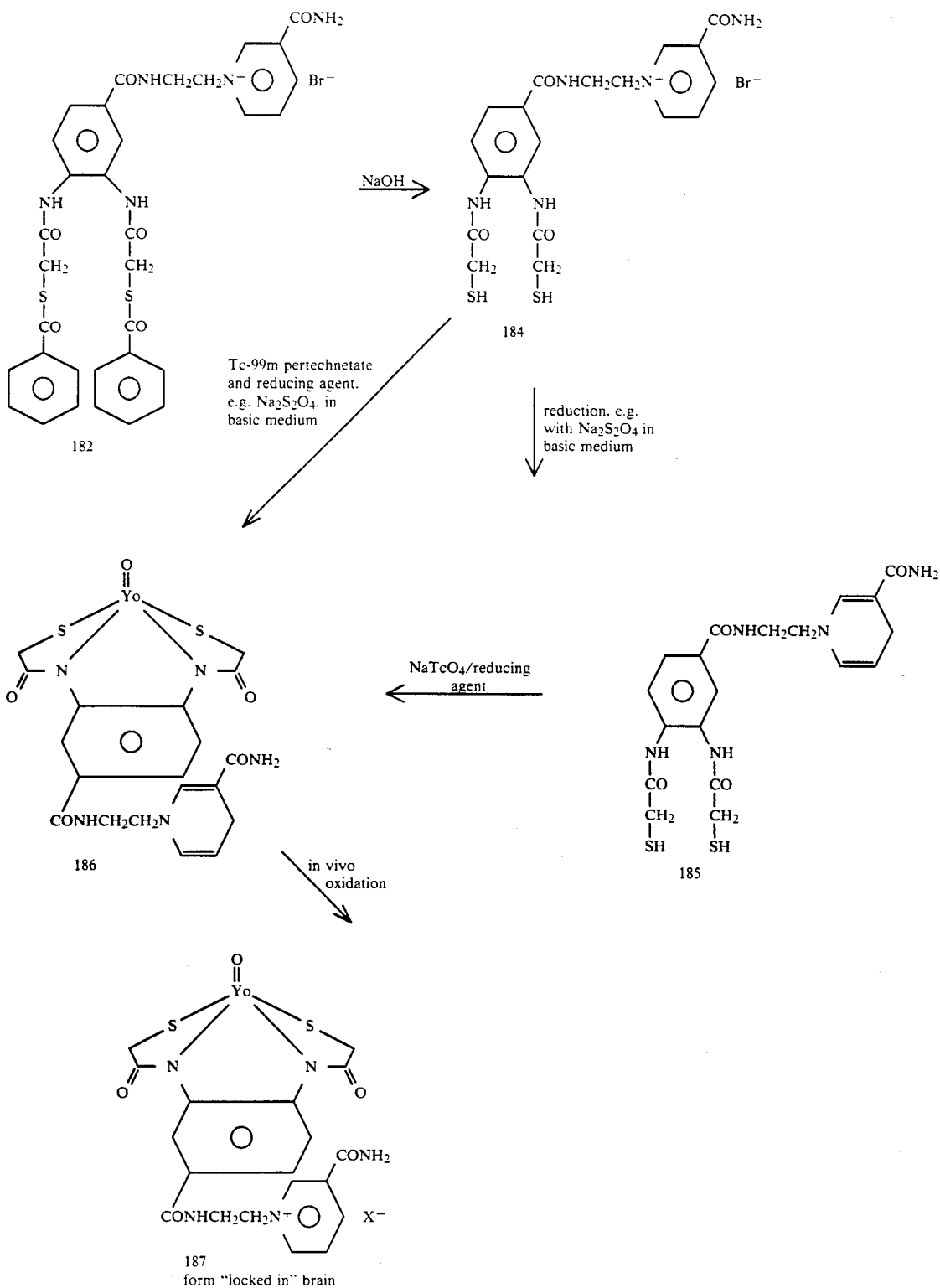
187 form "locked in" brain

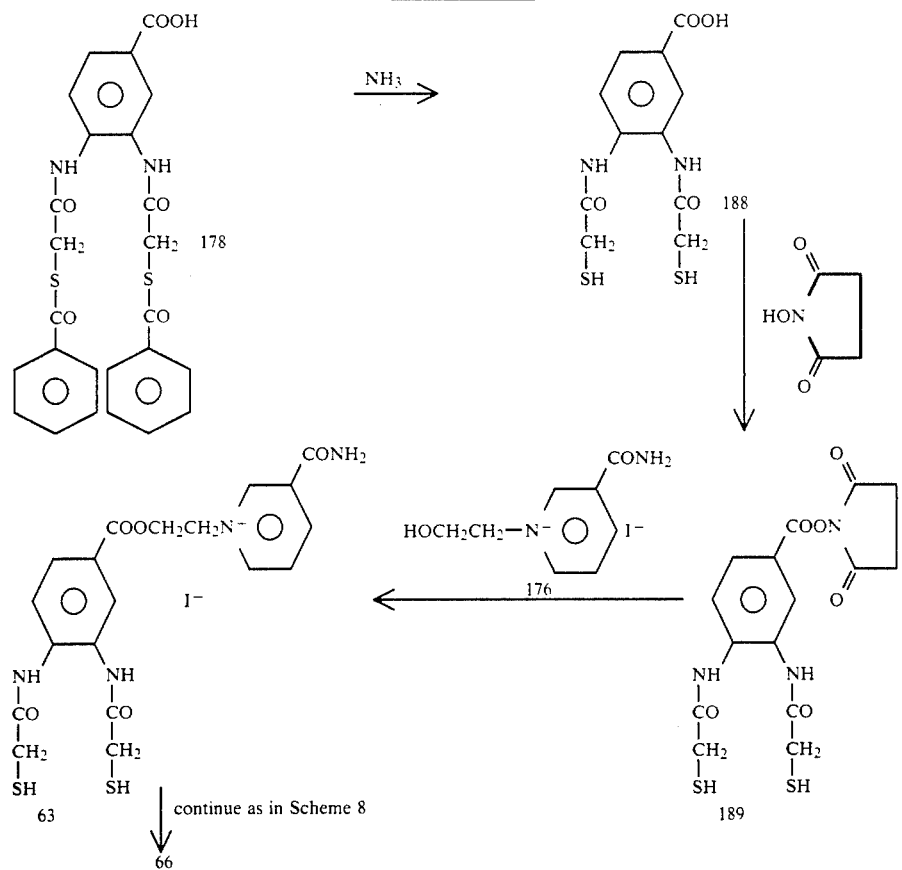
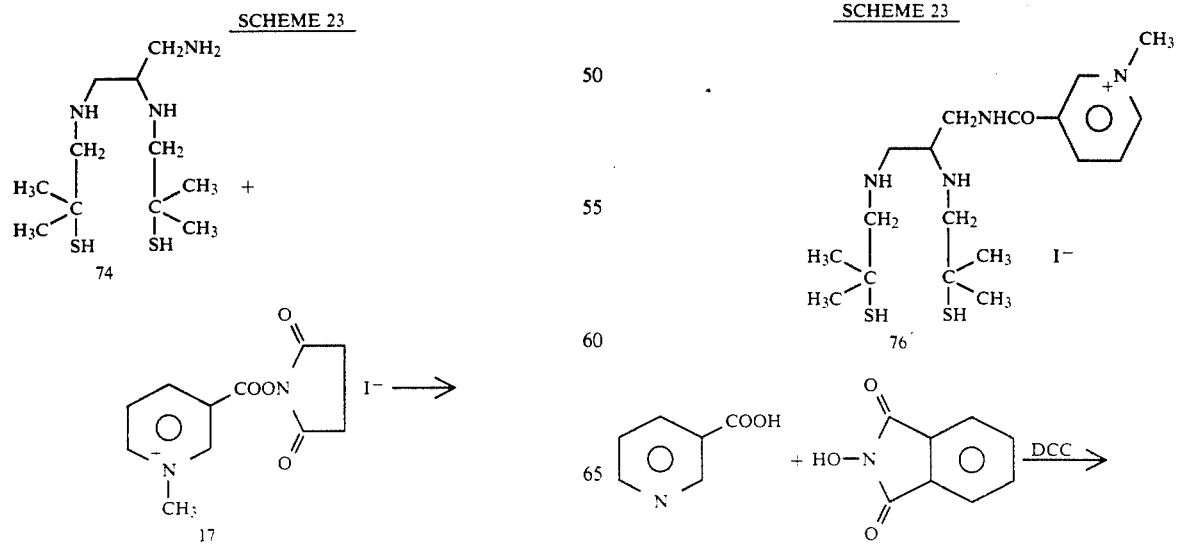

-continued
SCHEME 23
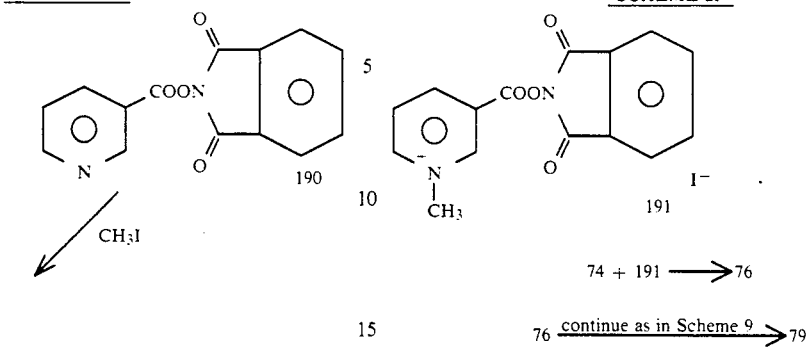
74 + 191 ⟶ 76
76 continue as in Scheme 9 ⟶ 79
SCHEME 24
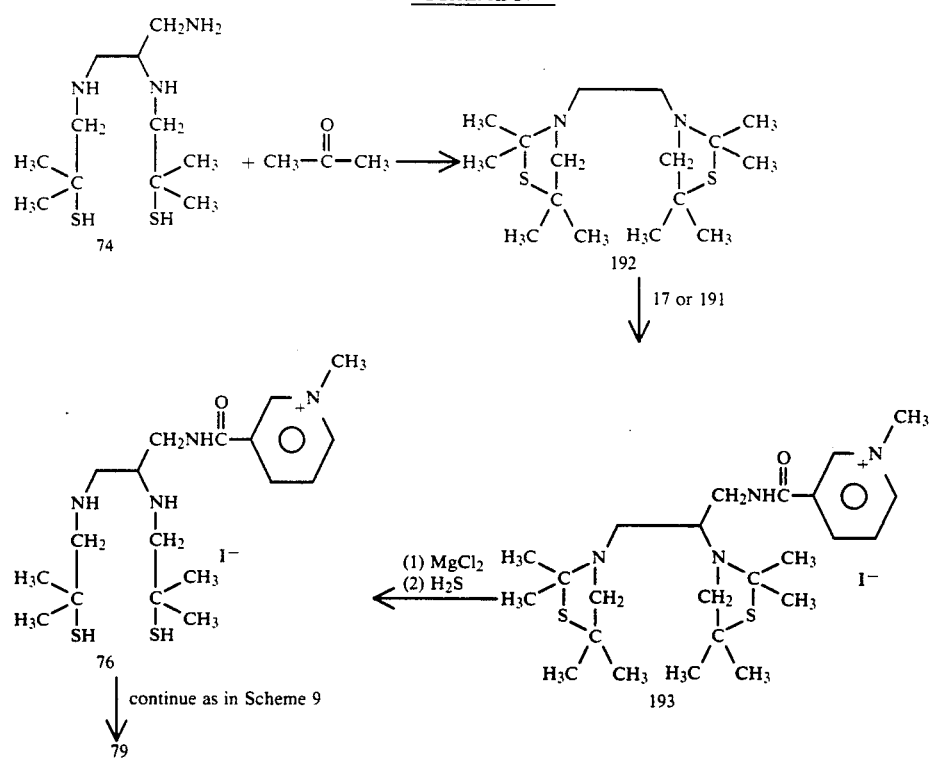
SCHEME 25
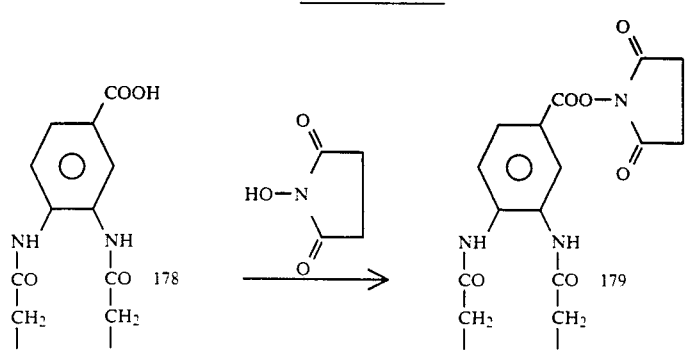

5,155,227
-continued
SCHEME 25
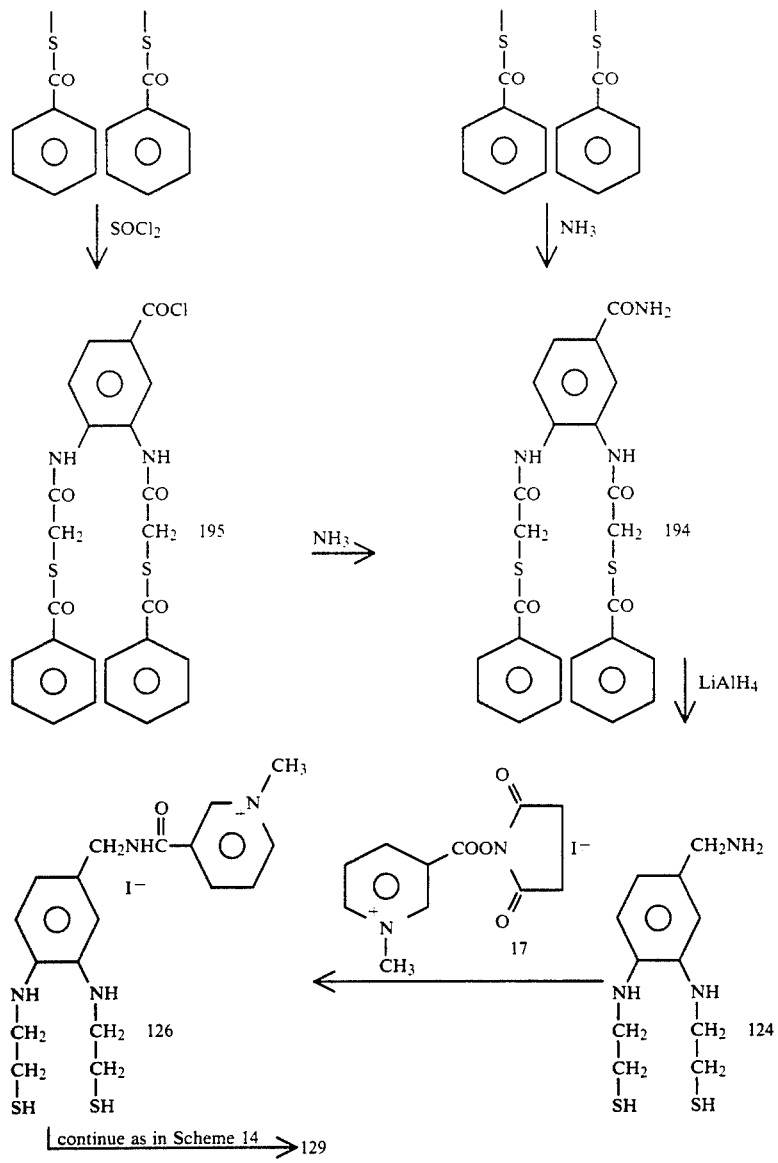
SCHEME 26
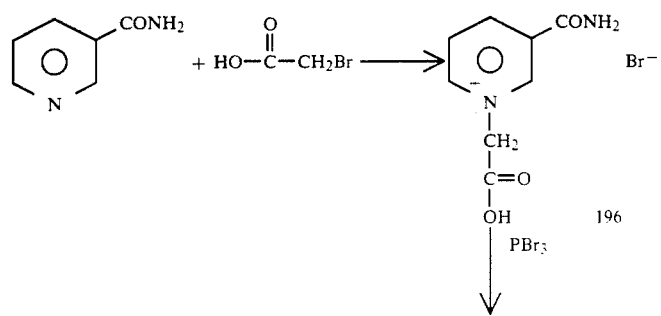

-continued
SCHEME 26
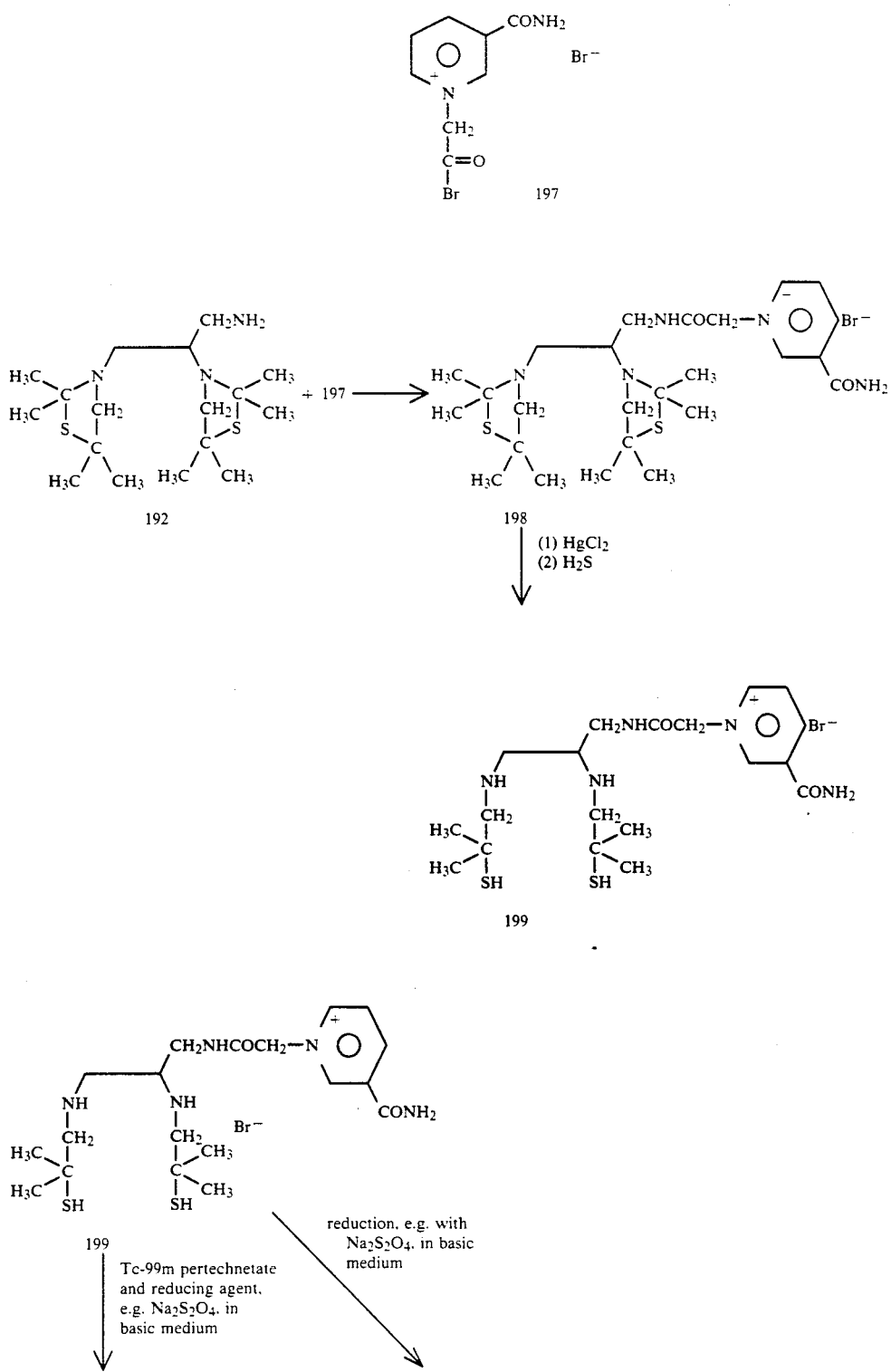

-continued
SCHEME 26
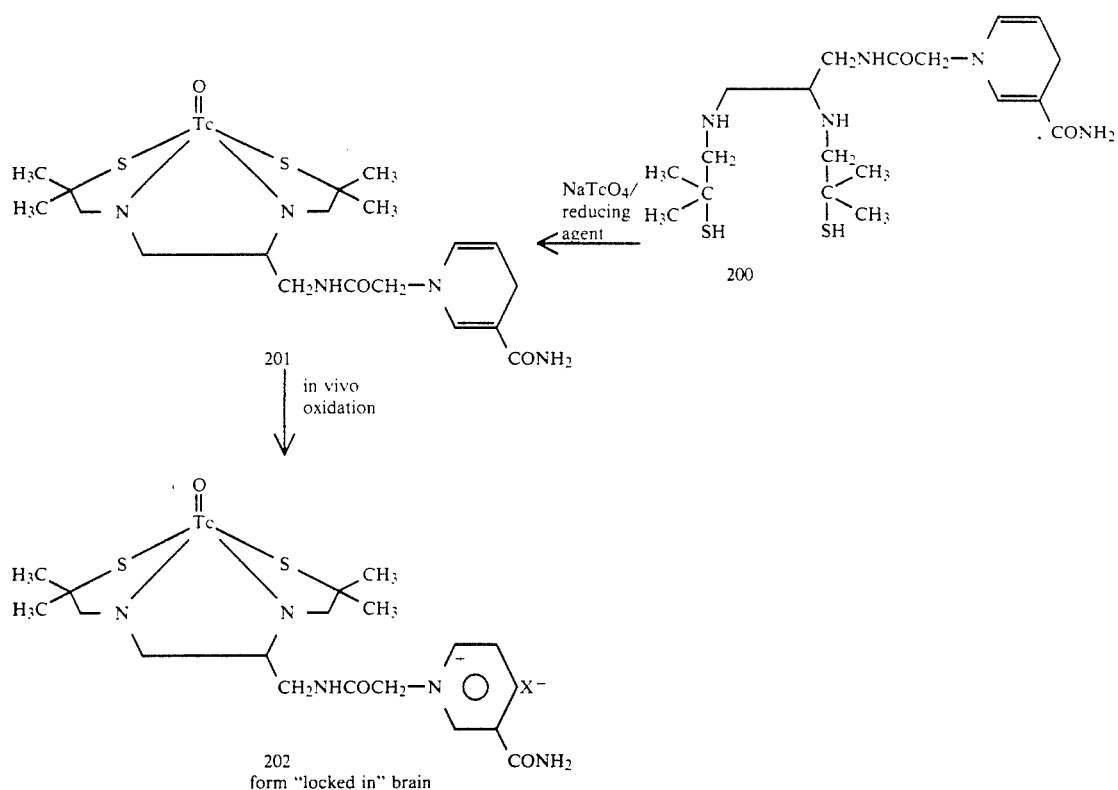
Scheme 27
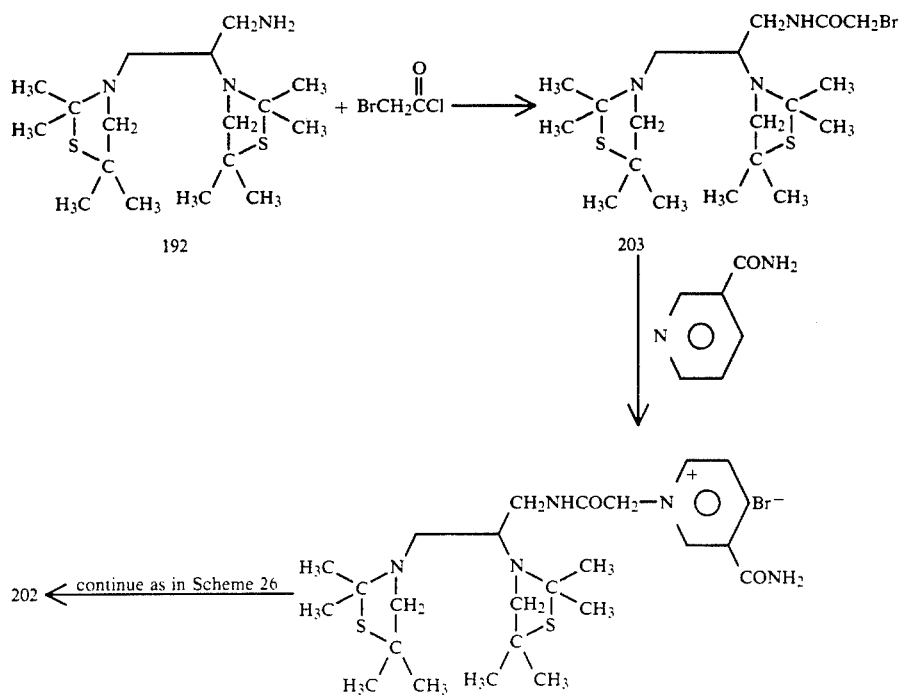

SCHEME 28
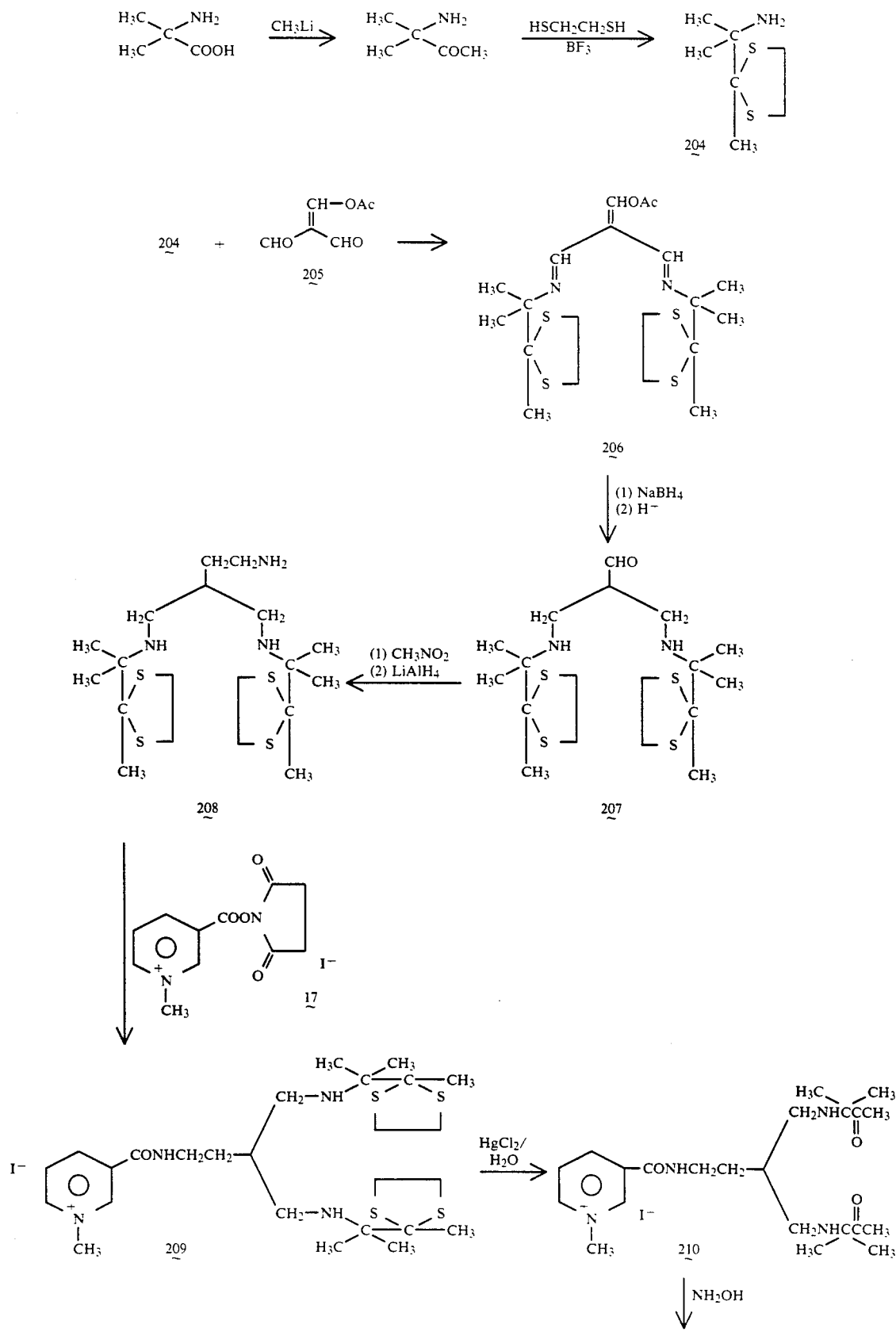

-continued
SCHEME 28
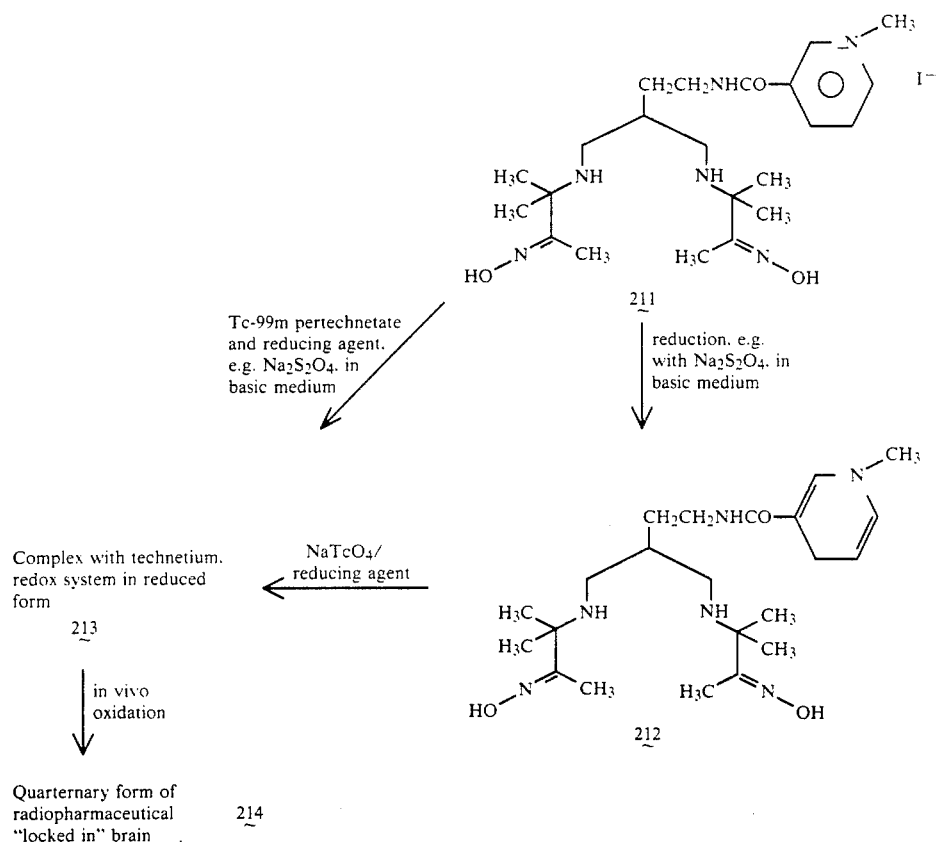
SCHEME 29
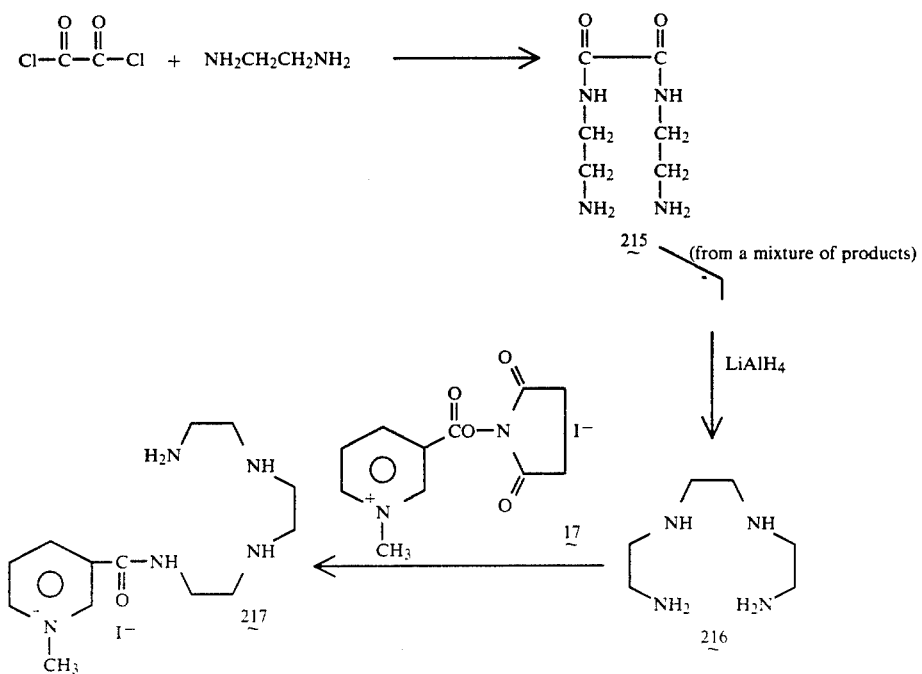

SCHEME 29 -continued

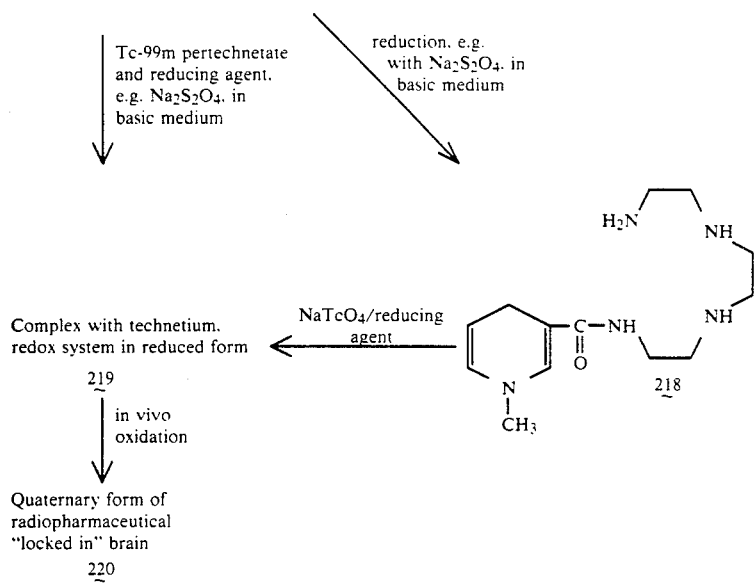

Thus, Scheme 1 above illustrates a typical synthetic route for compounds in which the linkage between the carrier and chelate portions is through a —COOH function in the chelating agent. In the first step, the alcohol reactant can be represented generally as HO—Z'—I wherein Z' is $C_1$-$C_8$ straight or branched alkylene; in the second step, the depicted reactant, nicotinamide, could be readily replaced with picolinamide, isonicotinamide, 3-quinolinecarboxamide, 4-isoquinolinecarboxamide or the like. (3-Quinolinecarboxamide and 4-isoquinolinecarboxamide can be prepared in known manner, e.g. by treating the corresponding acids with ammonia.) Other process variations will be apparent to those skilled in the art, particularly from the teachings of the aforementioned International Application PCT/US83/00725.

One such alternate approach to Scheme 1 is depicted in Scheme 2. In the first step of Scheme 2, the alcohol reactant (prepared by reacting 2-iodoethanol with nicotinamide) could contain a shorter or longer alkylene bridge ($C_1$-$C_8$) than shown and the pyridinium portion could be replaced with an equivalent pyridinium carrier, prepared in analogous fashion. Thus, for example, in the first step, an alcohol of the formula

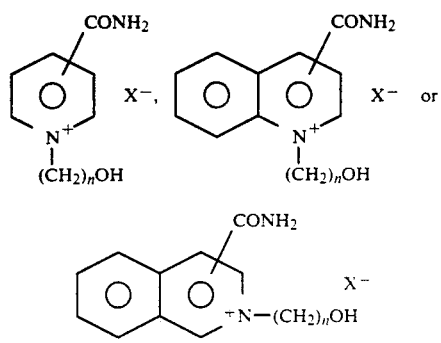

wherein n=1-8, preferably 1-3, can be reacted with 7 or other —COOH—containing chelating agent or precursor thereof. Alternatively, an alcohol of the formula

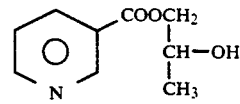

(prepared by reacting nicotinic acid with 1,2-propylene glycol in the presence of dicyclohexylcarbodiimide) or a position isomer or homologue thereof or corresponding derivative of a quinolinecarboxylic acid or an isoquinolinecarboxylic acid can be quaternized, e.g. by reaction with methyl iodide, and used in place of the alcohol reactant shown in Scheme 2. As yet another variation, bromoglucose can be reacted with nicotinamide, picolinamide or isonicotinamide or appropriate quinolinecarboxamide or isoquinolinecarboxamide to afford a starting alcohol of the formula

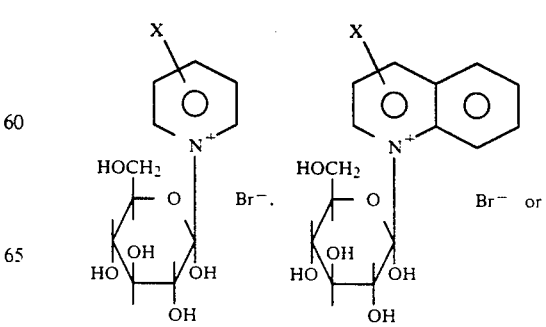

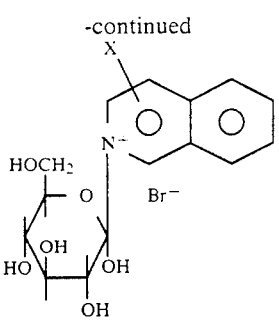

which can be used in place of the alcohol reactant used in the first step of Scheme 2. Still other variations would include reacting nicotinic acid or other suitable pyridine-ring containing acid with an appropriate di- or polyhydroxy compound such as ethylene glycol, propylene glycol, inositol or a simple sugar, linking the resultant intermediate via its free hydroxy group(s) to the carboxylic acid function of the chelating agent or the precursor thereof, and then quaternizing that intermediate.

Schemes 3 and 4 above are illustrative of the type of procedure utilized to prepare compounds in which the linkage between the carrier and chelate portions is through an —NH$_2$ or —OH function in the chelating agent or precursor thereof. The activated ester of nicotinic acid, 16, can of course be replaced with another activated ester of that or a similar pyridine-ring containing acid. Equivalent activated esters, e.g. an ester in which the

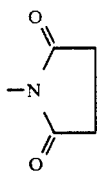

is replaced with

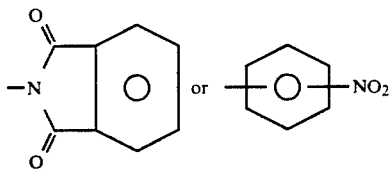

(especially p-nitrophenyl), will be apparent to those skilled in the art. The preparation of such esters proceeds according to known procedures, e.g. by reacting the acid chloride or anhydride or the acid in the presence of DCC with N-hydroxysuccinimide or other alcohol, then quaternizing the product, e.g. with methyl iodide or dimethylsulfate.

Scheme 5 illustrates another possible approach when the linkage between the carrier and chelate portions is through an —OH function in the chelating agent or its precursor. The first step in this sequence is described in Fritzberg U.S. Pat. No. 4,444,690; the resultant ethyl ester 30 is then reduced to the corresponding alcohol, using an appropriate reducing agent, e.g. LiAlH$_4$. The reduction thus introduces a —CH$_2$OH function in place of the acid function in 7. Other —COOH containing chelating agents or their precursors can be similarly converted to the corresponding —CH$_2$OH containing compounds. which can then be derivatized to the carrier-containing moieties as generally described hereinabove. One such derivatization is shown in Scheme 5. The conversions 31→32→33→34 parallel reactions shown in Scheme 2 hereinabove as well as in the Fritzberg patent. The carrier-containing moiety can readily be introduced into the structure after obtaining 34 by a variety of methods, e.g. by use of the activated quaternized ester 17 used in Schemes 3 and 4 or other activated ester; or by reaction with bromoacetyl chloride, followed by reaction with nicotinamide, isonicotinamide, 3-quinolinecarboxamide, picolinamide, 4-isoquinolinecarboxamide or the like to form 36 or similar derivative. Subsequent reduction to the dihydropyridine form as described herein and in International Application No. PCT/US83/00725 can be performed separately, or, more conveniently, can be accomplished at the same time as reduction of technetium to an appropriate oxidation state.

Scheme 6 illustrates a method of particular use when the linkage between the carrier and chelate portions is through an —NH— function which is part of an amide or imide or a very low pKa primary or secondary amine. Conversion of an ester group to the corresponding amide is accomplished with excess ammonium. Then the chelating agent precursor 42 having a —CONH$_2$ functional group is subjected to N-hydroxyalkylation, e.g. by reaction with an aldehyde [e.g. formaldehyde, benzaldehyde, acetaldehyde or chloral(Cl$_3$CCHO)]; thus, for example, in the case of chloral, the CONH$_2$ group becomes a

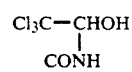

function and thus forms a suitable bridging group. The resultant compound is then subjected to any method described herein or in the aforementioned PCT application for linking the carrier to an —OH function. One such method, i.e. reacting the alcohol with nicotinic acid in the presence of dicyclohexylcarbodiimide, is shown in Scheme 6.

Scheme 7 is illustrative of a process in which the —NH— group to which the carrier is to be linked is part of an imide structure. The earliest steps of this Scheme are described in the aforementioned Fritzberg patent. Then, 51 is reacted with excess ammonia to form the corresponding succinamide which, when heated, loses ammonia to give the succinimide 52. That intermediate is then reacted with an aldehyde, as generally described in the preceding paragraph. and the resulting —OH containing group then derivatized, also as described previously.

Scheme 8 illustrates yet another alternate to Schemes 1 and 2; 3,4-diaminobenzoic acid is disclosed as a starting material for chelating agents in the Fritzberg patent. Scheme 8 follows the reaction sequence of Scheme 2 and could be varied in any of the many ways described in conjunction with Scheme 2 hereinabove. Moreover, 59 could alternatively be subjected to the reactions shown in Schemes 5 and 6 and/or discussed in connection with those Schemes; i.e. the —COOH group could be converted to a —CH$_2$OH or a —CONH$_2$ group and then derivatized as shown in and discussed with respect to those Schemes.

Schemes 9, 12 and 14 above illustrate typical conversion of a carboxylic acid ester group to the corresponding amide (—CONH$_2$); reduction of the amide function to the corresponding amine (—CH$_2$NH$_2$); reaction of the —NH$_2$ group with an activated ester of nicotinic acid; quaternization with methyl iodide; and reduction of the resultant quaternary of formula (I) to the corresponding dihydro of formula (II), or conversion of (I) directly to the formula (III) radiopharmaceutical. These processes can be varied as discussed in conjunction with Schemes 3, 4 and 5 above.

Schemes 10 and 15 above illustrate typical conversion of an alcohol (—CH$_2$OH), which may be obtained from the corresponding carboxylic acid ester, to the corresponding nicotinoyl ester; reaction of the ester derivative with methyl iodide to afford the desired formula (I) quaternary; and reduction to the corresponding formula (II) dihydro or conversion directly to the corresponding formula (III) radiopharmaceutical. For process variations, see the discussion of Schemes 3, 4 and 5 hereinabove.

In Scheme 11 above, there is shown a typical method for introducing a longer alkylene chain between an atom which is involved in forming the chelate structure and a pendant NH$_2$ group which is to be coupled to the carrier moiety. As depicted in this scheme, a secondary amino group

is reacted with a haloalkamide, e.g. BrCH$_2$CONH$_2$, replacing the hydrogen of the

with —CH$_2$CONH$_2$. Reduction of the amide affords the corresponding

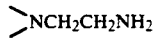

compound. That amine can then be reacted with an activated ester of nicotinic acid, followed by quaternization and reduction as in the other schemes. For variations, see in particular Schemes 3, 4 and 5 above.

Schemes 13 and 16 illustrate yet other methods for lengthening the alkylene chain, the chain here being interrupted by one or more oxygen atoms. Thus, a —CH$_2$OH group is typically converted to the corresponding lithium salt and then reacted with an iodoalkanol, e.g. ICH$_2$CH$_2$OH, to convert the —CH$_2$O—Li$^+$ group to a —CH$_2$OCH$_2$CH$_2$OH group. [Obviously, the chain could be lengthened by utilizing a longer-chain iodoalkanol, or by repeating the two steps just described (in which case additional intervening oxygen atoms would be introduced.)] The —CH$_2$OCH$_2$C-H$_2$OH group is then converted to the corresponding nicotinic acid ester, which is then quaternized to form the desired quaternary salt. Again, the reaction schemes can be varied as discussed with reference to Schemes 3, 4 and 5 hereinabove.

In Scheme 17 above, reaction of an —NH$_2$ group with an activated ester of nicotinic acid, followed by quaternization, is shown. The resultant formula (I) quaternary is then reduced as shown in the other schemes.

Many of the earliest steps in the reaction schemes depicted above parallel reactions described in Fritzberg U.S. Pat. No. 4,444,690. See, for example, the conversion of 7 to 30 in Scheme 10; the conversion of 30 to 40 to 41 in Scheme 12; the conversion of 111 to 112 to 113 to 114 in Scheme 13; and so on.

Scheme 18 above, like Scheme 11 which has already been discussed, shows another typical method for introducing a longer alkylene chain between the nitrogen atoms. Here the secondary amino group

is converted to the corresponding

group. The resultant amine can then be reacted with an activated ester of nicotinic acid, followed by quaternization and reduction as in the other schemes. As a preferred alternative in this and many of the other reaction schemes depicted herein, the quaternary chelating agent precursor of the invention can be prepared directly from reaction of the corresponding amine with a quaternized activated ester of nicotinic acid. Other variations will be apparent, e.g. from Schemes 3, 4 and 5 above.

Scheme 19 represents an alternate approach to the derivatives resulting from Scheme 1. Obviously, this scheme could be varied in a number of ways, most notably in the fourth step, where nicotinamide could be replaced with another amide (e.g. one of those discussed in Scheme 1) and where ICH$_2$CH$_2$OH could be replaced with another compound of the type I—Z'—OH where Z' is C$_1$–C$_8$ straight or branched alkylene.

Scheme 20 illustrates an alternate route to the derivatives of Scheme 8. This scheme represents a particularly attractive synthetic route to the protected quaternary derivative 62. Moreover, the intermediate 176 can be varied as discussed in conjunction with Scheme 19; also, this process can be adapted to the preparation of derivatives of other —COOH—containing chelating agents, e.g. those of Schemes 1 and 2.

In Scheme 21, the intermediate 179, prepared as in Scheme 20, is used to prepare yet other compounds of the invention derived from 3,4-diaminobenzoic acid.

Scheme 22 is illustrative of yet another variation in the procedure of Scheme 8. Scheme 22 can be readily adapted to the preparation of other derivatives of this invention; see, for example, the discussions of Schemes 8 and 20 above.

In Scheme 23, there are depicted two highly desirable alternate routes to the quaternary salt 76 of Scheme 9. These alternate routes utilize the quaternary activated esters of nicotinic acid to prepare the quaternary derivative 76 directly from the corresponding primary amine 74. Use of either the succinimidyl or the phthalimidyl quaternary intermediates (17 or 191) is illustrated. Other quaternary activated esters for use in this reaction will be apparent from the various processes described herein. After formation of the formula (I) quaternary such as 76, the process of Scheme 9 can then be used to prepare the other derivatives of this invention.

Scheme 24 depicts yet another highly desirable alternate route to the quaternary salt 76 of Scheme 9. In this particular preferred scheme, a protecting group is introduced prior to introduction of the carrier function; the protecting group is then removed prior to reduction of the quaternary function to the corresponding dihydro. In the case of the chelating agent shown in this scheme, reaction with acetone protects both the secondary amino and thiol functions by formation of thiazolidine structures so that those functions do not interfere during addition of the carrier moiety. Subsequently, the secondary amino and mercapto groups are regenerated by reacting the protected intermediate with mercuric chloride in an organic solvent such as methanol, conveniently at room temperature, and then decomposing the resulting complex with hydrogen sulfide. See, for example, British Patent Specification No. 585,250, which utilizes such a procedure for the production of esters of penicillamine. After preparing the quaternary salt 76 in this manner, the process of Scheme 9 can be used to prepare the other derivatives of this invention. Variations in the procedure used, e.g. as discussed in connection with Scheme 23, can be used to obtain yet other derivatives of the invention.

Scheme 25 represents an alternate route to the compounds obtained via Scheme 14. The route uses the preferred route of introducing the carrier moiety in its quaternary form and can be readily adapted to the preparation of derivatives of other —COOH containing chelating agents and/or introduction of other carrier moieties disclosed herein.

In Scheme 26, there is illustrated a process for attaching a

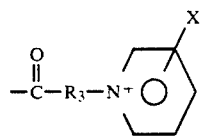

function or analogous carrier moiety to a pendant primary amine function in a chelating agent. This process utilizes the thiazolidine structure to protect the secondary amino and thiol functions in the particular chelating agent depicted, as fully discussed in conjunction with Scheme 24 above.

An alternate approach to the derivatives depicted in Scheme 26 is shown in Scheme 27, in which the primary amino group in the protected primary amine is first converted to the corresponding —NHCO—$R_3$—Br group, which is then reacted with nicotinamide or the like to afford the protected quaternary intermediate.

Scheme 27 depicts a process for preparing carrier-containing derivatives of yet another type of chelating agent. The desired chelating agent in this instance contains oxime functins, which are introduced after the quaternary form of the carrier has been attached. Formation of derivatives of yet another type of chelating agent is depicted in Scheme 29.

Similar schemes can be shown for the preparation of the other derivatives of this invention. The steps of introducing and removing protecting groups are only included when necessary. Also, the order of steps may be altered; in particular, quaternization may occur earlier in the reaction scheme, depending of course on the particular compounds involved. Other reaction schemes, reactants, solvents, reaction conditions, etc. will be readily apparent to those skilled in the art. Also, insofar as concerns the quaternary derivatives, when an anion different from that obtained is desired, the anion in the quaternary salt may be subjected to anion exchange via an anion exchange resin or, more conveniently, by use of the method of Kaminski et al., *Tetrahedron*, Vol. 34, pp. 2857–2859 (1978). According to the Kaminski et al method, a methanolic solution of an HX acid will react with a quaternary ammonium halide to produce the methyl halide and the corresponding quaternary X salt.

Reduction of the quaternary salt of formula (I) to the corresponding dihydro derivative of formula (II) can be conducted at a temperature from about −10° C. to room temeperature, for a period of time from about 10 minutes to 2 hours, conveniently at atmospheric pressure. Typically, a large excess of reducing agent is employed, e.g., a 1:5 molar ratio of reducing agent to starting compound of formula (I). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (II) is usually insoluble in water and thus can be readily separated from the reaction medium. In the case of sodium borohydride reduction, an organic reaction medium is employed, e.g., a lower alkanol such as methanol, an aqueous alkanol or other protic solvent. More typically, however, the quaternary of formula (I) is reduced in the same reaction mixture as the reduction of technetium to an appropriate oxidation state, affording the formula (III) radiopharmaceutical in one step from the formula (I) quaternary. Further details of the one-step reduction are given hereinbelow.

It will be apparent from the foregoing that a wide variety of derivatives of formulas (I) through (IV) can be obtained in accord with this invention. In a particularly preferred embodiment of this invention, however, there are provided novel chelating agent precursors of the formula

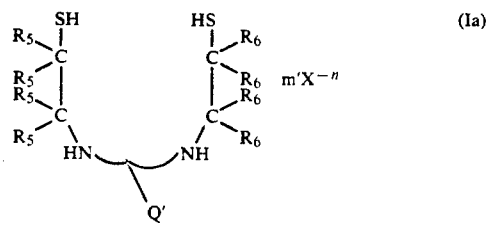

wherein each $R_5$ is independently selected from the group consisting of H and $C_1$–$C_7$ alkyl, or an $R_5$ can be combined with the adjacent

such that

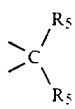

represents $$>C=O;$$

each $R_6$ is independently selected from the group consisting of H and $C_1$-$C_7$ alkyl, or an $R_6$ can be combined with the adjacent $$>C-R_6$$

such that $$>C<^{R_6}_{R_6}$$

represents $$>C=O; HN\diagdown\diagup NH$$
$$\phantom{>C=O; HN}Q'$$

is a radical of the formula $$HN\diagdown\phantom{XXX}\diagup NH$$
$$\phantom{HN}R_7\;R_7\;R_7\;(alk)_s-A'-[QC^+].$$

[structure: benzene ring with HN and NH substituents, and (alk)$_s$–A'–[QC$^+$]] or $$HN\diagdown\phantom{XX}\diagup NH$$
$$O=C\diagdown_N\diagup C=O,$$
$$\phantom{O=C}[QC^+]$$

wherein each $R_7$ is independently selected from the group consisting of H and $C_1$-$C_7$ alkyl; (alk) is a straight or branched lower alkylene group ($C_1$-$C_8$) which additionally may contain 1, 2 or 3 oxygen atoms in the chain, said oxygen atoms being nonadjacent to each other and also being nonadjacent to —A'—; X⁻ and n are as defined with formula (I); m' is a number which when multiplied by n is equal to one; s is zero or one; —A'— is —NH—, —COO—, —O—, —CONH—, $$-\underset{R_8}{\overset{|}{N}}-$$

wherein $R_8$ is $C_1$-$C_7$ alkyl, or $$-\underset{R_9}{\overset{|}{CON}}-$$

wherein $R_9$ is $C_1$-$C_7$ alkyl; when —A'— is —NH—, —O— or $$-\underset{R_8}{\overset{|}{N}}-,$$

then [QC⁺] is a radical of any one of formulas (a) through (j) hereinabove; when —A'— is —CONH— or $$-\underset{R_9}{\overset{|}{CON}}-$$

or when $$HN\diagdown\diagup NH$$
$$\phantom{HN}Q'$$

has the imide structure depicted above, then [QC⁺] is a radical of any one of formulas (k) through (s) hereinabove; and when —A'— is —COO—, then [QC⁺] is a radical of any one of formula (i) through (xiv) hereinabove. Preferably the salts of formula (Ia) have the partial structure $$\phantom{X}SH\phantom{XX}HS$$
$$H_2C\diagup\phantom{XX}\diagdown CH_2$$
$$O=C\phantom{XX}C=O,$$
$$HN\diagdown\diagup NH$$

$$H_3C\diagdown\phantom{X}SH\phantom{XX}HS\phantom{X}\diagup CH_3$$
$$H_3C\diagup C\diagdown\phantom{XX}\diagup C\diagdown CH_3\;\text{or}$$
$$\phantom{XX}H_2C\phantom{XXXX}CH_2$$
$$\phantom{XXX}HN\diagdown\diagup NH$$

$$\phantom{X}SH\phantom{XX}HS$$
$$H_2C\diagup\phantom{XX}\diagdown CH_2$$
$$H_2C\phantom{XXXX}CH_2$$
$$HN\diagdown\diagup NH$$

or are position isomers and/or homologs of the first two partial structures shown. It is also preferred that when $$HN\diagdown\diagup NH\;\text{is}\;HN\diagdown\phantom{XXX}\diagup NH$$
$$\phantom{HN}Q'\phantom{XXXXXXX}R_7\;R_7\;R_7\;(alk)_s-A'-[OC^-].$$

then each $R_7$ is preferably H and (alk) is preferably a $C_1$-$C_6$ alkylene group, or a $C_1$-$C_6$ alkylene group interrupted by an oxygen atom in the chain; and that when

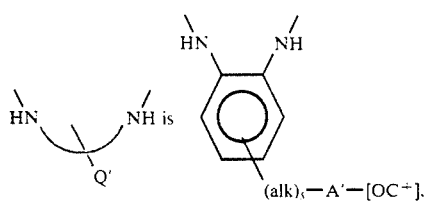

then (alk) is preferably a $C_1$-$C_6$ alkylene group, or a $C_1$-$C_6$ alkylene group interrupted by an oxygen atom in the chain. When

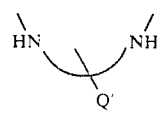

is either of the above, then the presently preferred values for —(alk)$_s$ —A'— are —COO—, —CH$_2$O—, —CONH—, —CH$_2$NH— and —CH$_2$OCH$_2$CH$_2$O—. Preferred values for [QC$^+$] in formula (Ia) are as given in conjunction with formula (I) hereinabove.

Corresponding to the preferred novel chelating agent precursors of formula (Ia) are the preferred novel chelating agents of the formula

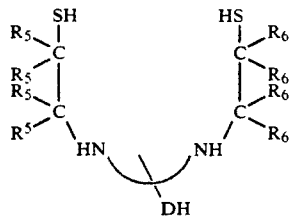

wherein $R_5$ and $R_6$ are as defined with formula (Ia) and

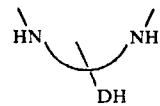

is a radical of the formula

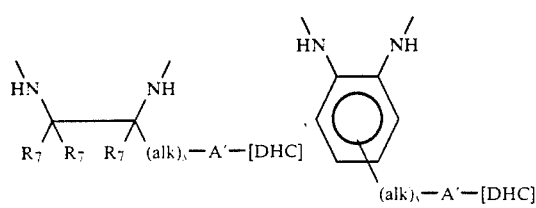

-continued

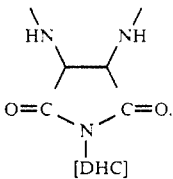

wherein $R_7$, (alk), s and —A'— are as defined with formula (Ia); when —A'— is —NH—, —O— or

wherein $R_8$ is $C_1$-$C_7$ alkyl, then [DHC] is a radical of any one of formulas (a') through (j'') hereinabove; when —A'— is —CONH— or

wherein $R_9$ is $C_1$-$C_7$ alkyl or when

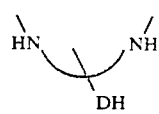

has the imide structure depicted above, then [DHC] is a radical of any one of formulas (k') through (s'') hereinabove; and when —A'— is —COO—, then [DHC] is a radical of any one of formulas (i') through (xiv'') hereinabove. Preferred compounds of formula (IIa) are the dihydro derivatives corresponding to the preferred compounds of formula (Ia).

Likewise preferred are the novel radiopharmaceuticals in which a formula (IIa) compound is chelated with a radioactive metal, especially with technetium. Especially preferred radiopharmaceuticals have the formula

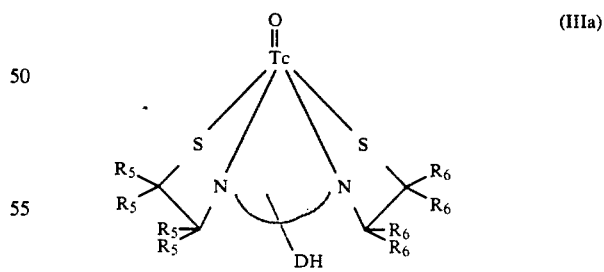 (IIIa)

wherein $R_5$ and $R_6$ are as defined with formula (Ia) and

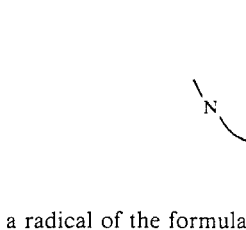

is a radical of the formula

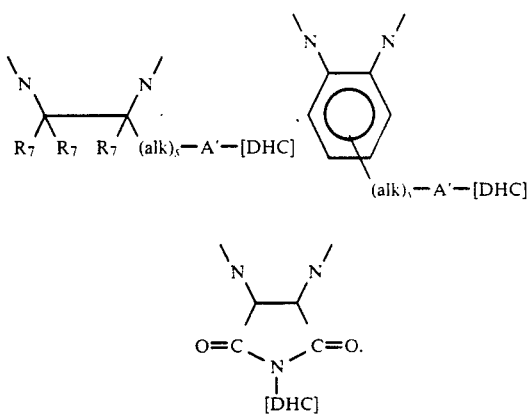

wherein $R_7$, alk, s and —A'— are as defined with formula (Ia) and [DHC] is as defined with formula (IIa) above; and the corresponding quaternaries, "locked in" the brain, especially those of technetium, which have the formula

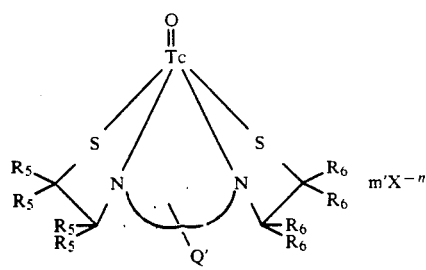
(IVa)

wherein $R_5$, $R_6$, m', $X^-$ and n are as defined with formula (Ia) and

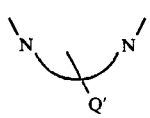

is a radical of the formula

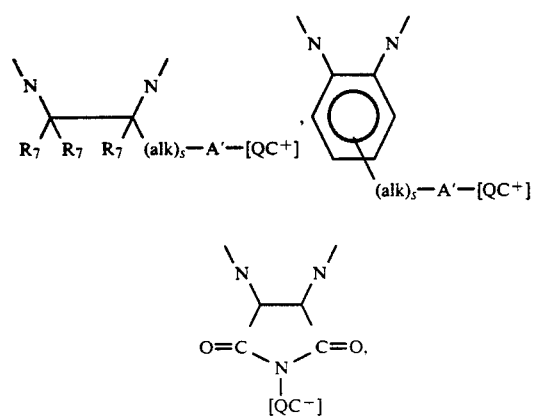

wherein $R_7$, alk, s, —A'— and [QC$^+$] are as defined with formula (Ia) above. The preferred complexes of formulas (IIIa) and (IVa) are those which correspond to the preferred derivatives of formulas (Ia) and (IIa).

Chelating agent precursors, chelating agents and radiopharmaceuticals within the purview of the present invention can also be prepared by reacting

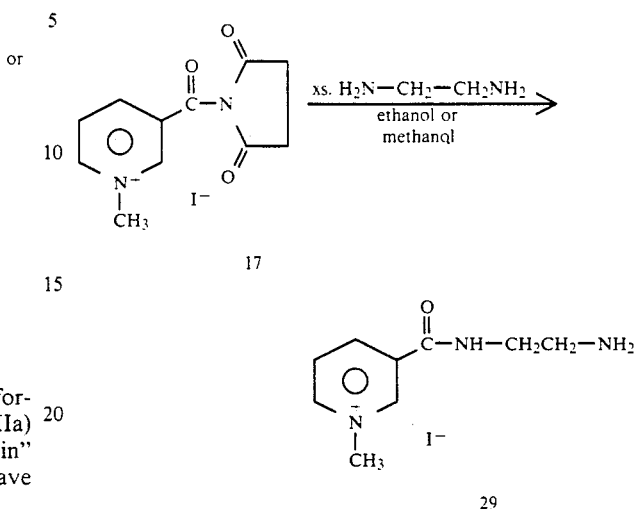

and thereafter reacting the amino group of the obtained compound 29 with the carboxyl group of compounds such as the 2-oxopropionaldehyde bis (thiosemicarbazone) derivatives having a free carboxyl group. Illustrative of such compounds is 3-carboxy-2-oxopropionaldehyde bis(N-methylthiosemicarbazone), a bifunctional chelating agent described in Yokoyama et al U.S. Pat. No. 4,287,362. The Yokoyama et al COOH— containing chelating agents also can be derivatized as generally described hereinabove for derivatizing COOH groups, e.g. as depicted in Schemes 1 and 2. Moreover, Yokoyama et al's chelating agents of the formula

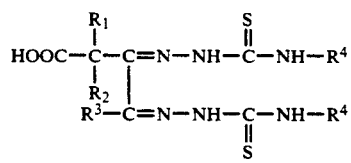

wherein $R^1$, $R^2$, $R^3$ and $R^4$ are each H or $C_1$-$C_3$ alkyl can be first converted to the corresponding esters (e.g. replacing —COOH with —COOC$_2$H$_5$), which can then be reduced to the corresponding alcohols (replacing —COOC$_2$H$_5$ with —CH$_2$OH) or converted to the corresponding amides; the alcohols or amides can then be converted to the corresponding carrier-containing derivatives; see, for example, the discussion of Schemes 9-16 above. Other process variations will be apparent from the many reaction schemes depicted hereinabove.

Another bifunctional chelating agent which can be readily converted to the redox system-containing chelating agent precursors, chelating agents and radiopharmaceuticals of this invention is a compound of the formula

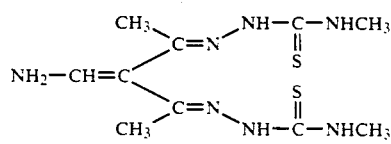

which is also known as amino DTS and which is described in the literature, e.g. in *Jap. J. Nucl. Med.* 19, 610 (1982). Amino DTS can be readily converted to the derivatives of the present invention by reacting it with an activated ester of nicotinic acid or the like and quaternizing the resulting ester to afford the corresponding precursor of formula (I), which can then be utilized as generally described herein to prepare the corresponding compound of formula (II) and radiopharmaceuticals of formulas (III) and (IV). See, for example, Scheme 30 below.

Yet another group of known chelating agents which is particularly well-suited for conversion to the redox system-containing chelating agent precursors, chelating agents and radiopharmaceuticals of the present invention can be represented by the formula

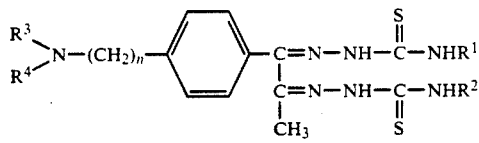

wherein $R^1$, $R^2$, $R^3$ and $R^4$ are each H or $C_1$-$C_3$ alkyl and n' is an integer of 0 to 3. See, for example, Yokoyama et al U.S. Pat. No. 4,511,550 and Australian Patent No. 533,722. An especially preferred chelating agent encompassed by this group is known as amino-PTS, or AEPM, and has the structure

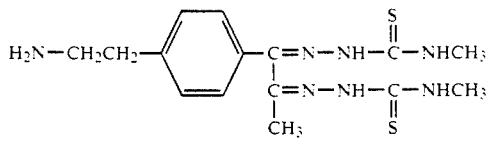

Amino-PTS can be converted to the derivatives of the present invention via the activated ester, as described supra in connection with amino-DTS. See, for example, Scheme 33 below. The exact structure of the resultant technetium complex 224 has not been determined; it is possible that the C=N and C=S bonds are also reduced during one of the reduction steps. One possible structure for 224 is as follows:

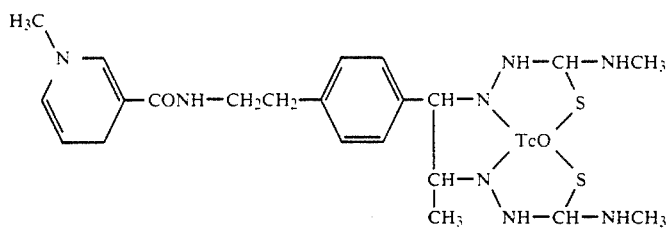

(A similar structure could be depicted for complex 165 of Scheme 30).

A preferred alternate route to derivatives of amino-PTS, amino-DTS and the like is illustrated by Schemes 31 and 32 below. This route reacts a quaternized activated ester with the ligand containing a primary amine group to form the quaternary chelating agent precursor of formula (I) in one step. Variations in this highly desirable single step, as well as in the two step alternative shown in Schemes 30 and 33, will be apparent from the discussion of a number of reaction schemes depicted hereinabove. Also, it should be pointed out that introduction of the carrier moiety in its quaternary form, typically via a quaternized activated ester such as 191 or 17, is generally advantageous over the two step method, and any of Schemes 6–7 and 9–17 hereinabove could be readily modified accordingly.

SCHEME 30

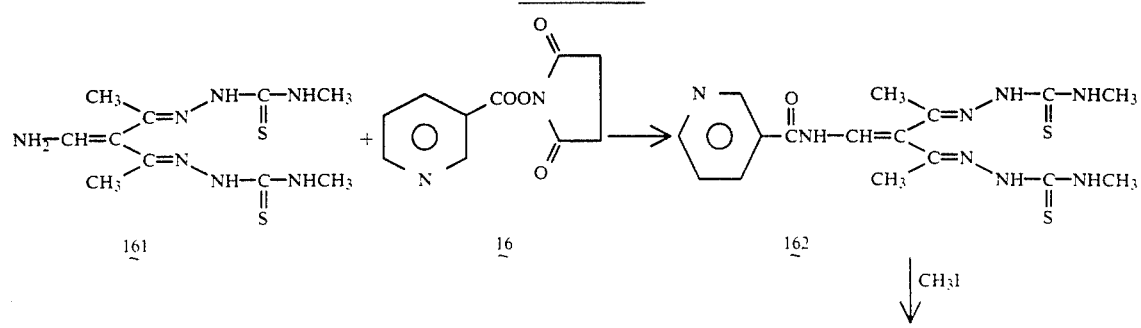

SCHEME 30

[amino DTS, a ligand described, for example, in Jap. J. Nucl. Med. 19, 610 (1982)]

-continued
SCHEME 30

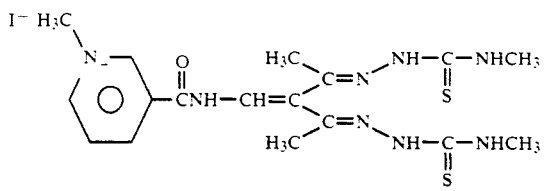

163

↘ Tc-99m pertechnetate and reducing agent, e.g. Na₂S₂O₄, in basic medium

↓ reduction, e.g. with Na₂S₂O₄, in basic medium

Complex of $^{99m}$TcO with reduced form of redox system

165

↓ in vivo oxidation

Quaternary form of radiopharmaceutical "locked in" brain

166

← NaTcO₄/reducing agent

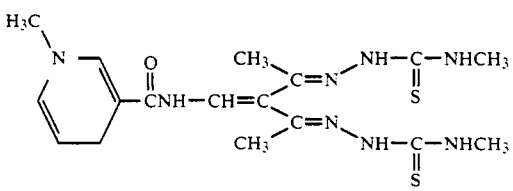

164

SCHEME 31

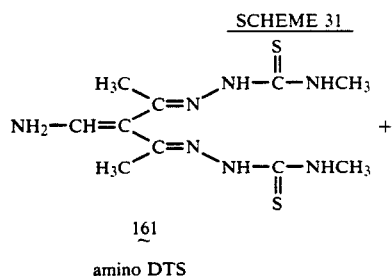

161
amino DTS

+

-continued
SCHEME 31

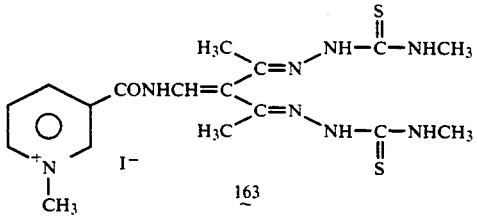

163

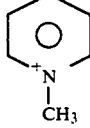

continue as in Scheme 30

166

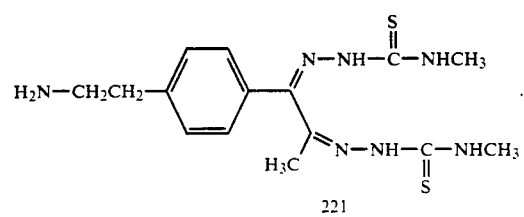

191

SCHEME 32

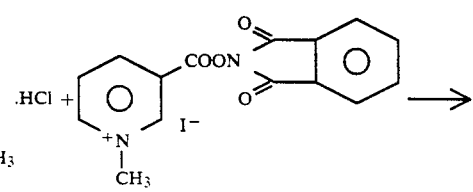

221

(a salt of amino PTS, described, for example in Yokoyoma et al U.S. Pat. No. 4,511,550 and Australian Patent No. 533,722)

.HCl +

191

-continued
SCHEME 32

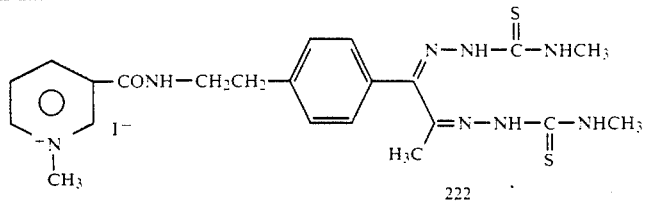

Tc-99m pertechnetate and reducing agent, e.g. Na$_2$S$_2$O$_4$, in basic medium ↙ reduction, e.g. with Na$_2$S$_2$O$_4$, in basic medium ↘

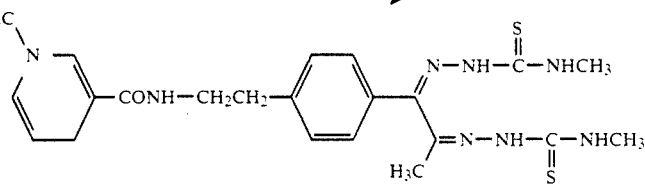

NaTcO$_4$/ reducing agent

Complex with technetium, redox system in reduced form ← 224 in vivo oxidation ↙

Quaternary form of radiopharmaceutical "locked in" brain
225

SCHEME 33

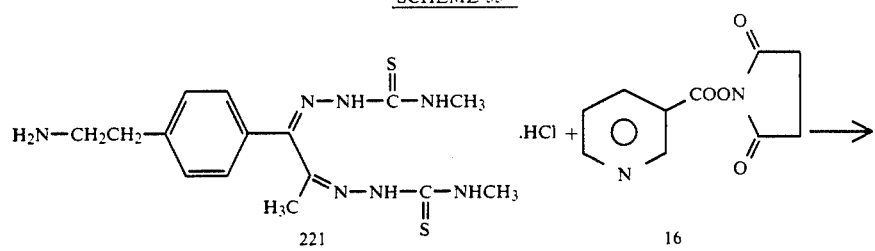

amino PTS (hydrochloride)

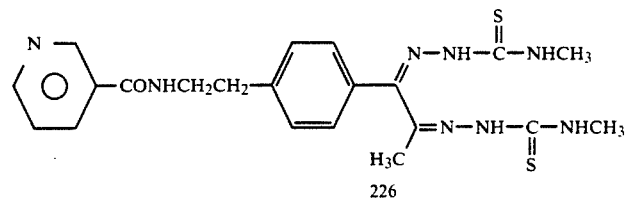

↙ CH$_3$I

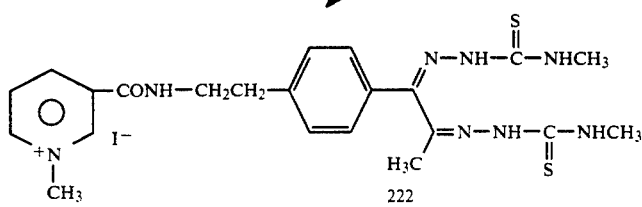

continue as in Scheme 32
↓
225

In a like manner, the presently contemplated carrier system can be incorporated into the structure of a novel technetium-99m radiopharmaceutical whose chelate portion is the residue of an amino- or hydroxy-substituted iminodiacetic acid, e.g., N-[3-(1-naphthyloxy)2-hydroxypropyl] iminodiacetic acid. Such substituted iminodiacetic acid chelating agents are known and are described in Loberg et al U.S. Pat. No. 4,017,596; such chelating agents can be protected to the extent necessary and then the trigonellinate or other carrier structure introduced through reaction with the —NH₂ or —OH group in the chelating agent.

Similarly, suitable chelating agents and their precursors that include a dihydropyridine⇌pyridinium salt carrier system can be prepared by reacting Compound 17 or the like with a chelating agent which is a substituted-alkyl monophosphonic acid such as aminobutylphosphonic acid, 1,5-diaminopentylphosphonic acid, and the like. Chelating agents of this general type are also known and are illustrated by those described in Köhler et al U.S. Pat. No. 3,976,762.

Yet other chelating agents containing one or two carboxyl functions are described in Fritzberg U.S. Pat. No. 4,444,690. Carrier-containing technetium chelates corresponding to the Fritzberg chelates can be prepared as generally described hereinabove and as illustrated by Schemes 1 and 2 above.

Fritzberg U.S. Pat. No. 4,444,690 describes an interesting series of 2,3-bis(mercaptoalkanoamide)alkanoic acid chelating agents of the general formula

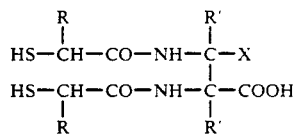

wherein X is H or —COOH, and R and R' are H or lower alkyl, and water-soluble salts thereof, used to prepare the corresponding radiopharmaceuticals of the formula

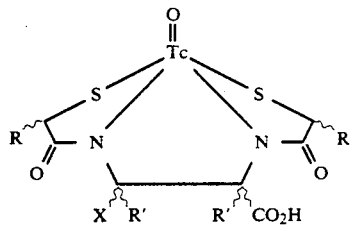

wherein X is H or —COOH, and R and R' are H or lower alkyl. The Fritzberg chelating agents are prepared from the corresponding 2,3-diaminoalkanoic acids by esterification with a lower alkanol containing dry HCl, followed by treating the resultant alkyl ester with a chloroalkanoyl chloride to form the bis(-chloroalkanomide)ester, followed by treating that ester with

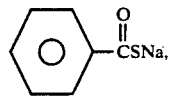

followed by alkaline hydrolysis of the resultant 2,3-bis(-benzoylmercaptoalkanoamido)alkanoic acid ester to produce the 2,3-bis(mercaptoalkanoamido)alkanoic acid chelating agent. Preparation of an analog from 3,4-diaminobenzoic acid is also disclosed by Fritzberg. Many of Fritzberg's synthetic steps can be adapted to produce the formula (I) derivatives of this invention in which, in place of the —COOH group in Fritzberg's chelating agent, there is an $(alk)_r$—A'—[QC$^+$] group wherein the structural variables are as defined with formula (Ia) hereinabove. See, for example, Schemes 12, 13 and 16 above.

Radiopharmaceuticals containing a dihydropyridine⇌pyridinium salt carrier system can also be prepared using a novel chelating agent precursor obtained by reacting, in pyridine as the solvent, the aforementioned Compound 29 with nitrilotriacetic anhydride according to the known general procedure illustrated in Nunn et al U.S. Pat. No. 4,418,208.

The dicarboxyl pyridinium salt obtained from the above reaction is obtained in purified form as follows: The volatile components of the reaction mixture are evaporated to an oily semisolid on a rotary evaporator. A solution of 10 percent aqueous sodium hydroxide (w/v) is used to dissolve the oily semisolid. The resulting solution is extracted with methylene chloride to remove the remaining pyridine from the aqueous phase. The pH value of the aqueous phase is thereafter lowered to a value of about 6-8. The resulting aqueous solution is then reduced in volume to about that of the original pyridine solution, and about five times that volume of a saturated solution of picric acid is added to form a picrate derivative precipitate.

The picrate precipitate is washed with cold, distilled water, and is then dissolved in a 10 percent aqueous solution of hydrochloric acid (v/v). The resulting solution is extracted with methyl chloride until there is no more yellow color in the aqueous or methylene chloride phases. The resulting, colorless aqueous phase is concentrated to about the volume of the original pyridine solution, and is then lyophylized to provide the chelating agent in dry form. The dried chelating agent is then dissolved in ethanol and precipitated using the diethyl ether flooding technique described in Example 4 hereinbelow.

Still another useful chelating agent precursor can be prepared by reacting equimolar quantities of ethylenediaminetetracetic acid and acetic anhydride in dry pyridine following the teachings of Nunn et al U.S. Pat. No. 4,418,208, and thereafter reacting a further equimolar amount of Compound (29) to form the monoamide adduct. The tridentate chelating agent salt is obtained as described immediately above.

The tridentate chelating agent precursor salt so obtained is thereafter reacted with the 99m pertechnate ion as described in Example 5 below, which reduces both the technetium and the pyridinium salt, to form a 1:1 ligand:radioactive metal ion complex drug delivery system of this invention. The complex so formed is ionically neutral inasmuch as the five valences of the reduced technetium-99m metal are taken up with one oxygen atom and three carboxylate oxygens, and the pyridinium ring is in its reduced, dihydropyridine form.

As aforesaid, the preparation of the chelating agent precursors, chelating agents and radiopharmaceuticals of this invention must be tailored to the particular starting materials used, especially as regards the presence of reactive functional groups in addition to the group which is to be linked to the carrier moiety. The stage at which the carrier is introduced and the manner in which the carrier is introduced will be determined accordingly. Often the carrier must be introduced in quaternary form at an early stage of the synthesis as illustrated hereinabove. When not so required, it may be more desirable to react an appropriate starting material such as nicotinic anhydride with an NH₂— or OH— containing ligand or ligand precursor, and quaternize at a later stage, after coupling the ligand (chelating agent) and the 3-pyridinecarbonyl group.

The processes depicted above are only intended to be illustrative. Many variations, for example, can be made in the chelating portions of the molecule, and such variations will naturally affect the synthetic scheme, particularly as regards the necessity for introducing protecting groups and subsequent removal thereof.

In order to further illustrate the present invention and the advantages thereof, the following specific examples are given, it being understood that same are intended only as illustrative and in no wise limitative.

EXAMPLE 1

N-(t-butoxycarbonyl),N-(2-mercaptoethyl)glycyl N'-(2-aminoethyl)homocysteinamide (Compound 14 of Scheme 3)

N-(t-butoxycarbonyl),N-(2-mercaptoethyl)glycyl homocysteine thiolactone (13) is prepared as described in Examples 1 and 2 of Byrne et al U.S. Pat. No. 4,434,151, and is dissolved (1.0 gram; 3 millimoles) in 25 milliliters of tetrahydrofuran (THF). The resulting solution is then cooled to about 0° C., and ethylenediamine (1.8 grams; 30 millimoles) is added to form a new solution. The resulting new solution is maintained for about one hour. The volatile components of the solution are thereafter removed with a rotary evaporator. n-Butanol (about 10 milliliters) is added to the "dried" solution components and the liquid components of the resulting composition are again removed by rotary evaporation. The last step is repeated until the vapors remaining in the evaporation vessel do not cause a moistened pH-indicator paper to indicate a basic pH value, thereby also indicating that the ethylenediamine has been substantially removed and that the N-(t-butoxycarbonyl),N-(2-mercaptoethyl)glycyl N'-(2-aminoethyl)-homocysteinamide so obtained is substantially pure.

EXAMPLE 2a

Succinimidyl nicotinate (Compound 16 of Scheme 3)

Nicotinic acid (12.3 g; 0.1 mole) and N-hydroxysuccinimide (11.5 g; 0.1 mole) are dissolved in 300 milliliters of hot dioxane. The mixture is cooled on an ice-bath and dicyclohexylcarbodiimide (20.6 g; 0.1 mole) in 30 milliliters of dioxane is added. The reaction mixture is stirred, with cooling, for approximately three hours, then refrigerated for at least 2 hours. The precipitated dicyclohexylurea is removed by filtration, the solution is condensed under vacuum, and the yellowish solids which precipitate are recrystallized from ethyl acetate. White crystals (14 g) of succinimidyl nicotinate are obtained (Yield 63.6%). Structure of the product is confirmed by NMR.

EXAMPLE 2b

Succinimidyl Trigonellinate (Compound 17 of Scheme 3)

Succinimidyl nicotinate 16 (3.3 g; 15 mmole) is dissolved in 50 milliliters of dioxane and 3.7 milliliters (8.2 g; 60 mmole) of methyl iodide is added. The reaction mixture is refluxed for about 48 hours. The yellow crystals which precipitate during the reaction are removed by filtration, washed with ethyl ether and dried under vacuum at 40° C. Succinimidyl trigonellinate (5.2 g) is obtained (Yield 96.3%). Structure of the product is confirmed by NMR.

An improved method for preparing Compound 17 is as follows:

A solution of 9.0 g (41 mmol) of the ester 16 and 11.6 g (82 mmol) of methyl iodide in 40 mL of anhydrous acetone is heated in a pressure bottle under an argon atmosphere for 16 hours. The yellow precipitate which forms is removed by filtration. Yield 14 g of Compound 17, darkening at 170° C. and melting at 197° C.

EXAMPLE 3

N-(t-butoxycarbonyl), N-(2-mercaptoethyl)glycyl N'-[1-methyl-3-(2-N-ethyl)carbamoylpyridinium iodide]homocysteinamide (Compound 18 of Scheme 3)

N-(t-butoxycarbonyl), N-(2-mercaptoethyl)glycyl N'-(2-aminoethyl)homocysteinamide—Compound 14—(1.12 grams; 0.003 mole) and succinimidyl trigonellinate—Compound 17—(0.70 gram; 0.0025 mole) are dissolved in 25 milliliters of dry pyridine with stirring. An appropriately sized, "micro" Dean-Stark trap and condenser are added to the reaction flask and the solution is heated to and maintained at a temperature of 80° C. until substantially all of the succinimidyl ester is replaced. The pyridine is removed on a rotary evaporator using n-butanol as a "chaser" as described before for the ethylenediamine removal. Once the pyridine is removed, the dried residue is triturated with THF and the solid is removed by filtration and washed several times with THF with care not to dry by air suction. The solid so obtained is thereafter dried in vacuo to provide Compound 18, N(t-butoxycarbonyl), N-(2-mercaptoethyl)glycyl N'-[1-methyl-3-(2-N-ethyl)carbamoylpyridinium iodide]homocysteinamide.

EXAMPLE 4

N-(2-mercaptoethyl)glycyl N'-[1-methyl-3-(2-N-ethyl)-carbamoylpyridinium iodide]homocysteinamide (Compound 19 of Scheme 3)

N-(t-butoxycarbonyl), N-(2-mercaptoethyl)glycyl N'-[1-methyl-3-(2-N-ethyl)carbamoylpyridinium iodide]homocysteinamide—Compound 18—(1.24 grams; 0.002 mole) is dissolved with stirring in absolute ethanol (50 milliliters) and cooled to about 0° C. in an ice-water bath. HCl gas is bubbled through the stirred solution for 15 minutes, and the solution is thereafter stirred for an additional 15 minutes. Diethyl ether (200 milliliters) is thereafter added to the solution to precipitate the salt. The precipitate is filtered and washed with diethyl ether with care not to dry the precipitate by air suction. The solid is then dried in vacuo to provide N-(2-mercaptoethyl)glycyl-N'-[1-methyl-3-(2-N-ethyl)-carbamoylpyridinium iodide]homocysteinamide.

EXAMPLE 5

Complex Between N-(2-mercaptoethyl)glycyl-N'-[1-methyl-3-(N-2-ethyl)-carbamoyl-1,4-dihydropyridyl]homocysteinamide and the Oxotechnate-99 m ion (Compound 20 of Scheme 3)

N-(2-mercaptoethyl)-glycyl-N'-[1-methyl-3-(2-N-ethyl)carbamoylpyridinium iodide]homocysteinamide—Compound 19—(89 milligrams; 0.17 millimole) is dissolved in 1.0 milliliter absolute ethanol and 1.0 milliliter of 1N NaOH. A 1.0 milliliter generator eluant of $^{99m}TcO_4^-$ (5 to 50 milliCuries) in saline is added. Then, 0.5 milliliter of dithionite solution, prepared by dissolving 336 milligrams of $Na_2S_2O_4$ per milliliter of 1.0 NaOH, is added and the mixture heated sufficiently to reduce both the technetium and the pyridinium salt and to form the complex between N-(2-mercaptoethyl)glycyl-N'-[1-methyl-3-(N-ethyl)caramoyl-l4-dihydropyridyl]homocysteinamide and the oxotechnate-99 m ion. The complex so prepared is buffered by the addition of 1.0 milliliter of 1N HCl and 4.0 milliliter of 0.1 molar $NaH_2PO_4$, pH 4.5 buffer.

EXAMPLE 6

Complex Between
N-(2-mercaptoethyl)glycyl-N'-[1-methyl-3-(N-2-ethyl)-carbamoyl-1,4-dihydroquinolyl]homocysteinamide and the Oxotechnate-99 m ion A radiopharmaceutical coupled to a carrier based upon a reduced, dihydroquinoline carrier such as the title complex can be prepared following the steps outlined in Examples 1–5, but replacing the nicotinic acid in Example 2a with an equivalent quantity of 3-quinolinecarboxylic acid.

EXAMPLE 7

N-[2-(acetamidomethyl)mercaptopropionyl]glycyl N'-(2-aminoethyl)homocysteinamide (Compound 25 of Scheme 4)

N-[2-(S-acetamidomethyl)mercaptopropionyl]glycyl homocysteine thiolactone (Compound 24 of Scheme 4), prepared as described in Examples 7 and 9 of Byrne et al U.S. Pat. No. 4,434,151, is suspended (1.0 gram; 3 millimoles) in 25 milliliters of THF. The resulting suspension is cooled to a temperature of about 0° C. in an ice-water bath, and ethylenediamine (1.8 grams; 30 millimoles) is added to form a new solution. N-[2-(acetamidomethyl) mercaptopropionyl]glycyl N'-(2-aminoethyl)homocysteinamide is thereafter obtained in a manner substantially similar to that described in Example 1 for the analogous compound.

EXAMPLE 8

N-[2-(acetamidomethyl)mercaptopropionyl]glycyl N'-[1-methyl-3-(2-N-ethyl)carbamoylpyridinium iodide]homocysteinamide (Compound 26 of Scheme 4)

Compound 26 of synthetic Scheme 4 is obtained in a manner analogous to that used in Example 3 to prepare Compound 19, but Compounds 17 and 25 are utilized as starting materials.

EXAMPLE 9

Complex Between
N-(2-mercaptopropionyl)glycyl-N'-[1-methyl-3-(2-N-ethyl)carbamoyl-1,4-dihydropyridine]homocysteinamide and the Oxotechnate-99m ion—(Compound 27 of Scheme 4)

Compound 26 of Example 8 (0.17 millimole) is dissolved in 1.0 milliliter of absolute ethanol and 1.0 milliliter of 1N NaOH. The complex of this Example is thereafter prepared in a manner analogous to that described for the complex of Example 5. Here, the basic solution frees the 2-mercaptopropionyl group from its protective N-methylene acetamido group, while the dithionite reduces both the pyridinium and technetium salts.

EXAMPLE 10

3,4-dithia-2,2,5,5-tetramethylhexane-1,6-dione (Compound 68 of Scheme 9)

To a stirred solution containing 115.6 g (1.6 mol) of isobutyraldehyde 67 in 184 g of carbon tetrachloride are added dropwise, at 40°–50° C., 108 g (0.8. mol) of 97% sulfur monochloride. The addition is carried out during a 2.5 hour period, under a nitrogen atmosphere, with occasional cooling. The solution is maintained at 30°–45° C., with stirring, for an additional 48 hour period, under a current of nitrogen, to remove the hydrogen chloride liberated. The solution is distilled under vacuum to give 72 g of the desired 3,4-dithia-2,2,5,5-tetramethylhexane-1,6-dione, i.e. Compound 68 of Scheme 9. $^1H$ NMR($CDCl_3$) δ9.1(s,2-C$\underline{H}$O), 1.4[s,12,—C(C$\underline{H}_3$)$_2$—].

EXAMPLE 11

Ethyl 2,3-(diammonium)propionate dichloride (Compound 70 of Scheme 9)

To 10 g (0.07 mol) of ethyl cyanoglyoxylate-2-oxime 69 are added 125 mL of absolute ethanol, 15 g of hydrogen chloride gas and 1 g of platinum oxide. The mixture is hydrogenated using a Parr-hydrogenation apparatus. Hydrogen uptake is complete in 3 hours. The product is removed by filtration and taken up in 75 mL of hot 95% ethanol. The ethanol solution is filtered. The filtrate is then cooled and the crystalline product which separates on standing is removed by filtration. There is thus obtained ethyl 2,3-(diammonium)propionate dichloride, i.e. Compound 70 of Scheme 9. Yield 5 g (35%), melting point 164°–166° C. (lit. 164.5°–165° C.); $^1H$ NMR($D_2O$) δ4.5(m,3,—NCHCO—, —OC$\underline{H}_2$CH$_3$). 3.5(m,2,—NC$\underline{H}_2$CH—), 1.3(t,3,—OCH$_2$C$\underline{H}_3$).

EXAMPLE 12

5,8-diaza-1,2-dithia-6-ethoxycarbonyl-3,3,10,10-tetramethylcyclodeca-4,8-diene (Compound 71 of Scheme 9)

Procedure I

To 1.0 g (5 mmol) of the bisaldehyde 68 is added dropwise a solution of 1.0 g (5 mmol) of the ester 70 and 0.9 mL of pyridine in 30 mL of methanol at 0° C. while under a nitrogen atmosphere. The addition takes place during a 10 minute period. The solution is then allowed to stand for 1 hour, after which time 10 mL of water is added. The solution turns turbid and warms to 26° C. The solution is stirred for an additional 20 minute period, after which time the white precipitate which forms settles out of solution. The precipitate is removed by filtration and then taken up in chloroform. The chloroform solution is dried over sodium sulfate. Removal of the solvent and trituration of the residue with petroleum ether gives white plate-like crystals of the desired product, 5,8-diaza-1,2-dithia-6-ethoxycarbonyl-3,3,10,10-tetramethylcyclodeca-4,8-diene, i.e. Compound 71 of Scheme 9, in 53% yield (1 g), melting point 98°–99° C. IR (thin film) 3450, 1740, 1650 cm$^{-1}$; $^1H$ NMR($CDCl_3$) δ6.9(m,2,C—N=C$\underline{H}$—), 3.0–4.6(m,5,—OC$\underline{H}_2$CH$_3$, —NC$\underline{H}_2$C$\underline{H}$—N—), 1.5[m,15,2 $\diagup\!\!\!\diagdown$C(C$\underline{H}_3$)$_2$.

—OCH$_2$C$\underline{H}_3$].

Procedure II

To 1.0 g (5 mmol) of the bisaldehyde 68 in 10 mL of methanol is added dropwise 1.0 g (5 mmol) of the ester 70 and 1 g (12 mmol) of sodium bicarbonate in 20 mL of a 50:50 by volume mixture of methanol and water. The mixture is stirred at 0° C. for 10 minutes, after which time 10 mL of water is added. The resultant mixture is maintained at room temperature, with stirring, for 2 hours. Water is added until the white precipitate which forms separates out of solution. The precipitate is removed by filtration and taken up in chloroform. Removal of the solvent by rotary evaporation affords 0.4 g (21% yield) of Compound 71, having a melting point and $^1$H NMR spectrum identical to the product of Procedure I.

Procedure III

A solution of 8 g of the ester 70 and 7 mL of pyridine in 200 mL of methanol is added dropwise over a two hour period to a solution of 8 g of bisaldehyde 68 in 25 mL of methanol. The reaction mixture is cooled in an ice bath after the addition for 1 hour, then is allowed to remain at room temperature for 1 hour. The reaction mixture is then placed in a freezer (−20° C.) overnight. The solution is concentrated to one-third volume, water is added and the aqueous solution is extracted with chloroform. The chloroform extract is washed with saturated aqueous sodium chloride solution and dried over magnesium sulfate. Removal of the solvent leaves a viscous mass, which is dissolved in 20 mL of hexane. The hexane solution is cooled in an acetone/dry ice bath until a white powder separates. The product is removed by filtration and taken up in chloroform. The chloroform solution is concentrated. White crystals of Compound 71 are formed on standing. Yield 7 g, melting point 95°–96° C. NMR and IR as in Procedure I.

EXAMPLE 13

6-carbamoyl-5,8-diaza-1,2-dithia-3,3,10,10-tetramethylcyclodeca-4,8-diene (Compound 72 of Scheme 9)

Procedure I

A solution of 5 g of the ester 71 in 20 mL of tetrahydrofuran and 20 mL of aqueous ammonia is stirred at room temperature for 2 hours, after which time it is allowed to stand at room temperature for 24 hours. Removal of solvent leaves a white powder which is removed by filtration. The product, 6-carbamoyl-5,8-diaza-1,2-dithia-3,3,10,10-tetramethylcyclodeca-4,8-diene, i.e. Compound 72 of Scheme 9, is crystallized from a mixture of isopropanol and water. Yield 4 g (88%), melting point 181°–183° C. IR (KBr) 3300, 3100, 1650 cm$^{-1}$; $^1$H NMR(CDCl$_3$) δ7.0(m,2, —H$\underline{C}$=N—), 6.4(broad band,2, —CON$\underline{H}_2$), 3,8–4.6[m,3, —N$\underline{C}$-$\underline{H}_2$—C$\underline{H}$(N—)CO—], 1.5, 1.4[s,12, $>$C(C$\underline{H}_3$)$_2$].

Procedure II

A solution of 5 g of the ester 71 in 20 mL of tetrahydrofuran, 20 mL of ethanol and 20 mL of aqueous ammonia (28%) is stirred at room temperature for 16 hours. Removal of the solvent leaves Compound 72 as a white powder, which crystallizes from toluene as white plates. Yield 4 g, melting point 193°–194° C. IR and NMR as in Procedure I.

EXAMPLE 14

5-carbamoyl-5,8-diaza-1,2-dithia-3,3,10.10-tetramethylcyclodecane (Compound 73 of Scheme 9)

To 3.7 g of the amide 72 in 25 mL of 95% ethanol is added 2 g of sodium borohydride. The mixture is stirred at room temperature for 2 hours, then is heated at reflux for 2 hours. The solution is thereafter concentrated in vacuo and water is added to precipitate the product. The white crystalline product is removed by filtration. Recrystallization from a mixture of isopropanol and water affords 6-carbamoyl-5,8-diaza-1,2-dithia-3,3,10,10-tetramethylcyclodecane, i.e. Compound 73 of Scheme 9, as fine white needles melting at 138°–139° C. Yield 3 g. $^1$H NMR(CDCL$_3$) δ2.3–4.0[m,7, —NC$\underline{H}_2$-C$\underline{H}$—N—, 2—NC$\underline{H}_2$—C(CH$_3$)—S—], 1.8(broad band, 2,$^-$—CON$\underline{H}_2$), 1.3[m,14, C(C$\underline{H}_3$)$_2$, —CN$\underline{H}$—CH$_2$—].

EXAMPLE 15

5-aminomethyl-4,7-diaza-2,9-dimethyldecane-2,9-dithiol (Compound 74 of Scheme 9)

A solution of 1.8 g of the amide 73 in 50 mL of dry tetrahydrofuran is added dropwise to a slurry of 1 g of lithium aluminum hydride in 100 mL of dry tetrahydrofuran. The addition takes place over a 30 minute period. The mixture is then heated at the reflux temperature for 20 hours. At the end of that time, the reaction mixture is first cooled and then quenched with saturated Na-K tartrate solution. The aqueous phase is extracted with chloroform. The combined organic phase is then dried over sodium sulfate. Removal of the solvent by rotary evaporation affords, as a viscous oil, 5-aminomethyl-4,7-diaza-2,9-dimethyldecane-2,9-dithiol, i.e. Compound 74 of Scheme 9; $^1$H NMR (CDCl$_3$) δ2.8[m,9—NC$\underline{H}_2$C$\underline{H}$—C(C$\underline{H}_2$)N$\underline{H}$—, 2—NC-$\underline{H}_2$—C(CH$_3$)$_2$S$^-$—], 1.5[m,14, $>$C(C$\underline{H}_3$)$_2$,—SH].

EXAMPLE 16

5,8-diaza-1,2-dithia-3,3,10,10-tetramethylcyclodeca-4,8-diene (Compound 87 of Scheme 11)

To 3.15 g of the dialdehyde 68 is added 4.0 g of ethylenediamine, with stirring and cooling, over a period of 10 minutes. The thick mass which results is stirred for an additional one minute period, then allowed to stand for 1 hour at room temperature and subsequently cooled for 16 hours in a freezer (−20° C.). The solid is removed by filtration and washed with 500 mL of water. The white product is then taken up in chloroform and the chloroform solution is dried over sodium sulfate. Removal of the chloroform gives 2.5 g of 5,8-diaza-1,2-dithia-3,3,10,10-tetramethylcyclodeca-4,8-diene, i.e. Compound 87 of Scheme 11, as a white crystalline product, melting at 168°–170° C. (lit. 162°–164° C., 163°–166° C.). $^1$H NMR(CDCl$_3$) δ6.9(s,2, —H$\underline{C}$=N—), 4.2,3.0(doublet of doublet, 2, 2—C$\underline{H}_2$—C$\underline{H}_2$), 1.40[s,6,—C(C$\underline{H}_3$)$_2$—]. Anal. Calcd. for C$_{10}$C$_{18}$N$_2$S$_2$: C, 52.13; H, 7.88; N, 12.16; S, 27.83. Found: C, 52.20; H, 7.90; N, 12.14; S, 27.74.

EXAMPLE 17

5,8-diaza-1,2-dithia-3,3,10,10-tetramethylcylodecane (Compound 88 of Scheme 11)

A solution of 0.5 g of 87 and 0.3 g of sodium borohydride in 23 mL of ethanol is stirred at room temperature for 1 hour, then is heated at the reflux temperature for 20 minutes. Then, 10 mL of water are added and the mixture is heated for an additional 10 minutes. The solvent is partially removed by rotary evaporation and the residue is extracted three times with 10 mL portions of chloroform. The chloroform extract is dried over sodium sulfate and the solvent is removed by rotary evaporation. The resultant liquid solidifies on cooling. Flash chromatography (eluent hexanes/dichloromethane/isopropanol 5:1:1 by volume) gives 5,8-diaza-1,2-dithia-3,3,10,10-tetramethylcyclodecane, i.e. Compound 88 of Scheme 11, as a solid, melting at 52°–53° C. $^1$H NMR(CDCl$_3$) $\delta$3–2.1(m,10 ring protons), 1.1,1.2(s,6 C$\underline{H}_3$, C$\underline{H}_3$).

EXAMPLE 18

N-[(4,7-diaza-2,9-dimercapto-2,9-dimethyldec-5-yl)methyl]nicotinamide (Compound 75 of Scheme 9)

A solution of 9 mmol of the activated ester 16 in 30 mL of dimethoxyethane is added dropwise over a period of one hour to 8.4 mmol of the amine 74 in 70 mL of dimethoxyethane. Thin layer chromatography after one hour, using a solvent system of petroleum ether/acetone/dichloromethane/isopropyl alcohol (10:5:5:1 by volume), indicates a major component has been obtained. The solvent is removed by evaporation and the residue is treated with water. The resultant mixture is extracted with chloroform and dried over sodium sulfate. Removal of the solvent affords the desired product, Compound 75 of Scheme 9.

EXAMPLE 19

3-{N-[(4′,7′-diaza-2′,9′-dimercapto-2′,9′-dimethyldec-5′-yl)methyl]carbamoyl}-1-methylpyridinium iodide (Compound 76 of Scheme 9)

Compound 75 is reacted with methyl iodide according to the general procedure described in Example 2b above. Prepared in this manner is the desired quaternary salt, i.e. Compound 76 of Scheme 8.

EXAMPLE 20

Complex formation

The general procedure of Example 5 can be repeated to convert the other quaternary salts of formula (I) to the corresponding radiopharmaceuticals, e.g. to convert Compound 76 to Complex 78, Compound 83 to Complex 85 and so forth.

EXAMPLE 21

5-aminomethyl-4,7-diaza-2,9-dimethyldecane-2,9-dithiol (Compound 74 of Scheme 9)

To a slurry of 11 g of lithium aluminum hydride in 300 mL of dry tetrahydrofuran is added dropwise, over a 2 hour period and under an argon atmosphere, 13 g of the amide 72 in 150 mL of dry tetrahydrofuran. After the addition is complete, the reaction mixture is heated at reflux for 30 hours, then quenched with saturated Na-K tartrate solution. Treatment with 3N hydrochloric acid and then with saturated sodium carbonate solution, followed by filtration and extraction of the filtrate with dichloromethane, affords an organic solution which is dried over magnesium sulfate. Removal of the solvent affords the desired amine, Compound 74 of Scheme 9, as a viscous oil.

A sample of the free amine thus obtained is dissolved in diethyl ether and hydrogen chloride gas is added. The white powder which separates is removed by filtration and purified from ethanol/water to give the corresponding hydrochloride salt melting at 225°–228° C. $^1$H NMR (D$_2$O) $\delta$3.3–4.2(m,9H,HCl,NHC$\underline{H}_2$, —HCl NHC$\underline{H}_2$), 1.5[m,12H,C(C$\underline{H}_3$)$_2$]. Anal. Calcd. for C$_{11}$H$_{30}$Cl$_3$N$_3$S$_2$. H$_2$O: C,33.63; H,8.21; N,10.69; Cl,27.07; S,16.32. Found: C,33.93; H,7.94; N,10.60; Cl,27.05; S,16.25.

EXAMPLE 22

Comound 192 of Scheme 24

A mixture of 1 g of the amine 74, 75 mL of acetone and a catalytic amount of p-toluenesulfonic acid is heated at reflux for 24 hours. The solvent is removed by rotary evaporation and the residue is taken up in chloroform and treated successively with saturated aqueous sodium bicarbonate solution, aqueous sodium hydroxide solution (10%) and saturated aqueous sodium chloride solution. The solution is dried over magnesium sulfate. Removal of the solvent leaves a viscous mass. Thin layer chromatography (CHCl$_3$/methanol, 2:1) indicates two major components having R$_f$ values of 0.13 and 0.73. The component with the lower R$_f$ value shows a positive ninhydrin test, confirming that it is the desired primary amine 192, while the component with the higher R$_f$ value is negative. $^1$H NMR of the R$_f$0.73 component (CDCl$_3$): $\delta$2.9, 2.5, 1.3–1.5. $^1$H NMR of the R$_f$0.13 component (CDCl$_3$): $\delta$3.0, 2.8, 2.3, 1.2–1.7. Obtained in this manner is the desired bisthiazolidine primary amine, Compound 192 of Scheme 24.

EXAMPLE 23

Compounds 193 and 76 of Scheme 24

Reaction of the bisthiazolidine primary amine 192 with the quaternized activated ester 17 or 191 affords the corresponding bisthiazolidine quaternary, i.e. Compound 193 of Scheme 24, which can then be deprotected, e.g. by reaction with mercuric chloride, followed by treatment with hydrogen sulfide, to give the unprotected quaternary, Compound 76 of Scheme 24.

EXAMPLE 24

Compound 81 of Scheme 10

A solution of 7 g (3 mmol) of the ester 71 in 50 mL of dry tetrahydrofuran is added dropwise over a period of 1 hour to 1.8 g (47 mmol) of lithium aluminum hydride in 200 mL of dry tetrahydrofuran. The mixture is heated at reflux for 16 hours, after which time the reaction is quenched with K-Na tartrate solution. The organic phase is dried over sodium sulfate. Removal of the solvent leaves a yellow viscous mass. Yield 4 g (65%) of the desired alcohol, Compound 81 of Scheme 10. $^1$H NMR (CDCl$_3$) $\delta$2.2–2.8, 3.5, 2.3, 1.5.

EXAMPLE 25

Compound 83 of Scheme 10

Following the general procedure of Example 22, but substituting an equivalent quantity of the alcohol 81 in place of the amine 74, affords the bisthiazolidine alcohol, i.e. the protected counterpart of Compound 81 of Scheme 10. That protected alcohol can then be subjected to the procedures detailed in Example 23 above to ultimately give the corresponding unprotected quaternary, Compound 83 of Scheme 10.

EXAMPLE 26

Compound 32 of Scheme 5

A solution of 17 mL of 2N lithium borohydride in tetrahydrofuran is added to 300 mL of dry tetrahydrofuran under an argon atmosphere. To that solution are added 10 g (0.035 mol) of the ester 40 in 100 mL of dry tetrahydrofuran. The resultant cloudy solution is heated at reflux for 1.5 hours. The reaction is quenched with water and the organic phase is washed with saturated aqueous sodium chloride solution and dried over magnesium sulfate. Removal of the solvent leaves, as a white powder which is very soluble in water, the corresponding primary alcohol, Compound 32 of Scheme 5. Yield 2 g (24%); melting point 85°–90° C.; $^1$H NMR (acetone-$d_6$) $\delta$7–8, 4.15, 3.3–4.0.

EXAMPLE 27

Compound 33 of Scheme 5

To 1 g of the alcohol 32 in 40 mL of dry ethanol is added a solution of sodium thiobenzoate prepared from 0.2 g of sodium in 10 mL of ethanol and 1.26 g of thiobenzoic acid in 5 mL of ethanol. The reaction mixture is stirred at room temperature for 10 minutes, then is heated at 45° C. for an additional 10 minutes. The mixture becomes very thick and difficult to stir and a yellow product separates. The product, Compound 33 of Scheme 5, is removed by filtration and washed with water. Yield 1.2 g, melting point 151°–152° C.; $^1$H NMR (DMSO-$d_6$/acetone-$d_6$) $\delta$7.4–8.3, 3.85, 3.1–3.6.

EXAMPLE 28

Compound 168 of Scheme 18

Cyanoacetic acid (8.5 g; 0.1 mol) and N-hydroxysuccinimide (11.5 g; 0.1 mol) are combined in 150 mL of dry tetrahydrofuran. To the cooled suspension is added dropwise a solution of 20.6 g (0.1 mol) of dicyclohexylcarbodiimide in 50 mL of dry tetrahydrofuran over a period of 2 hours. The mixture is allowed to warm to room temperature overnight. The white precipitate which forms is removed by filtration and washed with 50 mL of tetrahydrofuran. The combined filtrates are concentrated to give 8 g (44% yield) of the ester 167. The product crystallizes from isopropyl alcohol as white needles, m.p. 140°–142° C.

A solution of the ester 167 (0.62 g, 3.4 mmol) in 10 mL of dry dimethoxyethane is added dropwise to a stirred solution of the cyclic diamine 88 (0.8 g, 3.4 mmol) in 20 mL of dry dimethoxyethane at room temperature. The solution is stirred for an additional 2 hours, after which it is allowed to stand for 16 hours. The dimethoxyethane is removed by rotary evaporation and the brown residue is suspended in water to remove N-hydroxysuccinimide. The product 168 is removed by filtration and crystallized from toluene/hexanes as fine brown needles; yield 0.9 g (88%); m.p. 142°–143° C.; IR (thin film) 3450, 2250, 1675 cm$^{-1}$; $^1$HNMR (CDCl$_3$): $\delta$3.7, 2.4–3.6, 3.5, 1.3, 1.25. Anal. Calcd. for C$_{13}$H$_{23}$N$_3$OS$_2$: C, 51.79; H, 7.69; N, 13.94; S, 21.27. Found: C, 51.99; H, 7.12; N, 14.01; S, 21.34.

EXAMPLE 29

Compound 169 of Scheme 18

A solution of 3 g of the nitrile 168 in 50 mL of dry tetrahydrofuran is added dropwise over a 30 minute period to a stirred slurry of 1.2 g of lithium aluminum hydride in 100 mL of dry tetrahydrofuran, under a nitrogen atmosphere. The pale yellow solution is heated at reflux for 7 hours, then stirred at room temperature for 50 hours. The slurry is hydrolysed with a saturated Na-K tartrate solution, the aqueous phase is extracted with dichloromethane and the combined organic extracts are dried over sodium sulfate. Rotary evaporation of the solution leaves the amine 169 as a viscous yellow oil.

EXAMPLE 30

Compound 170 of Scheme 18

A solution of the activated ester 16 (2 g, 9 mmol) in 30 mL of dimethoxyethane is added dropwise over a period of 1 hour to the amine 169 (2.6 g, 8.9 mmol) in 70 mL of dimethoxyethane. After 1 hour, thin layer chromotography (eluent: petroleum ether/acetone/dichloromethane/isopropyl alcohol, 10:5:5:1) indicates one major component having an R$_f$ of 0.6. The solvent is removed by evaporation, the residue is treated with water and the mixture is extracted with chloroform and dried over sodium sulfate. Removal of the solvent leaves 170 as a viscous yellow mass, yield 2.1 g; $^1$HNMR (CDCl$_3$) $\delta$7.3–9.3, 2.6–3.6, 1.5.

EXAMPLE 31

Compound 40 of Scheme 19

To a mixture of 10 g of sodium bicarbonate in 50 mL of water and 200 mL of toluene is added the ester 70 (2 g, 0.01 mol), with cooling in an ice-bath. Chloroacetyl chloride (5 g, 0.44 mol) solution is added dropwise, then the mixture is allowed to warm to room temperature. The organic phase is extracted with ethyl acetate, washed with water and brine and then dried over magnesium sulfate. Removal of the solvent leaves 40 as a white mass; yield 2 g (70%); m.p. 85°–87° C. $^1$HNMR (CDCl$_3$): $\delta$7.12, 7.6, 4.67, 4.2, 4.07, 3.75, 1.3.

EXAMPLE 32

Compound 41 of Scheme 19

A solution of the ester 40 (2 g, 9 mmol) in 20 mL of dry ethanol is prepared under argon. To this is added a solution of sodium thiobenzoate in dry ethanol (prepared from 0.45 g of Na in 20 mL of ethanol to form sodium ethoxide, which is reacted with 2.5 g of 97% thiobenzoic acid). Precipitation occurs immediately. The reaction mixture is heated at reflux for 5 minutes, then is diluted with ethyl acetate. The aqueous phase is extracted with ethyl acetate. The combined organic extracts are washed with water and brine and dried over magnesium solvent. Removal of the solvent leaves 4.1 g of a creamy white powder. Crystallization from toluene gives 2.4 g of white product, 41, m.p. 125°–127° C. (Lit. 129.5°–131° C.). NMR is consistent with structure.

EXAMPLE 33

Compound 176 of Scheme 19

A mixture of iodoethanol (7.5 g, 43 mmol), nicotinamide (5.2 g, 43 mmol) and 150 mL of acetone is heated at reflux for 18 hours. The mixture is cooled and the product 176 is removed by filtration. Yield 1.5 g (12%); m.p. 87° C.

EXAMPLE 34

Compound 177 of Scheme 20

To a mixture of 10 g of potassium carbonate in 20 mL of water and 200 mL of toluene is added 5 g (32 mmol) of 3,4-diaminobenzoic acid. To the cooled mixture is added 14.4 g (127 mmol) of chloroacetyl chloride in 10 mL of toluene over a period of 1 hour. After the addition is complete, the mixture is stirred at room temperature for 30 minutes. The brown product is removed by filtration and crystallized from ethanol. Yield 8 g (82%) of 177, m.p. 240°–241° C.

EXAMPLE 35

Compound 178 of Scheme 20

To 25 mL of ethanol is added 0.17 g of sodium metal, followed by 1.1 g (7.4 mmol) of thiobenzoic acid. To the resultant yellow-brown solution is added 1.16 g (3.7 mmol) of the acid 177. The mixture turns yellow immediately and thickens. The mixture is diluted to 200 mL with dry ethanol and heated at reflux for 2 hours. The product is removed by filtration and crystallized from isopropyl alcohol/tetrahydrofuran.

Yield 1 g (53%) of 178, m.p. 244°–245° C.

EXAMPLE 36

Compound 179 of Scheme 20

To 15.2 g (0.03 mol) of the acid 178 and 3.45 g (0.03 mol) of N-hydroxysuccinimide is added 500 mL of dry tetrahydrofuran. To the resultant suspension is added 6 g (0.03 mol) of dicyclohexylcarbodiimide in 50 mL of dry tetrahydrofuran, over a period of 1 hour. The resulting mixture is stirred at room temperature for 16 hours. The white precipitate of dicyclohexylurea which forms is removed by filtration and the filtrate in concentrated in vacuo to give a brown product. Flash chromatography of a small sample (eluent: dichloromethane/acetone, 3:1) gives the ester 179, m.p. 117°–118° C.

EXAMPLE 37

Compound 183 of Scheme 21

A solution of 2-bromoethylamine hydrobromide (10.2 g, 0.05 mol) and nicotinamide (6 g, 0.05 mol) in 150 mL of dry dimethylformamide is heated at 140° C. for 16 hours. The precipitate which forms is removed by filtration and washed with ether. Yield 14 g (88%), m.p. 280° C. (decomp.) of 183.

EXAMPLE 38

Compound 75 of Scheme 9

A solution of the amine 74 (2 g, 7.5 mmol) and the activated ester 16 (1.65 g, 7.5 mmol) in 100 mL of dry dimethoxyethane is stirred at room temperature for 24 hours. The solvent is removed by rotary evaporation and the residue is treated with water. The viscous product is extracted with chloroform and dried over magnesium sulfate. Removal of the solvent leaves 75 as a viscous mass. NMR is consistent with structure. The compound is used without further purification.

EXAMPLE 39

Compound 76 of Scheme 9

A solution of the amide 75 (0.5 g), 5 mL of methyl iodide and 20 mL of nitromethane is stirred at room temperature for 7 days under argon. After the second day, a precipitate begins to form. The precipitate is removed by filtration and treated with acetone. Yield 150 mg of the quaternary salt 76, m.p. 210°–215° C. (decomp.) $^1$HNMR (DMSO-d$_6$) δ8.3–9.5, 4.5, 3.0–4.0, 1.2–1.5.

EXAMPLE 40

Compound 77 of Scheme 9

To a solution of 0.5 g (1 mmol) of the quaternary salt 76 in 10 mL of water is added 0.25 g (3 mmol) of sodium bicarbonate and 0.61 g (3 mmol) of sodium dithionite. Ether (50 mL) is added and the mixture is stirred under a nitrogen atmosphere for 30 minutes while being cooled in an ice-water bath. The aqueous phase is extracted with dichloromethane. The combined organic phase is dried over magnesium sulfate. Obtained in this manner is the dihydro derivative 77.

EXAMPLE 41

Compounds 81 and 81a of Scheme 10

A solution of the ester 71 (10 g, 35 mmol) in 100 mL of dry tetrahydrofuran is added dropwise over a priod of 30 minutes to a slurry of lithium aluminum hydride (4 g, 94 mmol) in 300 mL of dry tetrahydrofuran, with cooling in an ice-bath. The slurry is then heated at reflux for 24 hours. The reaction is quenched with saturated Na-K tartrate solution, then with 3N hydrochloric acid and finally with sodium carbonate. The aqueous phase is extracted with chloroform. The combined organic phase is washed with saturated aqueous sodium chloride solution and dried over magnesium sulfate. Removal of the solvent leaves the alcohol 81 as a viscous mass. The product is taken up in ether saturated with hydrogen chloride, with cooling in an ice-bath. Yield 6 g of the salt 81a, m.p. 190°–191° C. NMR and elemental analysis consistent with structure.

EXAMPLE 42

Compound 190 of Scheme 23

To 24.6 g (0.17 mol) of nicotinic acid and 32 g (0.19 mol) of N-hydroxyphthalimide in 300 mL of tetrahydrofuran are added 41 g of dicyclohexylcarbodiimide in 200 mL of tetrahydrofuran voer a period of 2 hours. The reaction mixture is stirred at room temperature for 24 hours. The white precipitate of dicyclohexylurea which forms is removed by filtration. The filtrate is concentrated, leaving a white mass which is crystallized twice from ethyl acetate, once from isopropylalcohol, and again from ethyl acetate. The various batches of 190 thus obtained melt at 132°–135° C. and 148°–150° C. $^1$HNMR (CDCl$_3$) δ8.4–9.5 (m, 3H, Py-H); 7.95 (s, 4H, Ar-H); 7.5–7.7 (m, 1H, Py-H).

EXAMPLE 43

Compound 191 of Scheme 23

A solution of the ester 190 (5 g, 18.6 mmol) and methyl iodide (6 g, 42.4 mmol) in 40 mL of acetone is placed in a pressure bottle and heated in an oil bath (bath temperature 65° C.) for 12 hours. The product is removed by filtration. Yield 4.5 g (59%) of the quaternized activated ester 191. The product darkens at 175° C. and melts at 185° C. ¹HNMR (DMSO-d₆) δ8.2-9.9 (m, 4H, Py—H); 8.1 (s, 4H, Ar—H); 4.52 (s, 3H, N—CH₃).

EXAMPLE 44

Compound 180 of Scheme 21

To the activated ester 179 (9 g. 14.9 mmol) in 100 mL of dimethoxyethane is added ethanolamine (0.918 g, 15.4 mmol) in 50 mL of dimethoxyethane. The reaction mixture is stirred at room temperature for 48 hours; the white precipitate which forms is then removed by filtration. Concentration of the solvent gives an additional 2 g of the product. Yield 4 g (49%) of 180, melting at 205°-210° C. ¹HNMR (DMSO-d₆): δ7.5-10, 4.8, 3.3-3.7, 3.3.

EXAMPLE 45

Compound 179 of Scheme 25

The acid 178 (8 g) and N-hydroxysuccinimide (1.8 g) are combined in 200 mL of tetrahydrofuran. To that suspension is added dicyclohexylcarbodiimide (3.16 g) in 25 mL of tetrahydrofuran over a period of 2 hours. The mixture is then stirred at room temperature for 16 hours. The white precipitate is removed by filtration and the filtrate is concentrated in vacuo. The product, the activated ester 179, is crystallized from toluene.

EXAMPLE 46

Compound 194 of Scheme 25

To 4.7 g (8 mmol) of the activated ester 179 is added a solution of 0.14 g (8 mmol) of ammonia in 150 mL of dimethoxymethane. The reaction mixture is stirred at room temperature for 16 hours. The solution is concentrated in vacuo to give 3 g of the amide 194 as a white product.

EXAMPLE 47

Compound 76 of Scheme 23

To 6.12 g (23 mmol) of the amine 74 in 100 mL of anhydrous dimethylformamide is added dropwise, over a period of 4 hours, 2.2 g (6 mmol) of the activated ester 17 in 80 mL of anhydrous dimethylformamide. The reaction is carried out at −47° C. (acetonitrile/dry ice) while under an argon atmosphere. The reaction mixture is stirred for an additional 2 hours at −47° C., then is placed in a freezer (approximately −20° C.) overnight. The dimethylformamide is removed in vacuo. To the residue is added 150 mL of xylene and the solvent is again removed in vacuo. The residue is taken up in 75 mL of benzene and triturated with petroleum ether, after which a gummy product separates. This process is repeated twice. The resultant gummy residue is suspended in the same solvent. HPLC data indicate one major peak with some amine being present. Flash chromatography (eluent, methanol) of a small sample of the reaction mixture gives a product which by HPLC indicates two components, the residual amine and the desired quaternary salt 76.

EXAMPLE 48

Compound 76 of Scheme 23

To 1.5 g (5.7 mmol) of the amine 74 in 20 mL of dimethylformamide is added 0.5 g (1.4 mmol) of the quaternary compound 191 in 20 mL of dimethylformamide. The reaction is carried out at −47° C. over a two hour period, under an argon atmosphere. The solvent is removed in vacuo and the residue is treated 5 times with benzene/petroleum ether. HPLC data again indicates most of the amine has been removed, leaving the desired quaternary salt 76.

EXAMPLE 49

1-methyl-3-[N-{{β-{4-[1',2'-bis(4"-methylthiosemicarbazono)prop-1'-yl]-phenyl}ethyl}}carbamoyl]-pyridinium iodide hemihydrate

(Compound 222 of Scheme 32)

Amino-PTS hydrochloride monohydrate (100 mg, 0.238 mmol) in dry pyridine (15 mL) with the quaternized activated ester 191 (200 mg, 0.488 mmol) is heated at gentle reflux. After 2 hours, no amino-PTS remains and the mixture is set aside to cool. Volatiles are removed in vacuo and the residue is washed with water (10 mL) and taken into chloroform (40 mL). The aqueous layer is re-extracted with chloroform (20 mL) and the combined, dried (MgSO₄) organic layers are evaporated to dryness, leaving an orange oil. The oil is taken into a minimum of warm ethanol. Trituration results in precipitation of a pale yellow powder. Yield 75 mg (51%) of the quaternary salt 222, melting at 214°-216° C. IR (KBr) 3000-3600, 1670, 1535, 1470 cm⁻¹; ¹HNMR (DMSO-d₆) δ9.5, 8.1-9.4, 7.1-7.6, 4.5, 2.3-3.8. Analysis calculated for $C_{22}H_{29}N_8IOS \cdot \frac{1}{2}H_2O$: C, 42.51; H, 4.86; N, 18.01; S, 10.31. Found: C, 42.70; H, 4.77; N, 17.74; S, 10.42.

EXAMPLE 50

1-{{4'-{β-[N-(1"-methyl-1",4"-dihydropyridin-3"-yl)carbonylamino]ethyl}phenyl}}propane-1,2-dione bis(4-methylthiosemicarbazone), hydrated with ¼ mole H₂O

(Compound 223 of Scheme 32)

The quaternary salt 222 (104 mg, 0.17 mmol) in ice-cold deaerated water (30 mL) is treated with sodium bicarbonate (140 mg, 1.7 mmol) and sodium dithionite (30 mg, 1.7 mmol). Ethyl acetate (50 mL) is added to the stirred solution, and nitrogen gas (scrubbed free of oxygen by passing through a basic pyrogallol solution) is bubbled through the reaction mixture. After 45 minutes, the organic and aqueous layers are separated, and the aqueous layer is re-extracted with ethyl acetate (30 mL). The combined organic layers are dried over magnesium sulfate and the volume of solvent is reduced to half by evaporation in vacuo. The product is eluted through a short column of neutral alumina (Aldrich, 150 mesh, Brockman 1). Evaporation of the solvent affords the dihydro derivative 223 as a yellow powder. Yield 57 mg (70%). The product darkens at 130° C. and decomposes at 185° C. ¹HNMR (CDCl₃/DMSO-d₆) δ8.0-8.3, 7.1-7.5, 6.95, 6.0-6.4, 5.6-5.8, 4.5-4.8, 3.4-3.7, 3.2, 2.8-3.4, 2.3. Analysis calculated for $C_{22}H_{30}N_8OS_2 \cdot \frac{1}{4}H_2O$: C, 53.80; H, 6.41; N, 22.82; S, 13.04. Found: C, 53.80; H, 6.27; N, 22.63; S, 13.02.

The foregoing reaction schemes and examples illustrate the preparation of a wide variety of derivatives of this invention in which the dihydropyridine⇌pyridinium salt redox carrier moieties can be one of the [DHC]/[QC⁺] groupings depicted on pages 19 to 38 hereinabove wherein p is zero. The preparation of yet other derivatives of this type will be readily apparent to those skilled in the art from the teachings hereinabove, particularly in light of the illustrative synthetic methods detailed in the PCT application referred to hereinabove, i.e. PCT/US83/00725. Moreover, it is possible to adapt the methods of PCT/US83/00725 and of the present specification to the preparation of the instant derivatives containing the carrier moieties depicted on pages 19 to 38 above wherein p=1 or 2.

Some illustrative methods for preparing the compounds of this invention in which the carrier comprises a

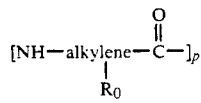

group as depicted hereinabove wherein p=1 or 2 are set forth below. It should be noted that just as the p=1 or 2 derivatives can be made by methods analogous to those depicted in the reaction schemes for the p=0 derivatives, so, too, the p=0 derivatives can be prepared by methods analogous to those specifically described below for the p=1 or 2 derivaties. The methods described below must of course be adapted to the particular chelating agent selected for derivation, in analogous fashion to the reaction schemes depicted above.

ILLUSTRATIVE SYNTHETIC METHODS

I. Methods for Derivatizing —NH$_2$ or —NH— Functions

METHOD A

The chelating agent or its protected counterpart (e.g. 74 in Scheme 9 or 192 in Scheme 24 or 221 in Scheme 32) is reacted with nicotinuric acid chloride, with nicotinuric acid anhydride, or with nicotinuric acid in the presence of a suitable coupling agent such as dicyclohexylcarbodiimide, in an appropriate organic solvent, to afford the corresponding glycylnicotinamide, or nicotinuramide. The nicotinuramide is then quaternized, typically by treatment with methyl iodide in a suitable organic solvent, to afford the quaternary derivative, which is then de-protected if necessary and reduced by treatment with sodium dithionite or sodium borohydride as generally described hereinabove.

Alternatively, glycine may be first reacted with a reagent capable of introducing an amino protecting group such as benzyloxycarbonyl or t-butoxycarbonyl and the N-protected glycine then reacted with the chelating agent or its protected counterpart in the presence of a coupling agent such as dicyclohexylcarbodiimide, followed by removal of the N-protecting group, followed by reaction with nicotinoyl chloride or nicotinic anhydride, or with nicotinic acid in the presence of dicyclohexylcarbodiimide or other suitable coupling agent, to afford the nicotinuramide. The nicotinuramide may then be quaternized and the quaternary deprotected if necessary and reduced as described in the preceding paragraph.

The procedure of the second paragraph of this method may be repeated using picolinic acid or its acid chloride or anhydride, or isonicotinic acid or its acid chloride or anhydride, in place of nicotinic acid or its acid chloride or anhydride, respectively, to convert chelating agents or their protected counterparts to the corresponding glycyl picolinamides and glycyl isonicotinamides and then to the corresponding quaternary and dihydro derivatives. The procedure of the first paragraph of this method may be similarly adapted. Moreover, any of these procedures may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

Alternatively, the chelating agent or its protected counterpart may be reacted with an activated ester of nicotinuric acid or the like, e.g. a sucinimidyl ester such as

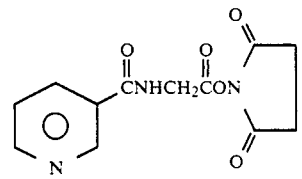

and the product quaternized, de-protected if necessary and then reduced as described in the first paragraph of this method to afford the identical products. As yet another and highly desirable alternative, the activated ester, e.g. the siccinimidyl ester depicted above, may be quaternized (e.g. by treatment with methyl iodide) and the quaternized activated ester then reacted with the drug. The quaternary compound thus obtained may then be de-protected if necessary and reduced as described in the first paragraph of this method.

METHOD B

This method is of particular use when the —NH— function is part of an amide or imide or a very low pKa primary or secondary amine.

The chelating agent (e.g. 52 in Scheme 7) is first reacted with an aldehyde [e.g. formaldehyde, benzaldehyde, acetaldehyde or chloral (Cl$_3$CCHO)]; for example, in the case of formaldehyde, one converts the —NH— function to a

function and thus forms a suitable bridging group. The resultant compound is then reacted with nicotinuric acid in the presence of a suitable dehydrating agent, or with nicotinuric acid chloride or nicotinuric acid anhydride, to form the corresponding nicotinuric acid ester of the partial formula

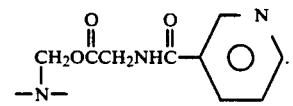

The resultant intermediate is then quaternized and reduced as in Method A. The alternative process utilizing an activated ester or quaternary derivative thereof which is described in Method A may be utilized to advantage here as well.

Alternatively, the steps subsequent to formation of the

function may be replaced with steps analogous to those detailed in the second paragraph of Method A.

The procedure of the preceding paragraph may be repeated using picolinic acid or its acid chloride or anhydride, or isonicotinic acid or its acid chloride or anhydride, in place of nitotinic acid or its acid chloride or anhydride, respectively (as called for in the second paragraph of Method A), to convert chelating agents to the corresponding glycyl picolinic acid esters and glycyl isonicotinic acid esters and then to the corresponding compounds of this invention. Derivatives of amino acids other than glycine may be similarly prepared. See Method A, last paragraph.

As yet another alternative, the intermediate compound containing the

group or the like may be reacted with thionyl chloride to afford the corresponding compound containing a

or similar group. That derivative may then be reacted with a metallic salt (especially a silver or thallous salt) of nicotinuric acid or the like (formed, e.g. by reacting nicotinuric acid or the like with fresh silver hydroxide or oxide or with thallous ethoxide). The resultant nicotinuric acid ester of the partial formula

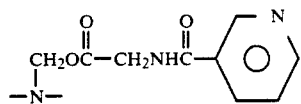

or like derivative is then quaternized and subsequently reduced as in Method A.

METHOD C

The procedure of the second paragraph of Method A is followed, except that removal of the N-protecting group is followed by reaction with 3-quinolinecarboxylic acid or its acid chloride or anhydride instead of nicotinic acid or its acid chloride or anhydride.

The procedure of the first paragraph of Method A may be similarly adapted to the production of the 3-quinolinecarboxylic acid derivatives. Moreover, Method C may be combined with Method to afford the corresponding 3-quinolinecarboxylic acid derivatives of the type of chelating agent used in that method.

The procedure of the first paragraph of this method may be repeated using 4-isoquinolinecarboxylic acid or its acid chloride or anhydride to convert chelating agents such as those mentioned with Methods A and B to the corresponding 4-isoquinolinecarboxylic acid derivatives.

The procedure of the first or third paragraph of this method may be repeated, substituting a different amino acid, e.g. alanine, valine, leucine, phenylalanine, isoleucine, methionine, asparagine or glutamine, for the glycine used in the first step. (See Method A, second paragraph).

The general procedures described above may be utilized to provide the 1,2-dihydro derivatives as well as the 1,4-dihydros.

METHOD D

The procedure of the second paragraph of Method A is followed, except that a reactant of the formula

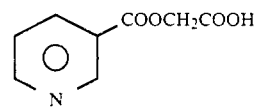

is used place of nicotinic acid. (That starting material may be prepared by reacting nicotinic anhydride, nicotinoyl chloride or nicotinic acid with glycolic acid.)

The foregoing procedure can be repeated using picolinic acid or its acid chloride or anhydride, or isonicotinic acid or its acid chloride or anhydride, in place of nicotinic acid or its acid chloride or anhydride, respectively, in the preparation of the reactant depicted above. This variation affords a reactant of the formula

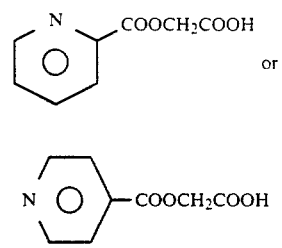

which can then be used in place of nicotinic acid to prepare derivatives of chelating agents or their protected counterparts such as those mentioned with Method A.

METHOD E

The procedure of the second paragraph of Method A is followed, except that a reactant of the formula

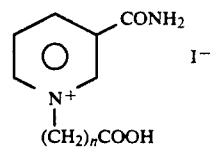

wherein n=1–3, preferably 2, is used in place of nicotinic acid. (That reactant may be prepared from nicotinamide, e.g. when n=2, by reacting 3-iodopropionic acid with nicotinamide.) The quaternary salt thus obtained may then be de-protected if necessary and reduced as described in Method A. See also Scheme 26.

The procedure described above can be repeated using picolinamide or isonicotinamide in place of nicotinamide in the preparation of the reactant depicted above. This variation affords a reactant of the formula

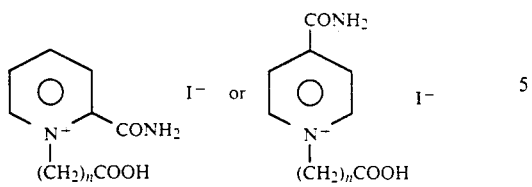

which can then be used in place of nicotinic acid in the procedure of the first paragraph of this method.

II. Methods for Derivatizing —OH Functions

METHOD F

The chelating agent or its protected counterpart (e.g. 81 of Scheme 10, or the corresponding bisthiazolidine) is reacted with nicotinuric acid chloride, with nicotinuric acid anhydride, or with nicotinuric acid in the presence of a suitable coupling agent such as dicyclohexylcarbodiimide, in an appropriate organic solvent, to afford the corresponding glycylnicotinate, or nicotinurate. The nicotinurate is then quaternized, de-protected if necessary and subsequently reduced as described above in Method A. The alternative process utilizing an activated ester or quaternary derivative thereof which is described in Method A may be utilized to advantage here as well.

Alternatively, glycine may be first reacted with a reagent capable of introducing an amino protecting group such as benzyloxycarbonyl or t-butylcarbonyl and the N- protected glycine then reacted with the chelating agent or its protected counterpart in the presence of a coupling agent such as dicyclohexylcarbodiimide, followed by removal of the N- protecting group, followed by reaction with nicotinoyl chloride or nicotinic anhydride, or with nicotinic acid in the presence of dicyclohexylcarbodiimide or other suitable coupling agent, to afford the nicotinurate. The nicotinurate may then be quaternized, de-protected if necessary and the quaternary reduced as described in the preceding paragraph.

The procedure of the second paragraph of this method may be repeated using picolinic acid or its acid chloride or anhydride, or isonicotinic acid or its acid chloride or anhydride, in place of nicotinic acid or its acid chloride or anhydride, respectively, to convert chelating agents to the corresponding glycyl picolinic acid esters or glycyl isonicotinic acid esters and then to the corresponding compounds of the invention. The procedure of the first paragraph of this method may be similarly adapted. Moreover, any of these procedures may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

METHOD G

The procedure of the second paragraph of Method F is followed, except that a reactant of the formula

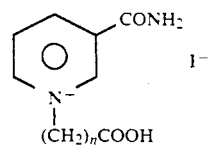

wherein $n=1-3$, preferably 2 (prepared as described in Method E), is used in place of nicotinic acid. The quaternary salt thus obtained may then be de-protected if necessary and reduced as described in Method A.

Method G is of particular use in preparing derivatives of chelating agents in which the hydroxy function is hindered.

Alternatively, Method G may follow Method F, second paragraph, except that it employs a reactant of the formula

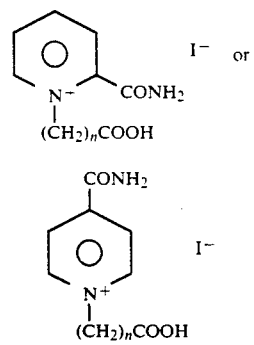

(prepared as described in Method E) in place of nicotinic acid.

The procedures of this method may be repeated, substituting a different amino acid, e.g. alanine, valine, leucine, phenylalanine, isoleucine, methionine, asparagine or glutamine, for the glycine used in the first step. (See Method A, second paragraph).

METHOD H

The procedure of Method F, second paragraph, is followed, except that removal of the N- protecting group is followed by reaction with 3-quinolinecarboxylic acid or its acid chloride or anhydride instead of nicotinic acid or its acid chloride or anhydride.

The procedure of the first paragraph of Method F may be similarly adapted to the production of the 3-quinolinecarboxylic acid derivatives.

The procedure of Method H may be repeated using 4-isoquinolinecarboxylic acid or its acid chloride or anhydride in place of 3-quinolinecarboxylic acid or its acid chloride or anhydride.

3-Quinolinecarboxylic acid or its acid chloride or anhydride or 4-isoquinolinecarboxylic acid or its acid chloride or anhydride can also be substituted for nicotinic acid or its acid chloride in Method B, fourth paragraph, to afford the corresponding derivatives.

The general procedures described above may be utilized to provide the 1,2-dihydro derivatives as well as the 1,4-dihydros.

METHOD I

The procedure of the second paragraph of Method F is followed, except that a reactant of the formula

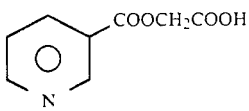

is used in place of nicotinic acid.

A starting material of the formula set forth immediately above can also be substituted for nicotinic acid in Method B, paragraph 4, to afford the corresponding derivatives.

Alternatively, Method I may follow Method F, second paragraph, except that it employs a reactant of the formula

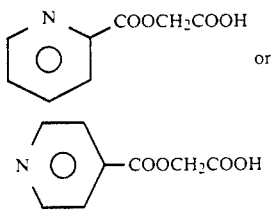

(prepared as described in Method D). These alternative Method I starting materials may be substituted for nicotinic acid in Method B, fourth paragraph, to give the corresponding derivatives.

The procedure of the first or third paragraph of this method may be repeated, substituting a different amino acid, e.g. alanine, valine, leucine, phenylalanine, isoleucine, methionine, asparagine or glutamine, for the glycine used in the first step. (See Method A, second paragraph).

III. Methods for Derivatizing —COOH Functions

METHOD J

Nicotinuric acid (N-nicotinoylglycine) or an activated ester thereof is reacted with an aminoalkanol

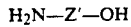

wherein Z' is $C_1$-$C_8$ straight or branched alkylene, e.g. 2-aminoethanol, to afford the corresponding intermediate alcohol, e.g. in the case of 2-aminoethanol, an intermediate of the formula

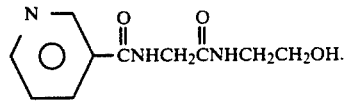

That alcohol is then reacted with a chelating agent containing one or more —COOH functions, in the presence of a suitable coupling agent such as dicyclohexylcarbodiimide. The compound thus obtained is then quaternized and subsequently reduced as described above in Method A.

Nicotinuric acid is commercially available. However, it and analogous starting materials can be readily prepared by reacting the selected amino acid with the acid chloride of nicotinic acid, of picolinic acid, of isonicotinic acid, of 3-quinolinecarboxylic acid, of 4-isoquinolinecarboxylic acid or the like to afford the desired N-substituted amino acid, which can then be reacted with an aminoalkanol as described above.

METHOD K

The chelating agent is first reacted with ethylene glycol (or other dihydroxyalkanol having up to 8 carbon atoms), in the presence of a suitable coupling agent such as dicyclohexylcarbodiimide, to convert the —COOH function(s) to the corresponding

—COOCH$_2$CH$_2$OH (or other

group(s). Then, a N-protected amino acid, such as N-benzyloxycarbonylglycine, which has been prepared as described in Method A, is reacted therewith in the presence of dicyclohexylcarbodiimide or other appropriate coupling agent. Removal of the protecting group, e.g. by catalytic hydrogenation, affords a derivative of the chelating agent in which the original —COOH group(s) has/have, in the case of utilizing ethylene glycol and glycine, been converted to the structure

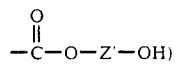

That intermediate is then reacted with a compound of the formula

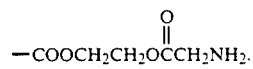

or the like, prepared as described in Method E, in the presence of a coupling agent such as dicyclohexylcarbodiimide, to give the desired quaternary derivative. Subsequent reduction to the corresponding dihydro derivative proceeds as described in Method A.

The procedure described above may be repeated utilizing a reactant of the formula

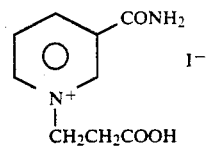

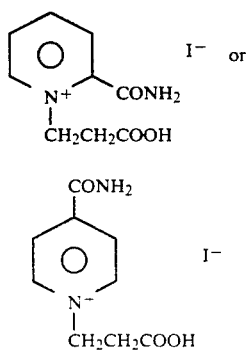

or the like, prepared as described in Method E, in place of the intermediate of the formula

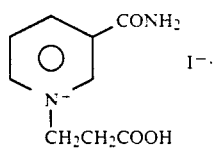

METHOD L

A chelating agent containing one —COOH function is reacted with an equivalent amount of inositol, in the presence of dicyclohexylcarbodiimide or other suitable coupling agent, to convert the —COOH function to a group of the structure

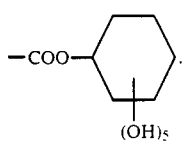

Reaction of that intermediate with nicotinuric acid, in the presence of a suitable coupling agent, or with an activated ester of nicotinuric acid, affords an intermediate in which the original —COOH has been converted to

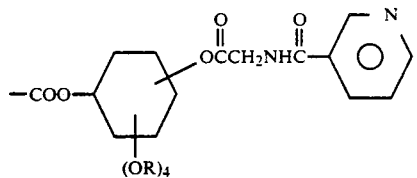

wherein each R is H or

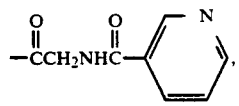

the number of original hydroxy groups esterified varying with the amount of nicotinuric acid employed. Subsequent quaternization and reduction are carried out as in Method A.

Alternatively, the above procedure may be repeated, replacing nicotinuric acid with an analogous starting material, prepared by reacting the selected amino acid with the acid chloride of nicotinic acid, of picolinic acid, or isonicotinic acid, of 3-quinolinecarboxylic acid, of 4-isoquinolinecarboxylic acid or the like.

Repetition of the procedure of the first paragraph of this method utilizing a greater amount of the chelating agent (e.g. 2 to 5 or more moles per mole of inositol) provides an intermediate containing from 2 to 5 acid residues and from 4 to 1 hydroxyl groups. That intermediate is then reacted with nicotinuric acid to convert at least one hydroxyl group to the corresponding

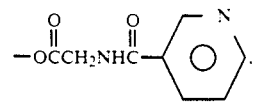

group. Subsequent formation of the quaternary and reduction proceed as in Method A.

METHOD M

The chelating agent is first reacted with 1,2-propylene glycol (or other dihydroxyalkanol having up to 8 carbon atoms), in the presence of a suitable coupling agent such as dicyclohexylcarbodiimide, to convert the —COOH function(s) to the corresponding $$-COOCH_2CHOH$$
$$|$$
$$CH_3$$

(or other

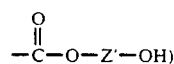

group(s). The resultant intermediate is then reacted with nicotinuric acid, in the presence of an appropriate coupling agent, or with an activated ester of nicotinuric acid, to give an intermediate of the partial formula

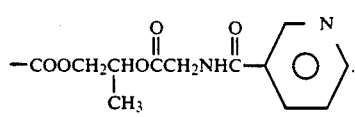

Subsequent quaternization and reduction are carried out as in Method A.

Alternatively, the above procedure may be repeated, replacing nicotinuric acid with an analogous starting material, prepared by reacting the selected amino acid with the acid chloride of nicotinic acid, of picolinic acid, of isonicotinic acid, of 3-quinolinecarboxylic acid, of 4-isoquinolinecarboxlic acid or the like.

METHOD N

Glucosamine, of the structural formula

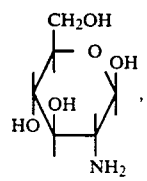

is reacted with nicotinuric acid, using equimolar amounts of the reactants, in the presence of a suitable coupling agent such as dicyclohexylcarbodiimide, or with an activated ester of nicotinuric acid. The resultant intermediate of the formula

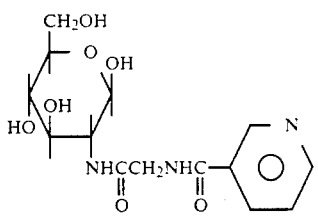

is then reacted with a chelating agent containing one reactive —COOH function, in the presence of dicyclohexylcarbodiimide or other appropriate coupling agent, replacing one or more of the hydroxy groups with acid residue(s), the number of groups replaced varying with the relative amounts of reactants used.

Alternatively, the above procedure may be repeated, replacing nicotinuric acid with an analogous starting material, prepared by reacting the selected amino acid with the acid chloride of nicotinic acid, of picolinic acid, of isonicotinic acid, of 3-quinolinecarboxylic acid, of 4-isoquinolinecarboxylic acid or the like.

Suitable nontoxic pharmaceutically acceptable diluents or vehicles for use with the present complexes of formula (III) will be apparent to those skilled in this art. See, for example, *Remington's Pharmaceutical Sciences*, 4th Edition (1970). Obviously, the choice of suitable diluents or vehicles will depend upon the exact nature of the particular dosage form selected.

The dosage ranges for administration of the complexes according to this invention will vary with the size and species of the subject, the objective for which the complex is administered, the particular dosage form employed, and the like, as discussed below. The quantity of given dosage form needed to deliver the desired dose of the radiopharmaceutical, of course, depends upon the concentration of the complex in any given pharmaceutical composition/dosage form thereof and the radioactivity thereof.

By way of example only, a 5-50 mg/kg dose of formula (III) radiopharmaceutical, injected into the tail vein or carotid vein of rats, due to the "lock in" mechanism will exhibit a very significant difference between brain and peripheral levels of radioactivity, with consequent ready radioimaging of the brain; imaging at approximately 60 to 90 minutes after administration will be most effective, since it will take advantage of this brain/peripheral differential.

The instant radiopharmaceuticals are generally administered intravenously. Sustained release administration, typically by slow intravenous infusion, will further enhance the site-specificity of the instant redox system. The rate of release of the formula (III) radiopharmaceutical from the sustained release system should be comparable to the rate of in vivo oxidation of the dihydro form (III) to the quaternary form (IV) in order to achieve the greatest degree of enhancement of specificity.

In a further aspect, the present invention also provides a process for the manufacture of a diagnostic agent for the visualization of an organ such as the brain. To that end, the blood-brain barrier penetrating form, formula (III), is admixed with an aqueous buffer medium having a pH value of about 4 to about 8 preferably of about 6.5 to about 7.5, in an effective radioimaging amount.

Preparation of the radiopharmaceutical can be carried out in the hospital or like location where the patient is found in order to minimize losses of radioactivity caused by the decay of the radioactive metal. Inasmuch as the preparation for visualization is injectable, it must be sterile and pyrogen-free; preferably, it is also isotonic. To this end, a so-called labeling kit can be provided that permits a simple, rapid and safe labeling of the solution to be injected with the radioactive metal, e.g., technetium-99m. Such kits are especially desirable when a short-lived radioisotope such as technetium 99-m is used.

The kit includes a collecting vial for receiving and/or containing an aqueous medium in which complexing reaction can be effected. Additionally, the kit includes the chelating agent of formula (II) or chelating agent precursor of formula (I) and a pharmacologically acceptable reducing agent for reducing the radioactive element to an appropriate oxidation state for complexing with the chelating agent [and also for reducing the pyridinium carrier moiety to the corresponding dihydropyridine form, when a chelating agent precursor of formula (I) is present].

In the case of technetium-99m, the radioactive element is received from a radionuclide generator as an aqueous pertechnetate ($TcO_4^-$) solution such as an eluate in isotonic saline, as is well-known in the art. The amount of Tc-99m required to produce a quantity of formula (III) radiopharmaceutical sufficient for diagnostic purposes is generally from 0.01 milliCurie (mCi) to about 500 mCi per ml of 99m-pertechnetate solution. The reducing agent for the pertechnetate can be a thiosulfate or dithionite if the reducing reaction is to be carried out in a basic medium, or a tin (II) salt such as $SnCl_2$ if the reducing reaction is to be carried out in an acid medium.

A kit for preparing an injectable radiopharmaceutical, e.g., for complexing an organ-specific agent labeled with a radioactive metal, includes, in separate containers: (1) a biologically compatible, sterile aqueous medium suitable for complex formation with a radioactive metal, (2) a dihydropyridine⇌pyridinium salt carrier-containing complexing agent of formula (I) or (II) compatible therewith, and (3) a pharmaceutically acceptable reducing agent for the radioactive metal.

The dihydropyridine⇌pyridinium salt carrier moiety may be present in the kit either in its oxidized or its reduced state, as desired. The reducing agent for the radioactive metal can be selected to reduce also the oxidized carrier moiety, if present, as the radioactive metal is reduced to form the complex preparatory to injection of the radiopharmaceutical into a test animal or a patient. In a preferred embodiment of this invention, a reducing agent capable of reducing both the oxidized form of the carrier moiety and the radioactive metal is chosen and the chelating agent precursor of formula (I) is present in the kit. In an especially preferred embodiment the kit comprises, in separate containers (preferably aseptically and hermetically sealed vials of approximately 5-25 ml volume), (1) a biologically compatible, sterile aqueous medium, (2) a chelating agent precursor of formula (I), (3) a pharmacologically acceptable reducing agent capable of reducing the chelating agent precursor of formula (I) to a chelating agent of formula (II) and also capable of reducing the radioactive metal to an oxidation state in which it is capable of complexing with the formula (II) chelating agent to form a radiopharmaceutical of formula (III). Most preferably, the reducing agent is sodium dithionite; also most preferably, the radioactive metal is technetium. The dithionite reduction is preferably carried out in basic medium; this may be accomplished by providing that the aqueous medium (1) above is of basic pH, or by adding an appropriate base (e.g. NaOH, $Na_2CO_3$) when combining the kit components and the pertechnetate solution. As yet another alternative, the kit could comprise only two separate components: (1) the biologically compatible, sterile aqueous medium of essentially neutral pH containing the chelating agent precursor of formula (I); and (2) the reducing agent and the base, e.g. sodium dithionite and sodium carbonate.

Radioactive metal ions are typically not provided with the kit due to the relatively short half-lives of commonly utilized radionuclides. Rather, the radionuclide is provided separately as described earlier and admixed with the components of the kit shortly before use, as is known for other radiopharmaceutical delivery systems. In the case of technetium-99m, the pertechnetate solution and the basic aqueous medium may be first combined and then heated, e.g. from 40° to 95° C. for 10 to 20 minutes, in the presence of the reducing agent, then cooled to about room temperature or below prior to addition of the formula (I) precursor. In this instance, the technetium will be reduced prior to reduction of the quaternary moiety to the corresponding dihydro form in which case a substantial portion of the quaternary salt (I) will likely chelate with the reduced technetium to form the quaternary complex (IV) in the reaction mixture as an intermediate to the dihydro complex (III), rather than the quaternary salt (I) being first converted to the dihydro chelating agent (II) and then to the dihydro complex (III). Alternatively, if only minimal or no heating is done, the precursor may be present in the initial mixture made from the kit, and it is likely in this instance that the formula (I) quaternary will be first reduced to the formula (II) dihydro, which will then chelate with the reduced technetium to form the complex (III). If the mixture is mildly basic, e.g. pH 8 to 9, it may be administered as is, after the reduction and chelation have occurred to form the formula (III) radiopharmaceutical, or the pH may be adjusted to about 7. If the mixture is more strongly basic, e.g. pH 13, it is generally desirable to adjust the pH to a slightly alkaline or neutral value.

Whatever the exact configuration of the kit, it is preferable for it to contain excess chelating agent precursor (I) or chelating agent (II) with respect to the radionuclide to be complexed therewith, e.g. a 1:2 molar excess. The reducing agent is present in a large excess with respect to the chelating agent precursor (I), e.g. 1:5 to 1:10. When the chelating agent (II) rather than the precursor (I) is present, then the reducing agent is preferably present in a slight excess with respect to the radionuclide.

To effect visualization, the diagnostic agent is administered to a patient, typically intravenously, with or without further dilution by a carrier vehicle such as physiological saline, phosphate-buffered saline, plasma, or the like. Generally, the unit dose to be administered has a radioactivity of about 0.01 milliCurie (mCi) to about 100 milliCuries, preferably about 1 mCi to about 20 mCi. The solution to be injected into an adult patient per unit dosage is about 0.01 milliliter (ml) to about 1 milliliter.

After intravenous administration, imaging of the organ in vivo can take place after a few minutes. If desired, imaging can also take place hours after the injection, depending upon the half-life of the radioactive material that has been introduced into the patient and upon the amount of such material introduced. Preferably, imaging takes place 60 to 90 minutes after intravenous administration.

Any conventional method of imaging for diagnostic purposes can be utilized when practicing the present invention.

In summary, then, in its broadest aspects the present invention can be seen to provide compositions of matter comprising: (1) the residue of a chelating agent having at least one reactive functional group selected from the group consisting of amino, carboxyl, hydroxyl, amide and imide, said functional group being not essential for the complexing properties of said chelating agent, said residue being characterized by the absence of a hydrogen atom from at least one of said reactive functional groups of said chelating agent, said chelating agent being either (a) capable of chelating with a metallic radionuclide or (b) chelated with a metallic radionuclide; and (2) a dihydropyridine⇌pyridinium salt redox carrier moiety; said chelating agent residue and said carrier moiety being coupled to each other to form a hydrolytically cleavable linkage between.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A salt having the structural formula

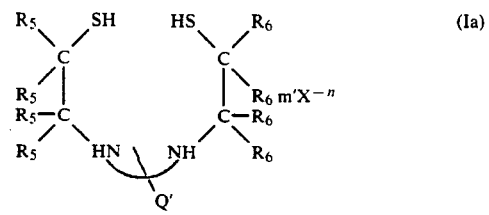

(Ia)

wherein each $R_5$ is independently selected from the group consisting of H and $C_1$-$C_7$ alkyl, or an $R_5$ can be combined with the adjacent

such that

represents

each $R_6$ is independently selected from the group consisting of H and $C_1$-$C_7$ alkyl, or an $R_6$ can be combined with the adjacent

such that

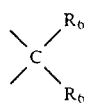

represents

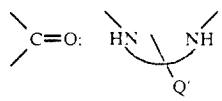

is a radical of the formula

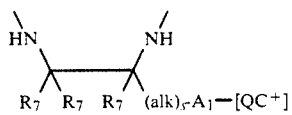

or

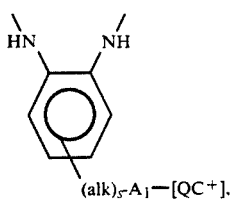

wherein each $R_7$ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —$A_1$—; $X^-$ is the anion of a pharmaceutically acceptable organic of inorganic acid; n is the valence of the acid anion; m' is a number which when multiplied by n is equal to one; s is zero or one; —$A_1$— is —NH—, —O— or

wherein $R_8$ is $C_1$-$C_7$ alkyl; and [$QC^-$] is a radical of the formula

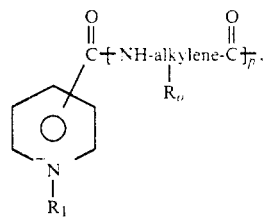 (a)

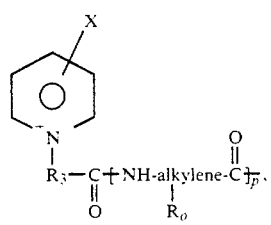 (b)

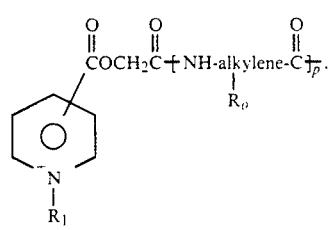 (c)

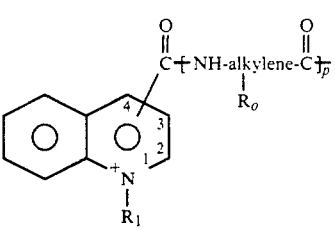 (d)

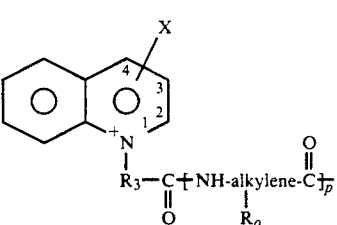 (e)

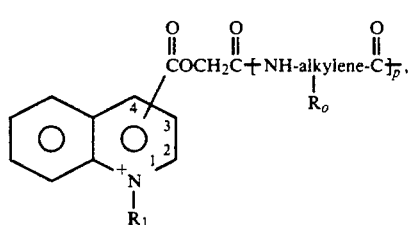 (f)

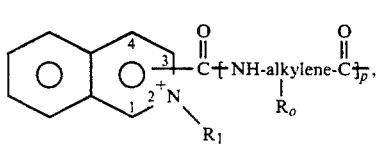 (g)

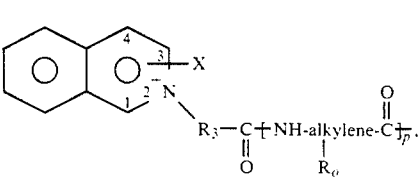 (h)

-continued
or

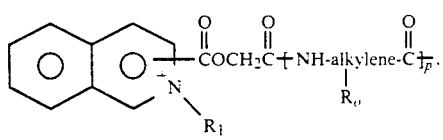

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring.

2. A salt as defined by claim 1, wherein p is zero.

3. A salt as defined by claim 1, wherein p is one, alkylene is —$CH_2$— and $R_o$ is H, —$CH_3$, —$CH(CH_3)_2$, —$CH_2$—$CH(CH_3)_2$,

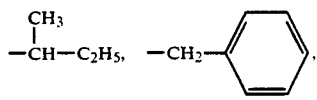

—$(CH_2)_2$—$SCH_3$, —$CH_2$—$CONH_2$ or —$CH_2CH_2$—$CONH_2$.

4. A salt having the structural formula

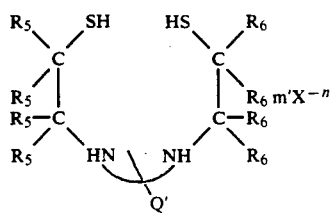 (Ia)

wherein each $R_5$ is independently selected from the group consisting of H and $C_1$-$C_7$ alkyl, or an $R_5$ can be combined with the adjacent

such that

represents

each $R_6$ is independently selected from the group consisting of H and $C_1$-$C_7$ alkyl, or an $R_6$ can be combined with the adjacent

such that

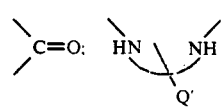

represents

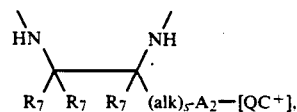

is a radical of the formula

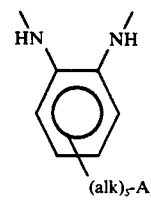

wherein each $R_7$ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —$A_2$—; $X^-$ is the anion of a pharmaceutically acceptable organic of inorganic acid; n is the valence of the acid anion; m' is a number which when multiplied by n is equal to one; s is zero or one; —$A_2$— is —CONH— or

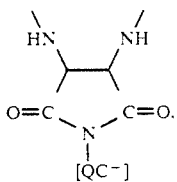

wherein $R_9$ is $C_1$-$C_7$ alkyl; and [QC$^+$] is a radical of the formula

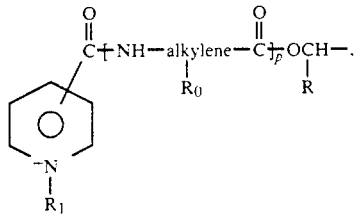
(k)

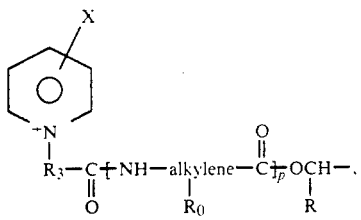
(l)

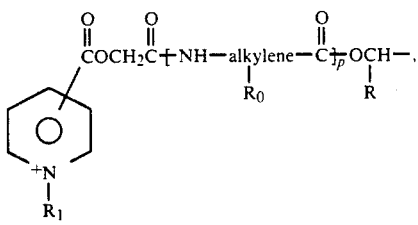
(m)

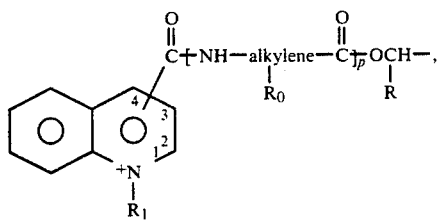
(n)

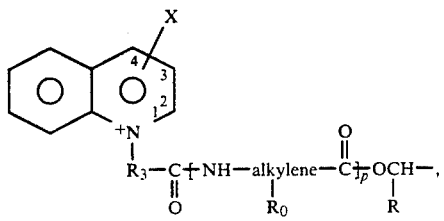
(o)

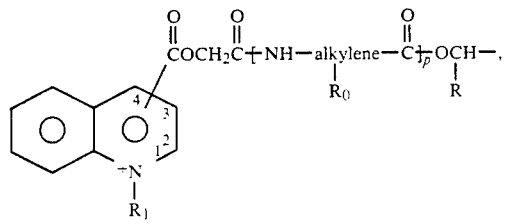
(p)

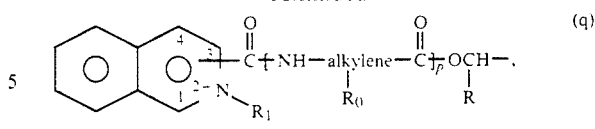
(q)

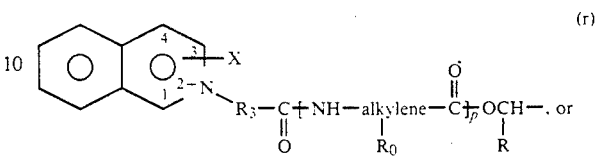
(r)

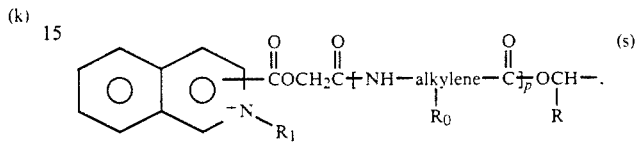
(s)

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; $R_3$ is $C_1$ to $C_3$ alkylene; X is —CONR'R" wherein R' and R", which can be the same or different, are each H or $C_1$-$C_7$ alkyl, or X is —CH=NOR'" wherein R'" is H or $C_1$-$C_7$ alkyl, the carbonyl-containing groupings in formulas (k) and (m) and the X substituent in formula (l) can each be attached at the 2, 3 or 4 position of the pyridinium ring; the carbonyl-containing groupings in formulas (n) and (p) and the X substituent in formula (o) can each be attached at the 2, 3 or 4 position of the quinolinium ring; and the carbonyl-containing groupings in formulas (q) and (s) and the X substituent in formula (r) can each be attached at the 1, 3 or 4 position of the isoquinolinium ring.

5. A salt as defined by claim 4, wherein p is zero.

6. A salt as defined by claim 4, wherein p is one, alkylene is —CH$_2$— and $R_o$ is H, —CH$_3$, —CH(CH$_3$)$_2$, —CH$_2$—CH(CH$_3$)$_2$,

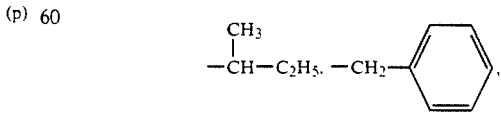

—(CH$_2$)$_2$—SCH$_3$, —CH$_2$—CONH$_2$ or —CH$_2$CH$_2$—CONH$_2$.

7. A salt having the structural formula (Ia)

wherein each $R_5$ is independently selected from the group consisting of H and $C_1$–$C_7$ alkyl, or an $R_5$ can be combined with the adjacent $$\diagdown_{\phantom{x}}C-R_5$$

such that $$\diagdown_{\phantom{x}}C\diagup^{R_5}_{R_5}$$

represents $$\diagdown_{\phantom{x}}C=O;$$

each $R_6$ is independently selected from the group consisting of H and $C_1$–$C_7$ alkyl, or an $R_6$ can be combined with the adjacent $$\diagdown_{\phantom{x}}C-R_6$$

such that $$\diagdown_{\phantom{x}}C\diagup^{R_6}_{R_6}$$

represents $$\diagdown_{\phantom{x}}C=O;\quad \text{HN}\diagdown_{\phantom{x}}\diagup\text{NH}$$
$$\phantom{xxxxxxxxx}Q'$$

is a radical of the formula $$\text{HN}\diagdown_{\phantom{x}}\diagup\text{NH}$$
$$R_7\phantom{x}R_7\phantom{x}R_7\phantom{x}(\text{alk})_s\text{-A}_3\text{-[QC}^-]$$

or (structure with phenylene ring bearing HN— and —NH substituents and —(alk)$_s$–A$_3$–[QC$^-$])

wherein each $R_7$ is independently selected from the group consisting of H and $C_1$–$C_7$ alkyl; (alk) is a straight or branched lower alkylene group which additionally may contain 1, 2 or 3 oxygen atoms in the chain, said oxygen atoms being nonadjacent to each other and also being nonadjacent to —A$_3$—; X$^-$ is the anion of a pharmaceutically acceptable organic or inorganic acid; n is the valence of the acid anion; m' is a number which when multiplied by n is equal to one; s is zero or one; —A$_3$— is —COO—; and [QC$^+$] is a radical of the formula (i)

(pyridinium structure)—$\overset{\overset{O}{\|}}{C}\!\!+\!\!NH\!-\!\text{alkylene}\!-\!\overset{\overset{O}{\|}}{C}\!\!\underset{R_0}{|}\!\!\text{)}_p Q\!-\!Z'\!-\!.$ (ii)

(4-X-pyridinium)—$R_3\!-\!\overset{\overset{O}{\|}}{C}\!\!+\!\!NH\!-\!\text{alkylene}\!-\!\overset{\overset{O}{\|}}{C}\!\underset{R_0}{|}\text{)}_p Q\!-\!Z'\!-\!,$ (iii)

(pyridinium)—$\overset{\overset{O}{\|}}{C}OCH_2\overset{\overset{O}{\|}}{C}\!\!+\!\!NH\!-\!\text{alkylene}\!-\!\overset{\overset{O}{\|}}{C}\!\underset{R_0}{|}\text{)}_p Q\!-\!Z'\!-\!,$ (iv)

(quinolinium)—$\overset{\overset{O}{\|}}{C}\!\!+\!\!NH\!-\!\text{alklyene}\!-\!\overset{\overset{O}{\|}}{C}\!\underset{R_0}{|}\text{)}_p Q\!-\!Z'\!-\!,$ (v)

(4-X-quinolinium)—$R_3\!-\!\overset{\overset{O}{\|}}{C}\!\!+\!\!NH\!-\!\text{alkylene}\!-\!\overset{\overset{O}{\|}}{C}\!\underset{R_0}{|}\text{)}_p Q\!-\!Z'\!-\!.$ -continued

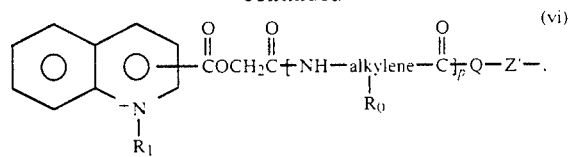

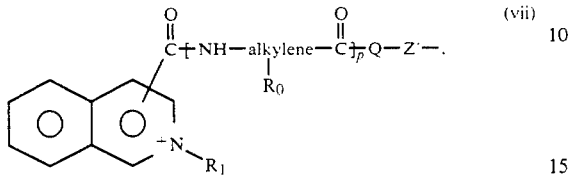

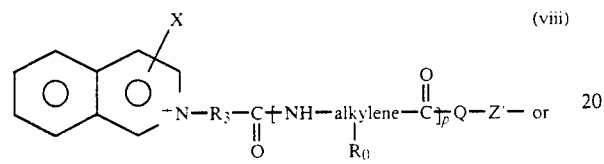

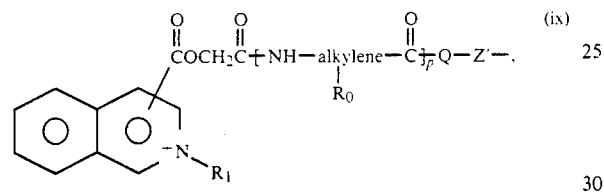

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $Z'$ is $C_1$-$C_8$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R" wherein R' and R", which can be the same or different, are each H or $C_1$-$C_7$ alkyl, or X is —CH=NOR'" wherein R'" is H or $C_1$-$C_7$ alkyl, the X substituent in formula (ii) and the carbonyl-containing groupings in formulas (i) and (iii) can each be attached at the 2, 3 or 4 position of the pyridinium ring; the X substituent in formula (v) and the carbonyl-containing groupings in formulas (iv) and (vi) can each be attached at the 2, 3 or 4 position of the quinolinium ring; and the X substituent in formula (viii) and carbonyl-containing groupings in formulas (vii) and (ix) can each be attached at the 1, 3 or 4 position of the isoquinolinium ring.

8. A salt having the structural formula

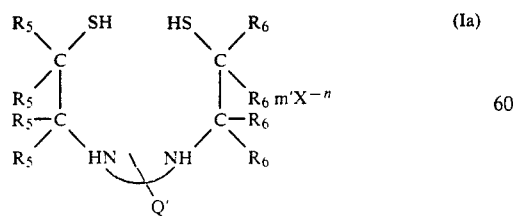

wherein each $R_5$ is independently selected from the group consisting of H and $C_1$-$C_7$ alkyl, or an $R_5$ can be combined with the adjacent

such that

represents

each $R_6$ is independently selected from the group consisting of H and $C_1$-$C_7$ alkyl, or an $R_6$ can be combined with the adjacent $$\diagdown C-R_6 \diagup$$

such that $$\diagdown_{\diagup}C\diagdown^{R_6}_{R_6}$$

represents $$\diagdown C=O; \quad HN\diagdown_{Q'}\diagup NH$$

is a radical of the formula

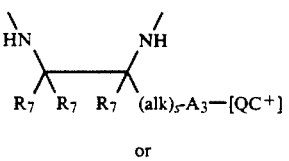

or

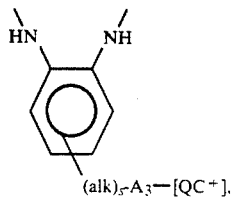

wherein each $R_7$ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —A₃—; X is the anion of a pharmaceutically acceptable organic or inorganic acid; n is the valence of the acid anion; m' is a number which when multiplied by n is equal to one; s is zero or one; —A₃— is —COO—; and [QC⁺] is a radical of the formula

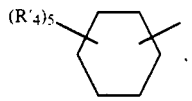 (x)

 (xi)

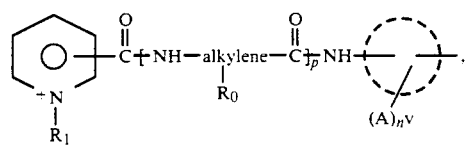 (xii)

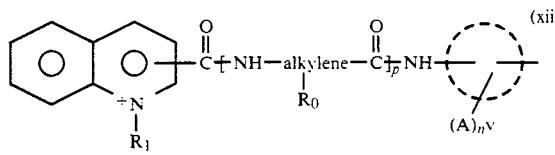 (xiii)

or

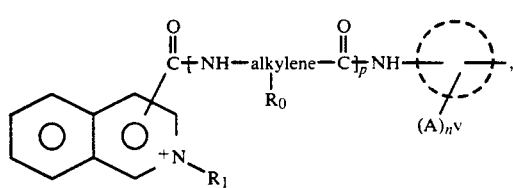 (xiv)

wherein is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii), (xiii) and (xiv) is hydroxy; and each R'₄ in each of structures (x) and (xi) can independently be hydroxy,

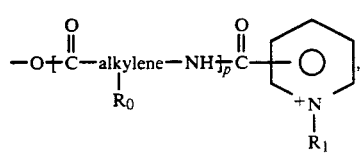

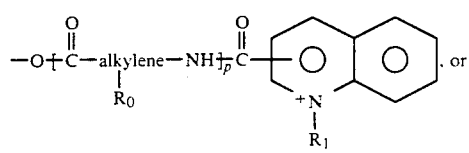, or

-continued

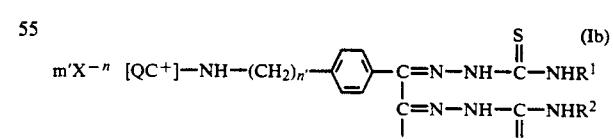

wherein the alkylene group can be straight or branched and can contain 1 to 3 carbon atoms; R₀ is a radical identical to the corresponding portion of a natural amino acid; p is 0, 1 or 2, provided that, when p is 2, then the alkylene groups can be the same or different and the R₀ radicals can be the same or different; R₁ is C₁-C₇ alkyl, C₁-C₇ haloalkyl or C₇-C₁₀ aralkyl; and the depicted carbonyl-containing groupings can be attached at the 2, 3 or 4 position of the pyridinium or quinolinium ring, or at the 1, 3 or 4 position of the isoquinolinium ring; with the proviso that at least one R'₄ in each of structures (x) and (xi) is

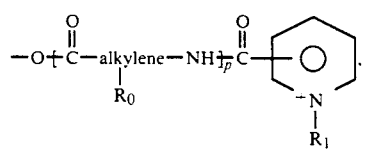

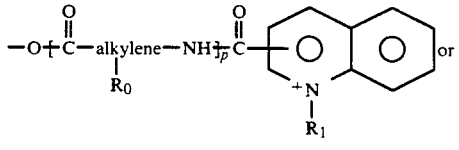 or

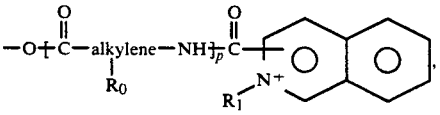, wherein alkylene, R₀, p and R₁ and the position of the carbonyl-containing groupings are defined as above; and with the further proviso that when more than one of the R'₄ radicals in a given compound are the aforesaid carbonyl-containing groupings, then all such carbonyl-containing groupings in said compound are identical.

9. A salt having the structural formula $$m'X^{-n} \; [QC^+]-NH-(CH_2)_{n'}-\underset{}{\bigcirc}-\underset{CH_3}{\overset{C=N-NH-\overset{S}{\overset{\|}{C}}-NHR^1}{\underset{C=N-NH-\overset{\|}{C}-NHR^2}{|}}} \quad \text{(Ib)}$$

wherein R¹ and R² are each H or C₁-C₃ alkyl, n' is an integer of 0 to 3, X⁻ is the anion of a pharmaceutically acceptable organic or inorganic acid, n is the valence of the acid anion, m' is a number which when multiplied by n is equal to one; and [QC⁺] is a radical of the formula (a) 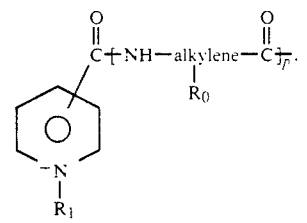

(b) 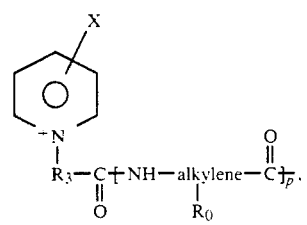

(c) 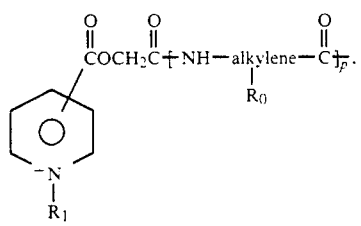

(d) 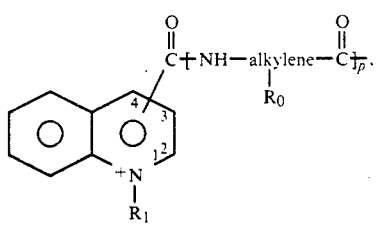

(e) 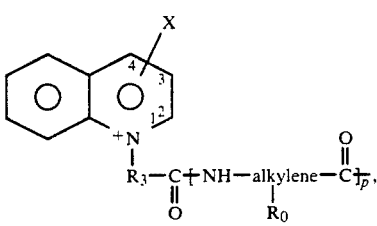

(f) 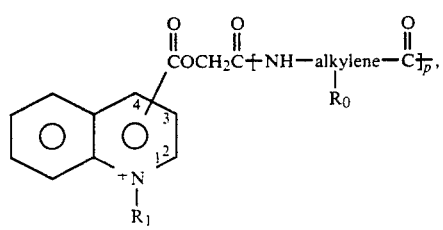

(g) 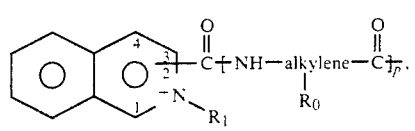

(h) 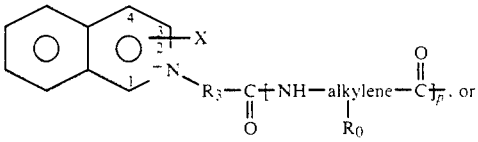

(j) 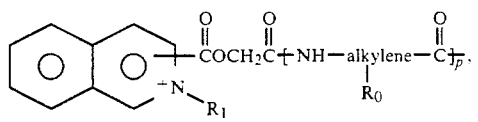

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring.

10. A salt as defined by claim 9, wherein p is zero.

11. A salt as defined by claim 9, wherein p is one, alkylene is —$CH_2$— and $R_o$ is H, —$CH_3$, —$CH(CH_3)_2$, —$CH_2$—$CH(CH_3)_2$,

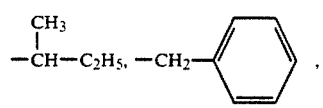

—$(CH_2)_2$—$SCH_3$, —$CH_2$—$CONH_2$ or —$CH_2CH_2$—$CONH_2$.

12. A salt as defined by claim 9, having the structural formula (Ib') 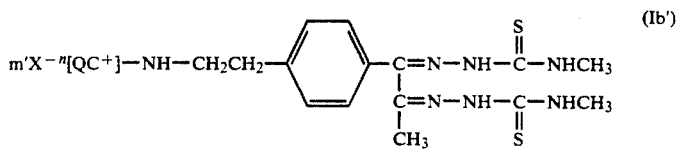

wherein m', $X^-$, n and [$QC^+$] are as defined in claim 9.

13. A salt as defined by claim 12, wherein p is zero.

14. A salt as defined by claim 12, wherein p is one, alkylene is —$CH_2$— and $R_o$ is H, —$CH_3$, —$CH(CH_3)_2$, —$CH_2$—$CH(CH_3)_2$,

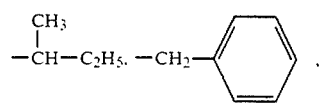

$(CH_2)_2-SCH_3$, $-CH_2-CONH_2$ or $-CH_2CH_2-CONH_2$.

15. A compound having the structural formula

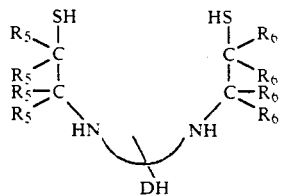 (IIa)

wherein each $R_5$ is independently selected from the group consisting of H and $C_1-C_7$ alkyl, or an $R_5$ can be combined with the adjacent

such that

represents

each $R_6$ is independently selected from the group consisting of H and $C_1-C_7$ alkyl, or an $R_6$ can be combined with the adjacent

such that

represents

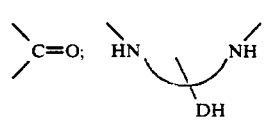

is a radical of the formula

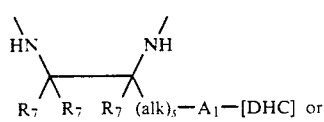

-continued

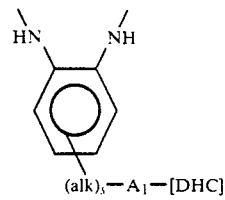

wherein each $R_7$ is independently selected from the group consisting of H and $C_1-C_7$ alkyl; (alk) is a straight or branched lower alkylene group which additionally may contain 1, 2 or 3 oxygen atoms in the chain, said oxygen atoms being nonadjacent to each other and also being nonadjacent to $-A_1-$; s is zero or one; $-A_1-$ is $-NH-$, $-O-$ or

wherein $R_8$ is $C_1-C_7$ alkyl; and [DHC] is a radical of the formula

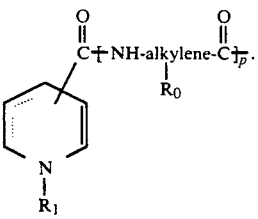 (a')

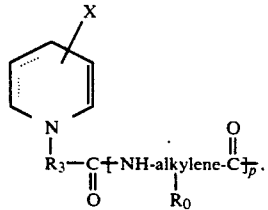 (b')

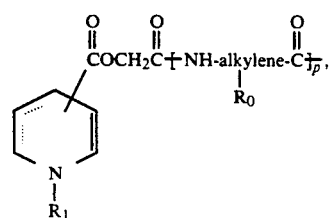 (c')

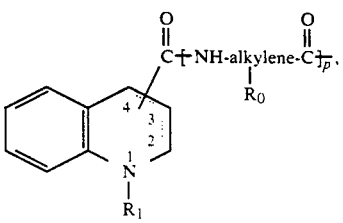 (d')

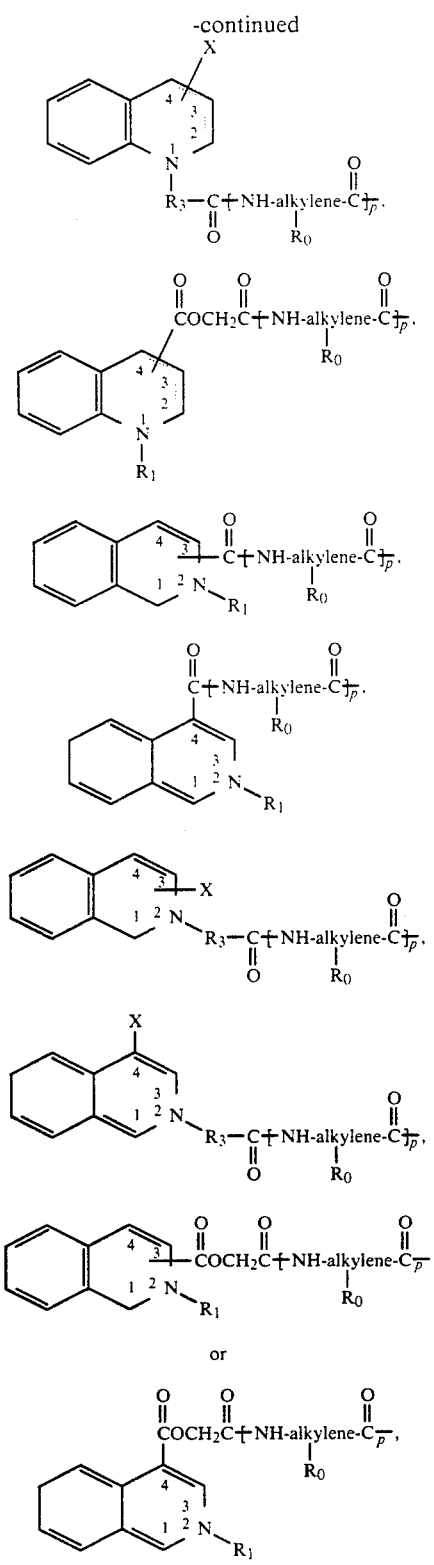

or wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

16. A compound as defined by claim 15, wherein p is zero.

17. A compound as defined by claim 15, wherein p is one, alkylene is —$CH_2$— and $R_o$ is H, —$CH_3$, —$CH(CH_3)_2$, —$CH_2$—$CH(CH_3)_2$,

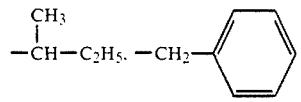

—$(CH_2)_2$—$SCH_3$, —$CH_2$—$CONH_2$ or —$CH_2CH_2$—$CONH_2$.

18. A compound having the structural formula

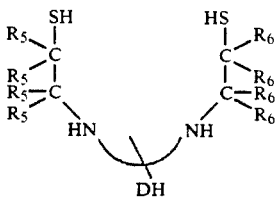

(IIa)

wherein each $R_5$ is independently selected from the group consisting of H and $C_1$-$C_7$ alkyl, or an $R_5$ can be combined with the adjacent

such that

represents

each $R_6$ is independently selected from the group consisting of H and $C_1$-$C_7$ alkyl, or an $R_6$ can be combined with the adjacent

such that

represents

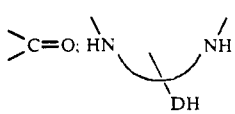

is a radical of the formula

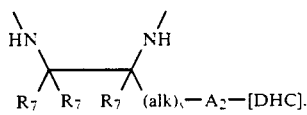

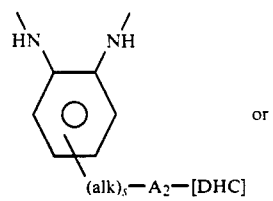

or

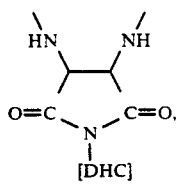

wherein each $R_7$ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —$A_2$—; s is zero or one; —$A_2$— is —CONH— or

wherein $R_9$ is $C_1$-$C_7$ alkyl; and [DHC] is a radical of the formula

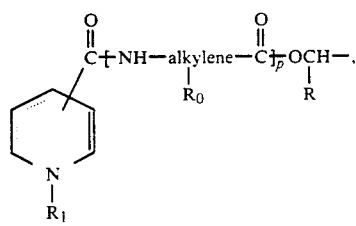
(k')

-continued

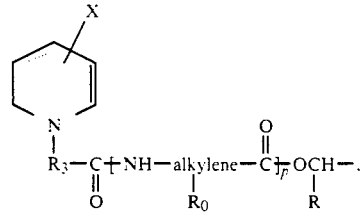
(l')

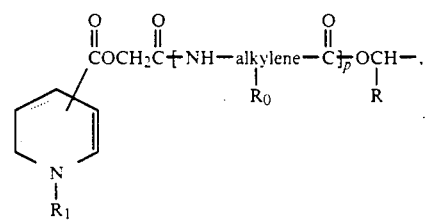
(m')

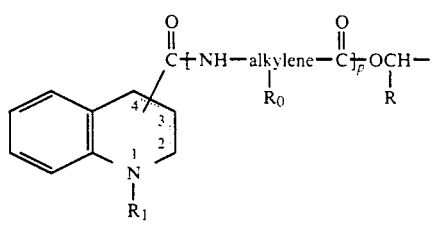
(n')

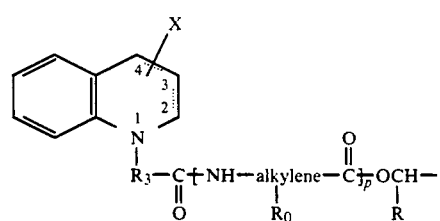
(o')

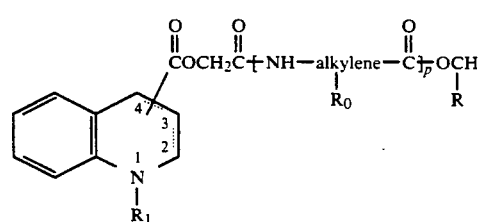
(p')

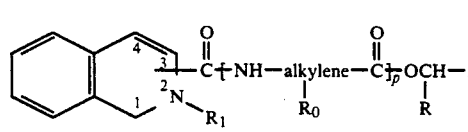
(q')

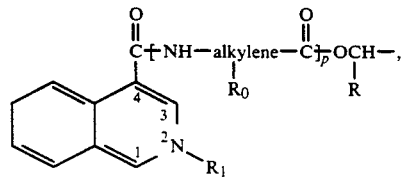
(q'')

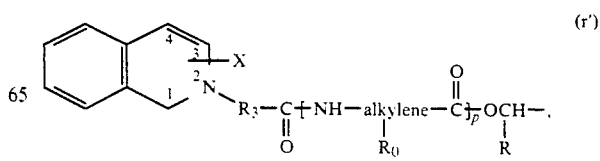
(r')

-continued

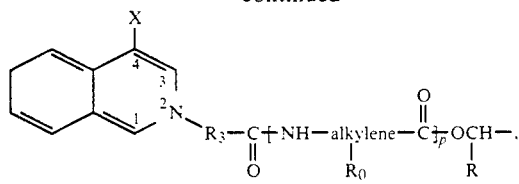  (r")

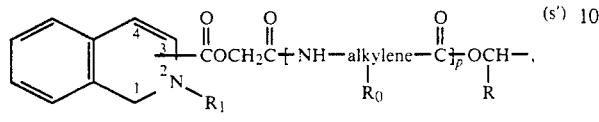  (s')

or

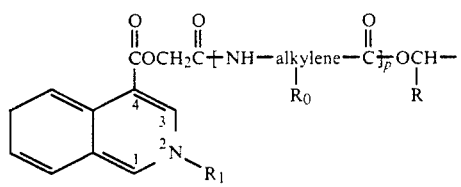  (s")

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; the dotted line in formulas (k'), (l') and (m') indicates the presence of a double bond in either the 4 or 5 position of the dihydropyridine ring; the dotted line in formulas (n'), (o') and (p') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR'" wherein R'" is H or $C_1$-$C_7$ alkyl; the carbonyl-containing groupings in formulas (k') and (m') and the X substituent in formula (l') can each be attached at the 2, 3 or 4 position of the dihydropyridine ring; the carbonyl-containing groupings in formulas (n') and (p') and the X substituent in formula (o') can each be attached at the 2, 3 or 4 position of the dihydroquinoline ring; and the carbonyl-containing groupings in formulas (q') and (s') and the X substituent in formula (r') can each be attached at the 1, 3 or 4 position of the dihydroisoquinoline ring.

19. A compound as defined by claim 18, wherein p is zero.

20. A compound as defined by claim 18, wherein p is one, alkylene is —$CH_2$— and $R_o$ is H, —$CH_3$, —$CH(CH_3)_2$, —$CH_2$—$CH(CH_3)_2$,

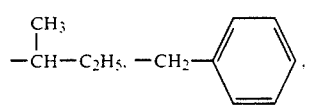

—$(CH_2)_2$—$SCH_3$, —$CH_2$—$CONH_2$ or —$CH_2CH_2$—$CONH_2$.

21. A compound having the structural formula

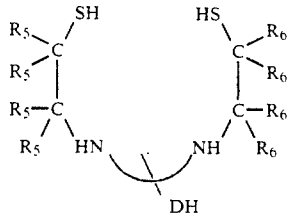  (IIa)

wherein each $R_5$ is independently selected from the group consisting of H and $C_1$-$C_7$ alkyl, or an $R_5$ can be combined with the adjacent

such that

represents

each $R_6$ is independently selected from the group consisting of H and $C_1$-$C_7$ alkyl, or an $R_6$ can be combined with the adjacent

such that

represents

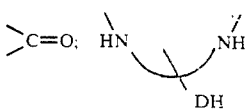

is a radical of the formula

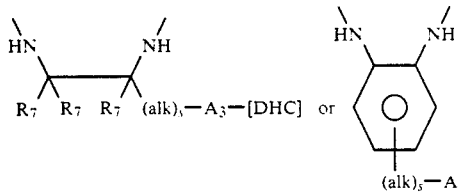

wherein each R₇ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —A₃—; s is zero or one; —A₃— is —COO—; and [DHC] is a radical of the formula

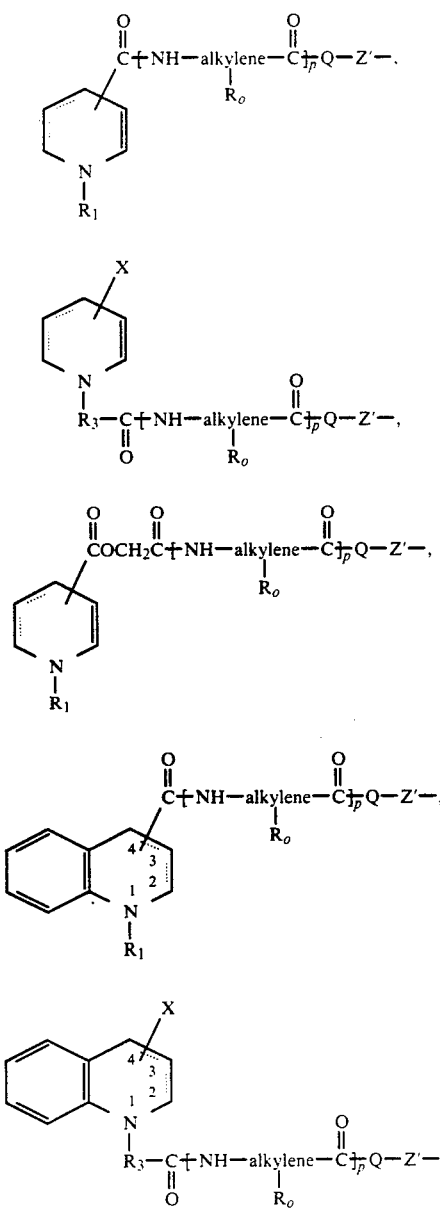

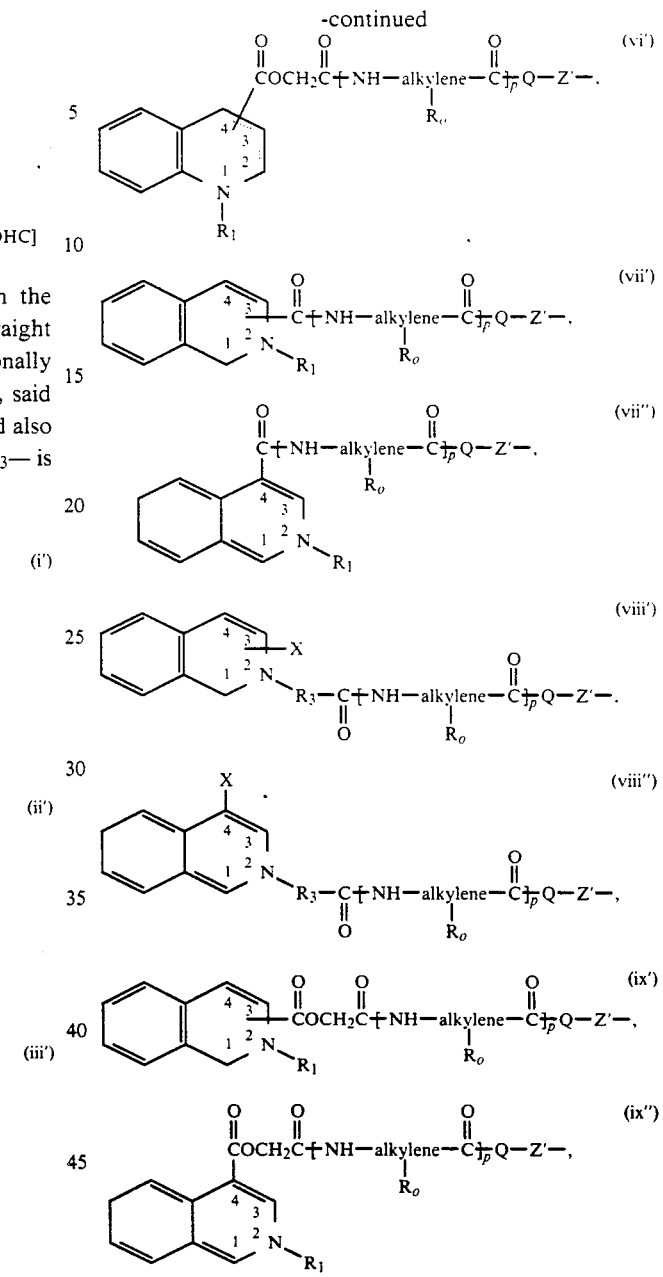

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (i'), (ii') and (iii') indicates the presence of a double bond in either the 4 or 5 position of the dihydropyridine ring; the dotted line in formulas (iv'), (v') and (vi') indicates the presence of a double bond in either the 2 or 3 position of the dihydroquinoline ring; Z' is $C_1$-$C_8$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R" wherein R' and R", which can be the same or different, are each H or $C_1$-$C_7$ alkyl, or X is —CH═NOR''' wherein R''' is H or $C_1$-$C_7$ alkyl; the X substituent in formula (ii') and the carbonyl-containing groupings in formulas (i') and (iii') can each be attached at the 2, 3 or 4 position of the dihydropyridine ring; the X substituent in formula (v') and the carbonyl-containing groupings in formulas (iv') and (vi') can each be attached at the 2, 3 or 4 position of the dihydroquinoline ring; and the X substituent in formula (viii') and the carbonyl-containing groupings in formulas (vii') and (ix') can each be attached at the 1, 3 or 4 position of the dihydroisoquinoline ring.

22. A compound having the structural formula

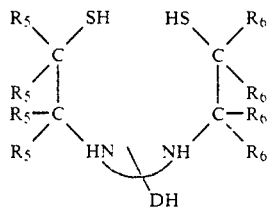 (IIa)

wherein each $R_5$ is independently selected from the group consisting of H and $C_1$-$C_7$ alkyl, or an $R_5$ can be combined with the adjacent

such that

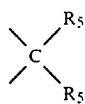

represents

each $R_6$ is independently selected from the group consisting of H and $C_1$-$C_7$ alkyl, or an $R_6$ can be combined with the adjacent

such that

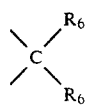

represents

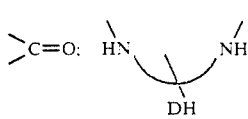

is a radical of the formula

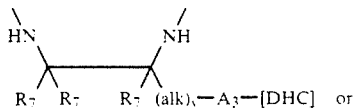

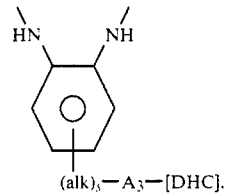

wherein each $R_7$ is independently selected from the group consisting of H and $C_1$-$C_7$ alkyl; (alk) is a straight or branched lower alkylene group which additionally may contain 1, 2 or 3 oxygen atoms in the chain, said oxygen atoms being nonadjacent to each other and also being nonadjacent to —$A_3$—; s is zero or one; —$A_3$— is —COO—; and [DHC] is a radical of the formula

 (x')

 (xi')

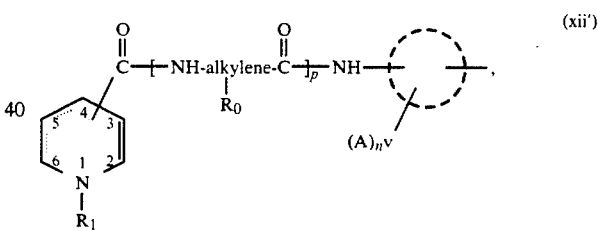 (xii')

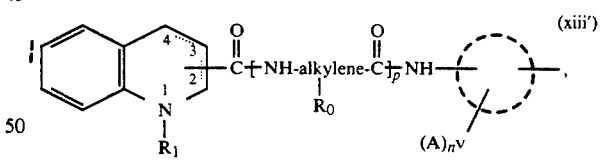 (xiii')

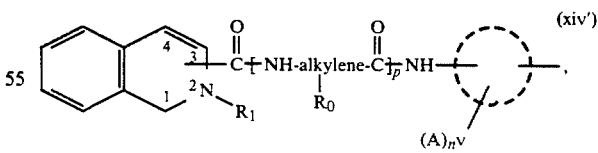 (xiv')

or

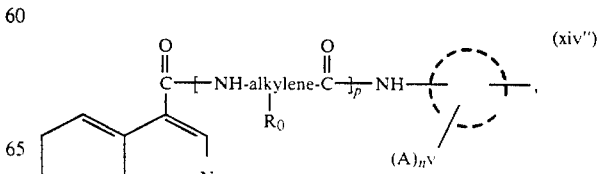 (xiv")

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formula (xii′) indicates the presence of a double bond in either the 4 or 5 position of the dihydropyridine ring; the dotted line in formula (xiii′) indicates the presence of a double bond in either the 2 or 3 position of the dihydroquinoline ring;

is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii′), (xiii′), (xiv′) and (xiv″) is hydroxy; and each $R_4$ in each of structures (x′) and (xi′) can independently be hydroxy,

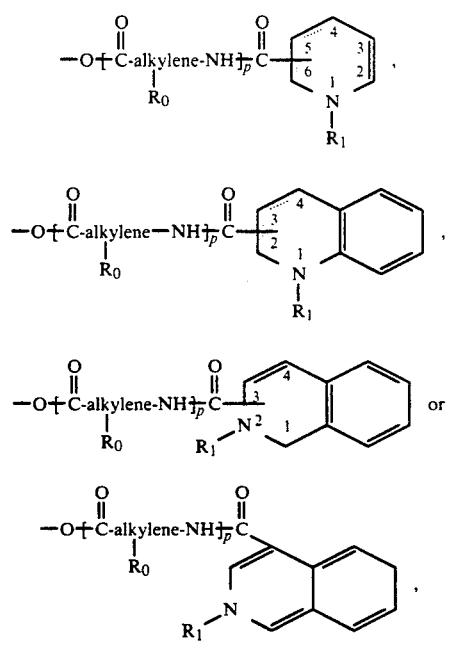

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line is defined as with structures (xii′) and (xiii′); $R_1$ is $C_1$-$C_7$ alkyl, $C_1$-$C_7$ haloalkyl or $C_7$-$C_{10}$ aralkyl; and the depicted carbonyl groupings can be attached at the 2, 3 or 4 position of the pyridinium or quinolinium ring or, except where otherwise specified, at the 1, 3 or 4 position of the isoquinolinium ring; with the proviso that at least one $R_4$ in each of structures (x′) and (xi′) is

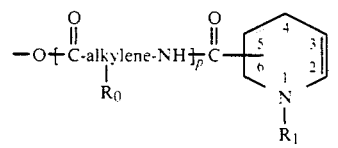

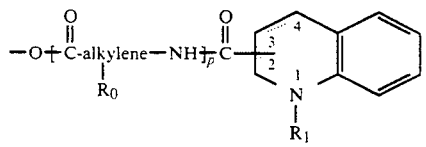

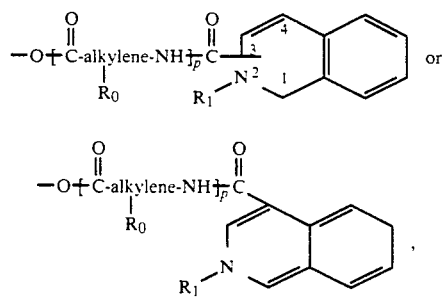

wherein alkylene, $R_o$, p, $R_1$, the dotted lines and the position of the carbonyl-containing groupings are defined as above; and with the further proviso that when more than one of the $R_4$ radicals in a given compound are the aforesaid carbonyl-containing groupings, then all such carbonyl-containing groupings in said compound are identical.

23. A compound having the structural formula

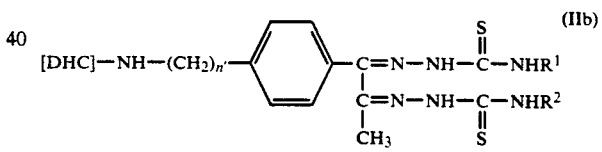

wherein $R^1$ and $R^2$ are each H or $C_1$-$C_3$ alkyl, n′ is an integer of 0 to 3 and [DHC] is a radical of the formula

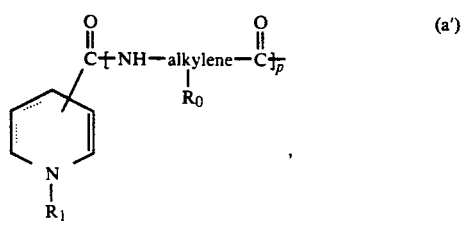

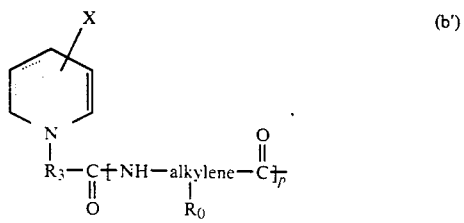

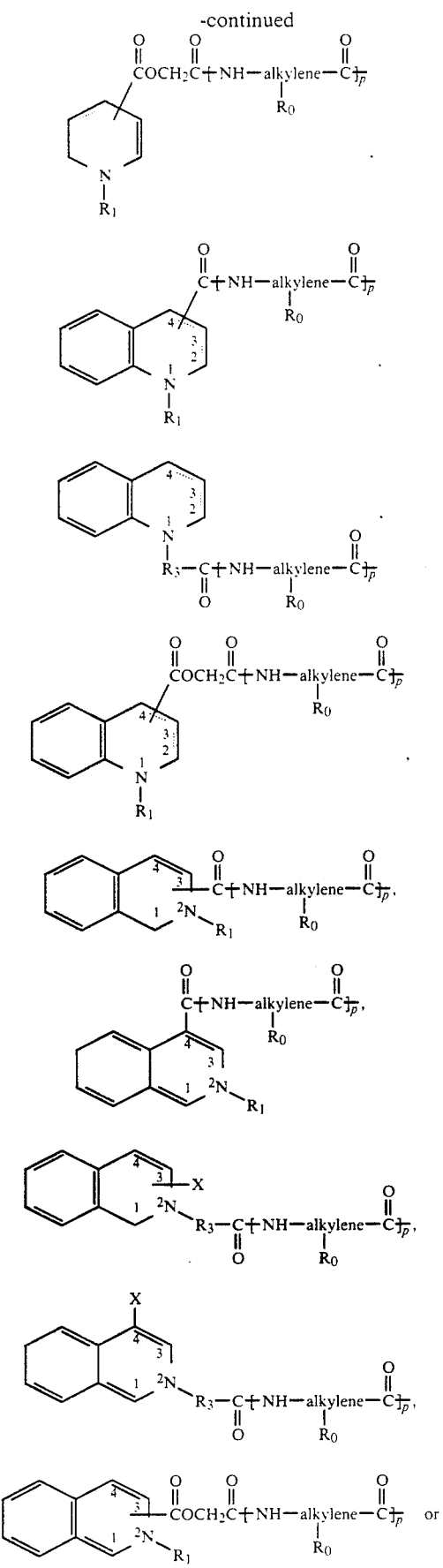

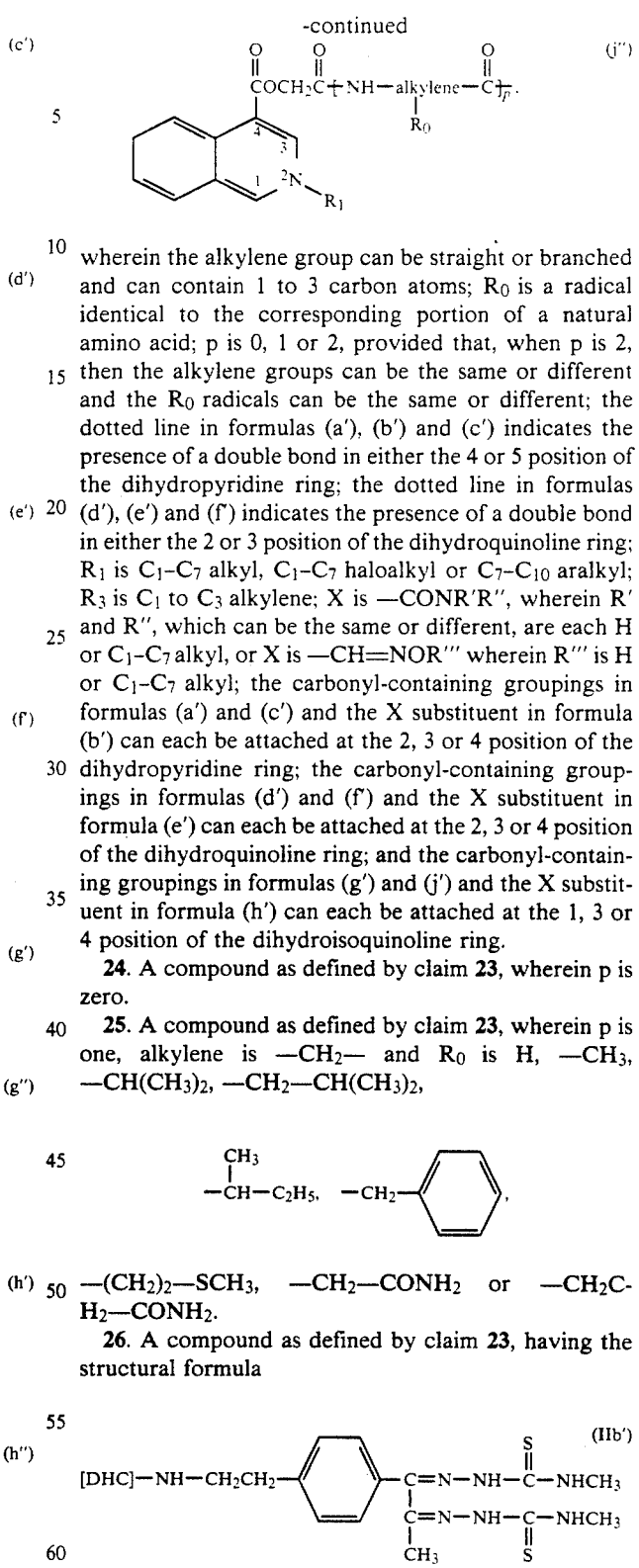

wherein the alkylene group can be straight or branched and can contain 1 to 3 carbon atoms; $R_0$ is a radical identical to the corresponding portion of a natural amino acid; p is 0, 1 or 2, provided that, when p is 2, then the alkylene groups can be the same or different and the $R_0$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R", wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

24. A compound as defined by claim 23, wherein p is zero.

25. A compound as defined by claim 23, wherein p is one, alkylene is —CH$_2$— and $R_0$ is H, —CH$_3$, —CH(CH$_3$)$_2$, —CH$_2$—CH(CH$_3$)$_2$, $$-\underset{\underset{CH_3}{|}}{CH}-C_2H_5, \quad -CH_2-\text{phenyl},$$

—(CH$_2$)$_2$—SCH$_3$, —CH$_2$—CONH$_2$ or —CH$_2$CH$_2$—CONH$_2$.

26. A compound as defined by claim 23, having the structural formula $$[DHC]-NH-CH_2CH_2-\text{phenyl}-\begin{array}{c}C=N-NH-\overset{S}{\underset{\|}{C}}-NHCH_3 \\ | \\ C=N-NH-\overset{}{\underset{\|}{C}}-NHCH_3 \\ | \quad\quad\quad\quad\| \\ CH_3 \quad\quad\quad\quad S\end{array}$$ (IIb')

wherein [DHC] is as defined in claim 23.

27. A compound as defined by claim 26, wherein p is zero.

28. A compound as defined by claim 26, wherein p is one, alkylene is —CH$_2$— and $R_0$ is H, —CH$_3$, —CH(CH$_3$)$_2$, —CH$_2$—CH(CH$_3$)$_2$,

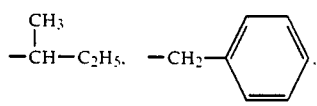

—(CH₂)₂—SCH₃, —CH₂—CONH₂ or —CH₂CH₂—CONH₂.

29. A salt as defined by claim 1, wherein R₁ is methyl.
30. A salt as defined by claim 9, wherein R₁ is methyl.
31. A compound as defined by claim 15, wherein R₁ is methyl.
32. A compound as defined by claim 23, wherein R₁ is methyl.
33. A salt as defined by claim 1, wherein R₃ is —CH₂CH₂—.
34. A salt as defined by claim 9, wherein R₃ is —CH₂CH₂—.
35. A compound as defined by claim 15, wherein R₃ is —CH₂CH₂—.
36. A compound as defined by claim 23, wherein R₃ is —CH₂CH₂—.
37. A salt as defined by claim 1, wherein X is —CONH₂.
38. A salt as defined by claim 9, wherein X is —CONH₂.
39. A compound as defined by claim 15, wherein X is —CONH₂.
40. A compound as defined by claim 23, wherein X is —CONH₂.
41. A salt as defined by claim 1, wherein the X and carbonyl-containing groupings whose ring positions can vary are located in the 3 position of the pyridinium ring, in the 3 position position of the quinolinium ring system or in the 4 position of the isoquinolinium ring system.
42. A salt as defined by claim 9, wherein the X and carbonyl-containing groupings whose ring positions can vary are located in the 3 position of the pyridinium ring, in the 3 position of the quinolinium ring system or in the 4 position of the isoquinolinium ring system.
43. A compound as defined by claim 15, wherein the X and carbonyl-containing groupings whose ring positions can vary are located in the 3 position of the dihydropyridine ring, in the 3 position of the dihydroquinoline ring system or in the 4 position of the dihydroisoquinoline ring system.
44. A compound as defined by claim 23, wherein the X and carbonyl-containing groupings whose ring positions can vary are located in the 3 position of the dihydropyridine ring, in the 3 position of the dihydroquinoline ring system or in the 4 position of the dihydroisoquinoline ring system.
45. A salt as defined by claim 1, wherein [QC⁺] is a radical of formula (a).
46. A salt as defined by claim 9, wherein [QC⁺] is a radical of formula (a).
47. A compound as defined by claim 15, wherein [DHC] is a radical of formula (a').
48. A compound as defined by claim 23, wherein [DHC] is a radical of formula (a').
49. A salt as defined by claim 45, wherein the radical of formula (a) has the formula

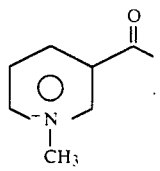

50. A salt as defined by claim 46, wherein the radical of formula (a) has the formula

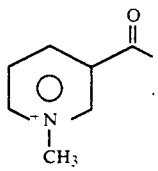

51. A compound as defined by claim 47, wherein the radical of formula (a') has the formula

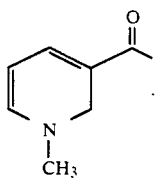

52. A compound as defined by claim 48, wherein the radical of formula (a') has the formula

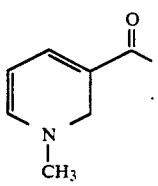

53. A salt as defined by claim 4, wherein R₁ is methyl.
54. A compound as defined by claim 18, wherein R₁ is methyl.
55. A salt as defined by claim 4, wherein the X and carbonyl-containing groupings whose ring positions can vary are located in the 3 position of the pyridinium ring, in the 3 position of the quinolinium ring system or in the 4 position of the isoquinolinium ring system.
56. A compound as defined by claim 18, wherein the X and carbonyl-containing groupings whose ring positions can vary are located in the 3 position of the dihydropyridine ring, in the 3 position of the dihydroquinoline ring system or in the 4 position of the dihydroisoquinoline ring system.
57. A salt as defined by claim 4, wherein R is hydrogen, C₁-C₇ alkyl, C₃-C₈ cycloalkyl, C₁-C₇ haloalkyl, furyl or phenyl.
58. A compound as defined by claim 18, wherein R is hydrogen, C₁-C₇ alkyl, C₃-C₈ cycloalkyl, C₁-C₇ haloalkyl, furyl or phenyl.
59. A salt as defined by claim 7, wherein Z' is C₁-C₃ straight or branched alkylene.
60. A compound as defined by claim 21, wherein Z' is C₁-C₃ straight or branched alkylene.
61. A salt as defined by claim 7, wherein the X and carbonyl-containing groupings whose ring positions can vary are located in the 3 position of the pyridinium ring, in the 3 position of the quinolinium ring system or in the 4 position of the isoquinolinium ring system.

62. A compound as defined by claim 31, wherein the X and carbonyl-containing groupings whose ring positions can vary are located in the 3 position of the dihydropyridine ring, in the 3 position of the dihydroquinoline ring system or in the 4 position of the dihydroisoquinoline ring system.

63. A salt as defined by claim 8, wherein the carbonyl-containing groupings encompassed by the definition of R'$_4$ are located in the 3 position of the pyridinium ring, in the 3 position of the quinolinium ring system or in the 4 position of the isoquinolinium ring system.

64. A compound as defined by claim 22, wherein the carbonyl-containing groupings encompassed by the definition of R$_4$ are located in the 3 position of the dihydropyridine ring, in the 3 position of the dihydroquinoline ring system or in the 4 position of the dihydroisoquinoline ring system.

65. The salt having the structural formula

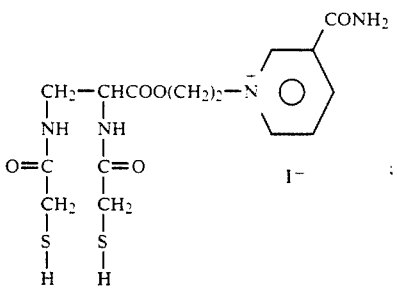

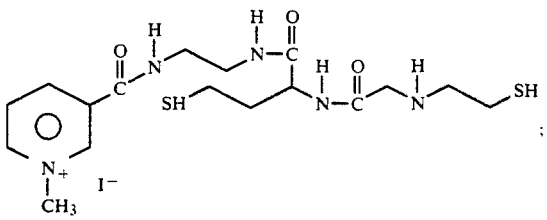

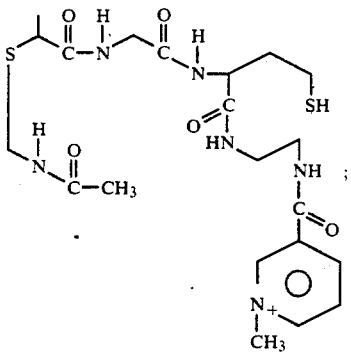

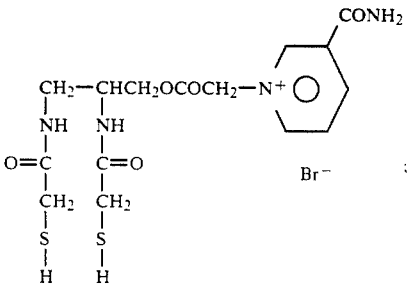

-continued
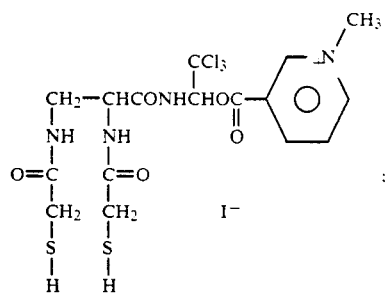
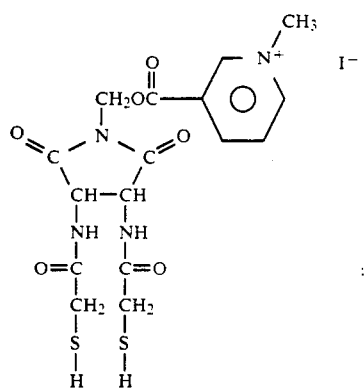
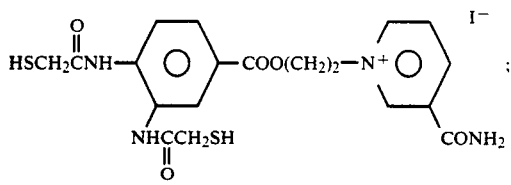
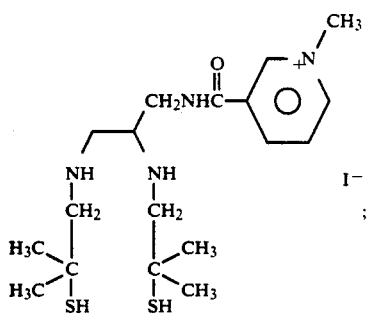
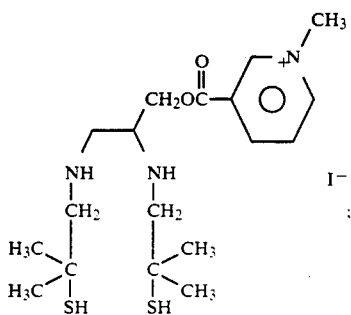

-continued
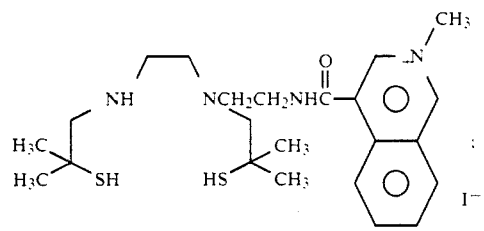
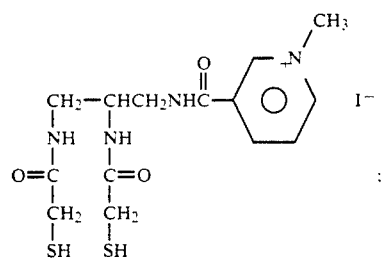
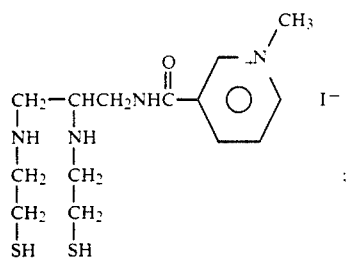
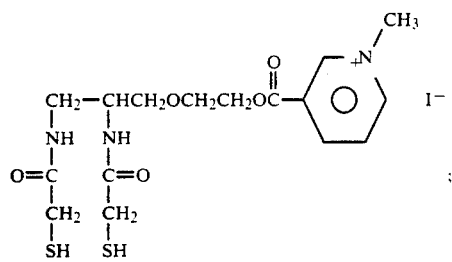
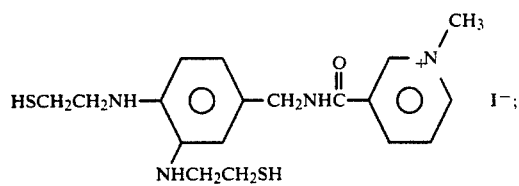
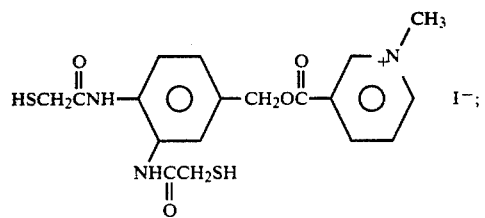
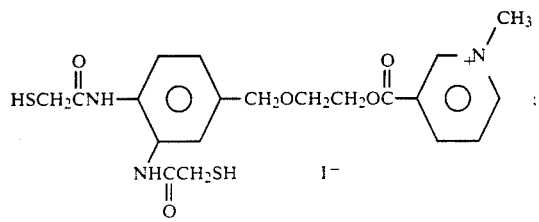

-continued
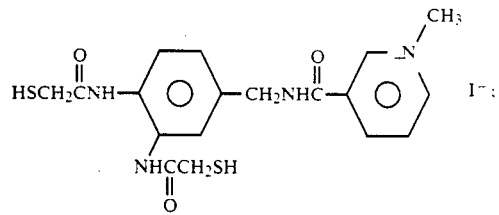
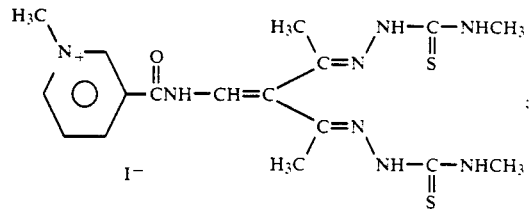
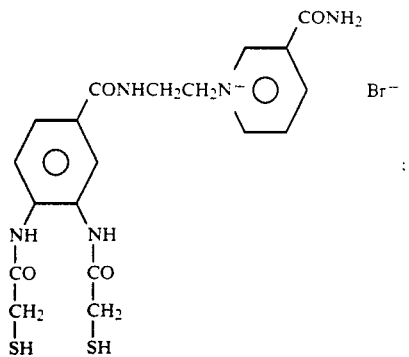
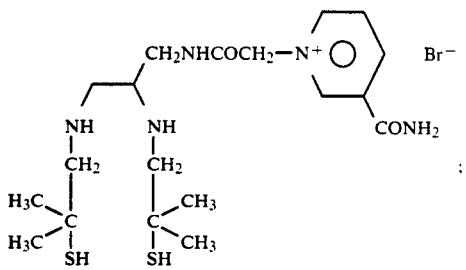
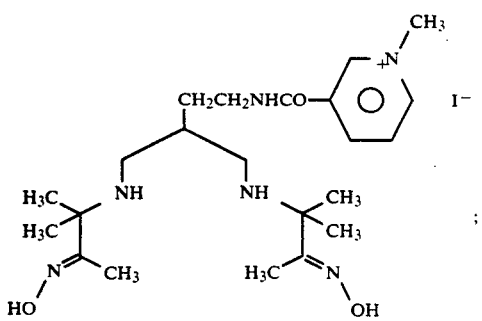
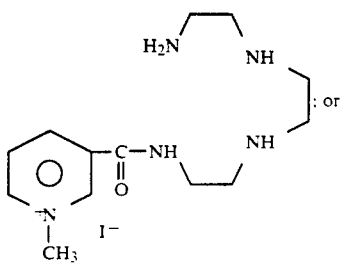

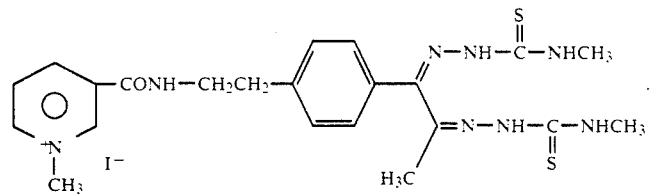
66. The compound having the structural formula
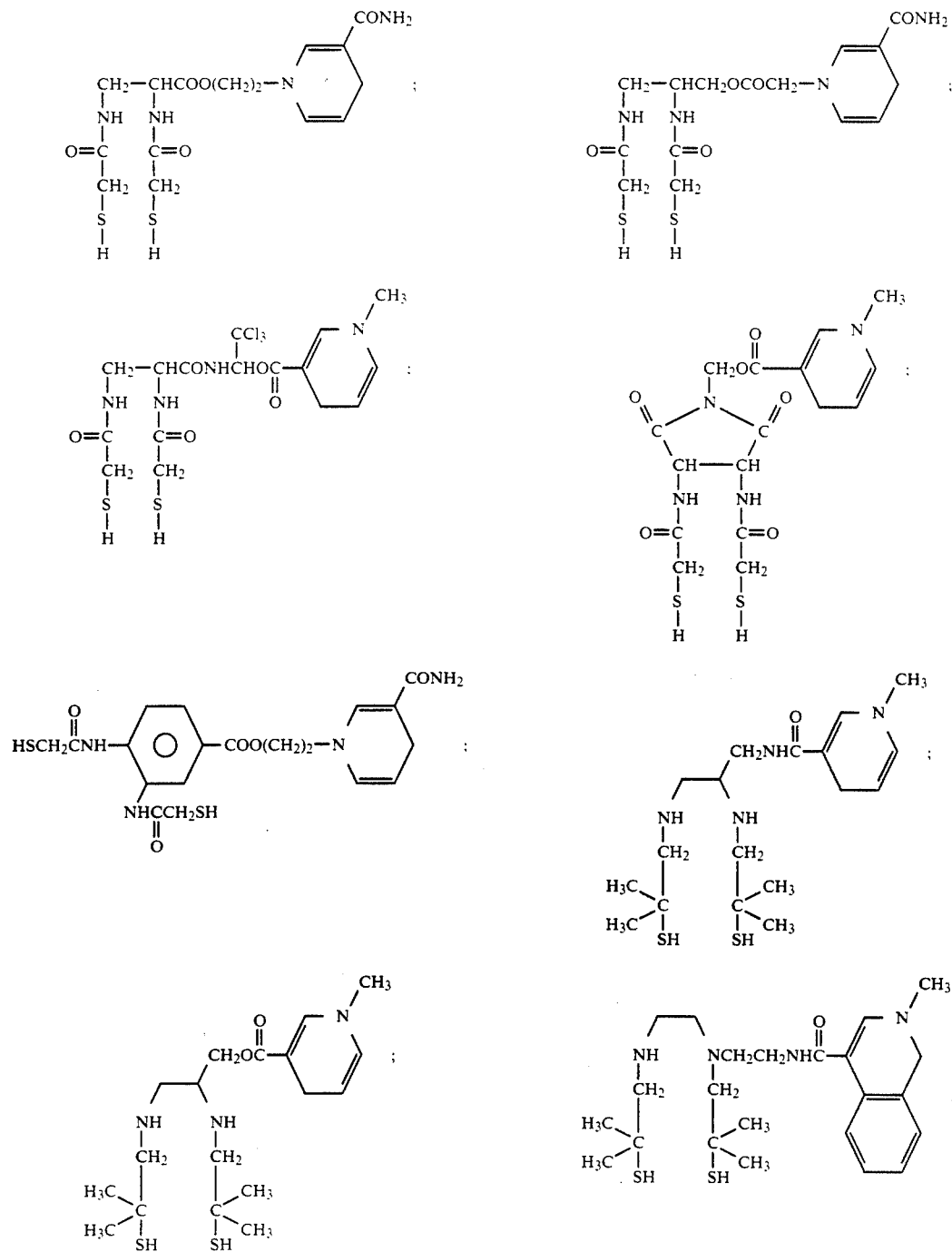

201
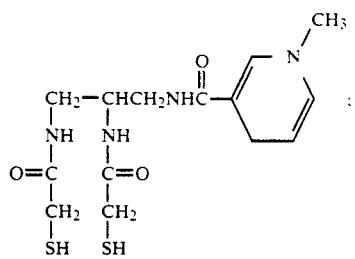
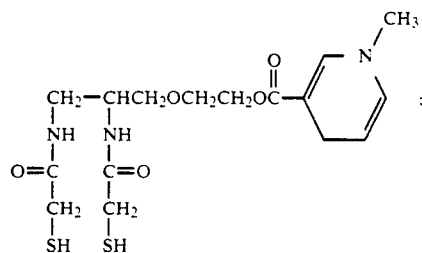
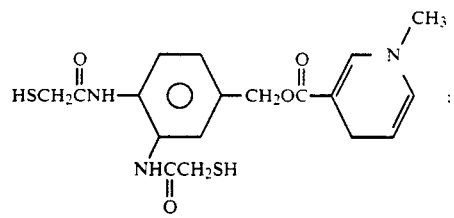
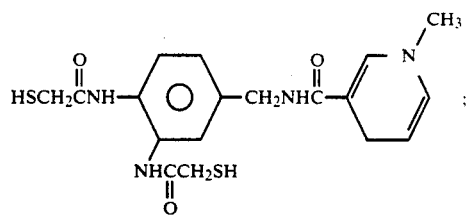
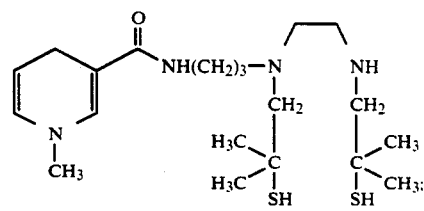
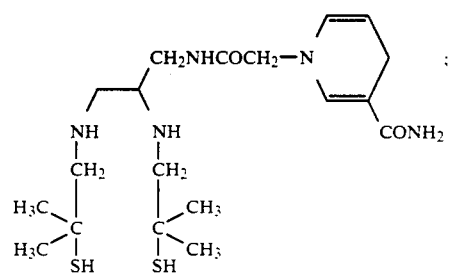
202
-continued
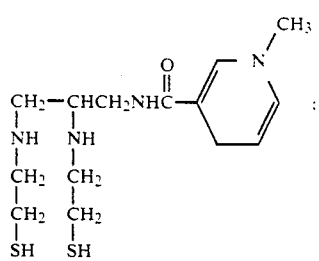
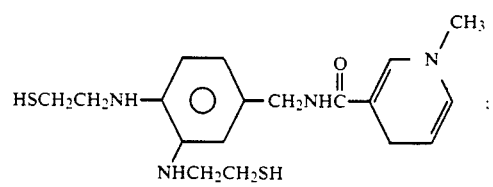
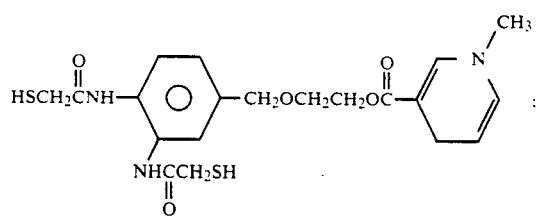
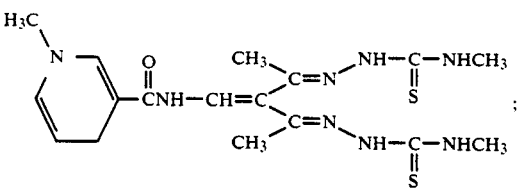
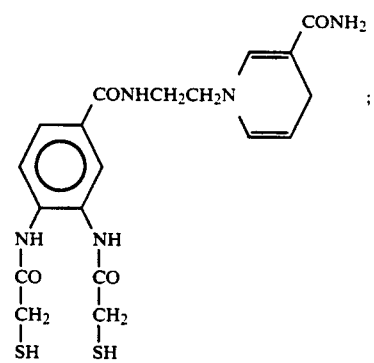
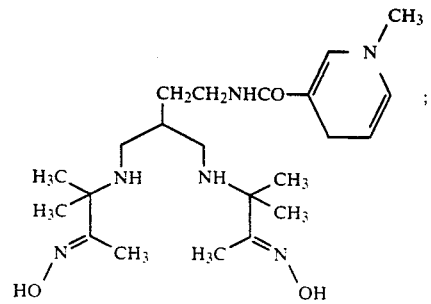

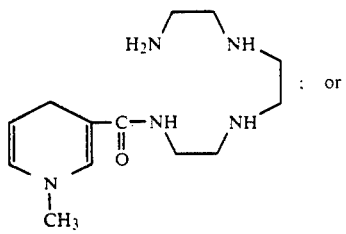
: or

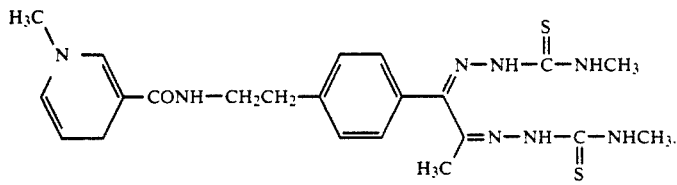

67. A salt having the structural formula

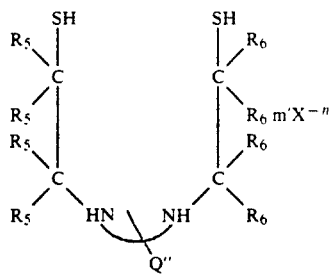
(Ia')

wherein each $R_5$ is independently selected from the group consisting of H and $C_1-C_7$ alkyl, or an $R_5$ can be combined with the adjacent

such that

represents

each $R_6$ is independently selected from the group consisting of H and $C_1-C_7$ alkyl, or an $R_6$ can be combined with the adjacent

such that

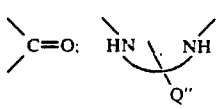

represents

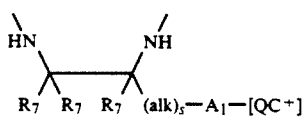

is a radical of the formula

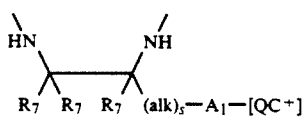

wherein each $R_7$ is independently selected from the group consisting of H and $C_1-C_7$ alkyl; (alk) is a straight or branched lower alkylene group which additionally may contain 1, 2 or 3 oxygen atoms in the chain, said oxygen atoms being nonadjacent to each other and also being nonadjacent to $-A_1-$; $X^-$ is the anion of a pharmaceutically acceptable organic or inorganic acid; n is the valence of the acid anion; m' is a number which when multiplied by n is equal to one; s is zero or one; $-A_1-$ is $-NH-$, $-O-$ or

wherein $R_8$ is $C_1$–$C_7$ alkyl; and [QC$^+$] is a radical of the formula

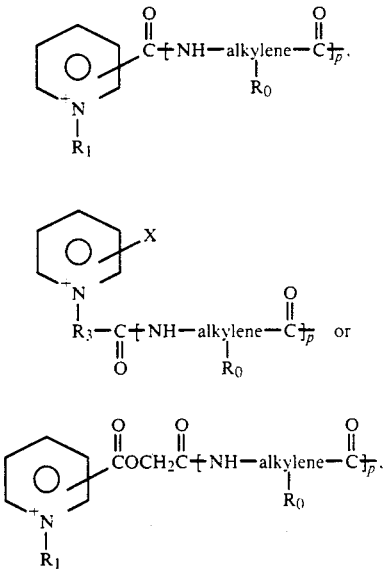

wherein the alkylene group can be straight or branched and can contain 1 to 3 carbon atoms; $R_0$ is hydrogen, methyl, —CH(CH$_3$)$_2$,

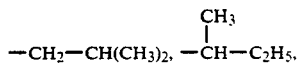

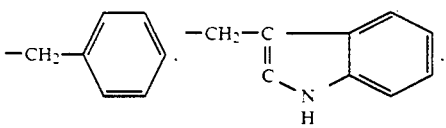

—CH$_2$OH, —CH(OH)CH$_3$, —(CH$_2$)$_2$—SCH$_3$, —CH$_2$CONH$_2$, —CH$_2$CH$_2$—CONH$_2$,

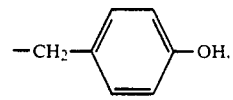

—CH$_2$SH, —CH$_2$COOH or —CH$_2$CH$_2$—COOH; p is 0, 1 or 2, provided that, when p is 2, then the alkylene groups can be the same or different and the $R_0$ radicals can be the same or different; $R_1$ is $C_1$–$C_7$ alkyl, $C_1$–$C_7$ haloalkyl or $C_7$–$C_{10}$ aralkyl; $R_3$ is $C_1$ to $C_3$ alkylene; X is —CONR'R" wherein R' and R", which can be the same or different, are each H or $C_1$–$C_7$ alkyl, or X is —CH=NOR'" wherein R'" is H or $C_1$–$C_7$ alkyl; and the carbonyl-containing groupings in formulas (a) and (c) and the X substituent in formula (b) can each be attached at the 2, 3 or 4 position of the pyridinium ring.

68. A salt as defined by claim 67, having the structural formula

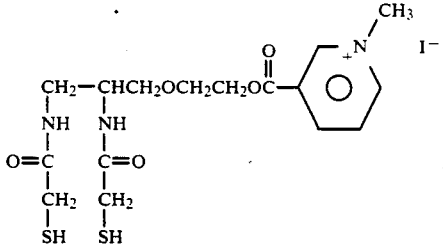

* * * * *